US012343406B2

(12) United States Patent
Won

(10) Patent No.: US 12,343,406 B2
(45) Date of Patent: *Jul. 1, 2025

(54) IMMUNOREACTANT CARRIER

(71) Applicant: LEMONEX INC., Seoul (KR)

(72) Inventor: Cheol Hee Won, Seoul (KR)

(73) Assignee: LEMONEX INC., Seoul (KR)

( * ) Notice: Subject to any disclaimer, the term of this patent is extended or adjusted under 35 U.S.C. 154(b) by 962 days.

This patent is subject to a terminal disclaimer.

(21) Appl. No.: 17/265,692

(22) PCT Filed: Jun. 3, 2019

(86) PCT No.: PCT/KR2019/006682
§ 371 (c)(1),
(2) Date: Feb. 3, 2021

(87) PCT Pub. No.: WO2020/032366
PCT Pub. Date: Feb. 13, 2020

(65) Prior Publication Data
US 2021/0177988 A1 Jun. 17, 2021

Related U.S. Application Data

(60) Provisional application No. 62/714,874, filed on Aug. 6, 2018.

(30) Foreign Application Priority Data
Jun. 3, 2019 (KR) .................. 10-2019-0065620

(51) Int. Cl.
*A61K 47/69* (2017.01)
*C07K 14/54* (2006.01)
(Continued)

(52) U.S. Cl.
CPC ...... *A61K 47/6923* (2017.08); *C07K 14/5434* (2013.01); *C07K 14/5437* (2013.01);
(Continued)

(58) Field of Classification Search
CPC .. A61K 47/6923; A61K 38/19; A61K 9/0019; A61K 9/5115; A61K 39/395;
(Continued)

(56) References Cited

U.S. PATENT DOCUMENTS 11,129,796 B2 * 9/2021 Won .................. A61K 38/465
11,530,132 B2 * 12/2022 Min .................... A61K 31/706
(Continued)

FOREIGN PATENT DOCUMENTS

JP    2017048180 A    3/2017
KR   10-2016-0011565 A   2/2016
(Continued)

OTHER PUBLICATIONS

Kwon, Dohyeong, et al. "Extra-large pore mesoporous silica nanoparticles for directing in vivo M2 macrophage polarization by delivering IL-4." Nano letters 17.5 (2017): 2747-2756. (Year: 2017).*

(Continued)

*Primary Examiner* — Frederick F Krass
*Assistant Examiner* — Lucy M Tien
(74) *Attorney, Agent, or Firm* — The PL Law Group, PLLC

(57) ABSTRACT

An immunoreactive substance carrier according to an embodiment of the present invention may stably deliver various immunoreactive substances including antibodies and/or cytokines, to a target site, thereby exhibiting excellent immunotherapeutic effects. Therefore, a composition including the immunoreactive substance carrier can be used for immunotherapy, thereby having excellent effects in the prevention or treatment of cancer or various immune diseases.

14 Claims, 46 Drawing Sheets

(51) Int. Cl.
C07K 14/55 (2006.01)
C07K 16/28 (2006.01)
(52) U.S. Cl.
CPC .......... *C07K 14/5443* (2013.01); *C07K 14/55* (2013.01); *C07K 16/2818* (2013.01); *C07K 16/2827* (2013.01)
(58) Field of Classification Search
CPC ............ A61K 47/6927; A61K 47/6929; A61K 9/143; A61K 9/1611; A61K 38/20; A61K 38/21; A61K 39/3955; C07K 14/5434; C07K 14/5437; C07K 14/5443; C07K 14/55; C07K 16/2818; C07K 16/2827; C07K 16/00; A61P 35/00; A61P 37/02
See application file for complete search history.

(56) References Cited

U.S. PATENT DOCUMENTS

| | | | | |
|---|---|---|---|---|
| 2011/0300186 | A1* | 12/2011 | Hellstrom | C07K 16/2809 424/277.1 |
| 2015/0272885 | A1* | 10/2015 | Ashley | A61K 49/0423 514/21.3 |
| 2017/0172923 | A1 | 6/2017 | Won | |

FOREIGN PATENT DOCUMENTS

| | | | |
|---|---|---|---|
| KR | 10-2017-0138861 | A | 12/2017 |
| KR | 10-2018-0091768 | A | 8/2018 |
| WO | WO 2013/129093 | A1 | 9/2013 |
| WO | WO 2014/058014 | A1 | 4/2014 |
| WO | WO 2016/039218 | A1 | 3/2016 |
| WO | WO 2019/022521 | A9 | 8/2019 |

OTHER PUBLICATIONS

He, Qianjun, et al. "An anticancer drug delivery system based on surfactant-templated mesoporous silica nanoparticles." Biomaterials 31.12 (2010): 3335-3346. (Year: 2010).*

Creative Diagnostics (Creative Diagnostics, Products. Basic Silica Particles. (Dec. 20, 2018). https://web.archive.org/web/20181220142512/https://www.cd-bioparticles.com/product/basic-silica-particles-list-194.html#expand). (Year: 2018).*

Kecht, Johann, Axel Schlossbauer, and Thomas Bein. "Selective functionalization of the outer and inner surfaces in mesoporous silica nanoparticles." Chemistry of Materials 20.23 (2008): 7207-7214. (Year: 2008).*

Office action issued on Mar. 1, 2022 from Japan Intellectual Property Office in a counterpart Japanese Patent Application No. 2021-506399 (all the cited references are listed in this IDS.).

Dohyeong Kwon et al, 'Extra-Large Pore Mesoporous Silica Nanoparticles for Directing in Vivo M2 Macrophage Polarization by Delivering IL-4', Nano Letters, 2017, pp. 2747-2756, vol. 17, No. 5.

Yixian Zhou et al. 'Mesoporous silica nanoparticles for drug and gene delivery', Acta Pharmaceutica Sinica B, 2018, pp. 165-177, vol. 8, Issue 2.

European Search Report for EP 19846510.6 issued on Jun. 3, 2022 from European patent office in a counterpart European patent application(all the cited references are listed in this IDS).

Jeong Moonkyoung et al: "Porous Materials for Immune Modulation", Open Material Sciences, vol. 4, No. 1, Apr. 21, 2018 (Apr. 21, 2018), pp. 1-14, XP055909291, DOI: 10.1515/oms-2018-0001.

Office action issued on Aug. 30, 2022 from Japan Intellectual Property Office in a counterpart Japanese Patent Application No. 2021-506399 (all the cited references are listed in this IDS.) (English translation is also submitted herewith.).

International Search Report for PCT/KR2019/006682 mailed on Sep. 10, 2019.

Yixian Zhou et al., "Mesoporous silica nanoparticles for drug and gene delivery", Acta Pharmaceutica Sinica B, vol. 8(2), pp. 165-177, 2018.

Croissant JG, "Degradability and Clearance of Silicon, Organosilica, Silsesquioxane, Silica Mixed Oxide, and Mesoporous Silica Nanoparticles.", Advanced Material, vol. 29(9), Article No. 1604634, pp. 1-51, 2017.

Nikola Ž. Knežević, "Large pore mesoporous silica nanomaterials for application in delivery of biomolecules", Nanoscale, vol. 7, pp. 2199-2209, 2015.

Christopher R. Steven, "Bioinspired silica as drug delivery systems and their biocompatibility", Journal of Materials Chemistry B, vol. 2, pp. 5028-5042, 2014.

* cited by examiner $t_{50\%}$ = about 2.5 days

○ Vehicle
▼ IL-2 (0.5 mg/kg, bid)
● BALLkine-2 (1 mg/kg)

Tumor (B16F10 cells) bearing mouse
(tumor volume around 100 mm$^2$)

IMMUNOREACTANT CARRIER

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/006682, filed on Jun. 3, 2019, which claims priority to the benefit of U.S. Patent Application No. 62/714,874 filed in the US Patent Office on Aug. 6, 2018 and Korean Patent Application No. 10-2019-0065620 filed in the Korean Intellectual Property Office on Jun. 3, 2019, the entire contents of which are incorporated herein by reference.

BACKGROUND

Technical Field

The present invention relates to an immunoreactive substance carrier having excellent immunotherapeutic effects by delivering an immunoreactive substance stably to a target site.

Background Art

A drug delivery system refers to a medical technique that can efficiently deliver a required amount of drugs, such as proteins, nucleic acids or other small molecules by minimizing side effects while maximizing efficacy and effects of existing drugs. This technique capable of saving costs and time required for development of new drugs has recently become one of advanced techniques that create a new added value in the pharmaceutical industry, in combination with nanotechnique. Since the late 1980s, in particular, companies in the technically advanced countries such as United States, Japan, etc. have made every effort to develop drug delivery systems along with the development of new drugs.

To date, viral genes, recombinant proteins, liposomes, cationic polymers, and various types of nanoparticles and nanomaterials have been used for drug delivery into animal cells. However, many cationic liposomes and cationic polymers have been found to be unsuitable due to their high toxicity to cells for clinical applications. Further, a method of chemically modifying a main chain of the nucleic acid has been attempted for stable cell membrane penetration of the nucleic acid. However, such a method is not suitable for clinical applications because it is expensive, time consuming, and requires labor intensive processes. As a significant attempt, drug delivery systems (DDSs) utilizing various types of nanoparticles, including quantum dots, magnetic particles or gold nanoparticles, have been developed. However, these particles have a disadvantage in that they are toxic to cells, have a structure through which biopolymers such as nucleic acids are not easily introduced, and also have low efficiency of introduction into the cells.

Efficient delivery systems are needed for studying functions of bioactive substances in vivo or for intracellular delivery. However, the development of a universal delivery system capable of delivering a wide range of bioactive substances, a system capable of accommodating and delivering a large amount of drugs, and a system for releasing drugs in a sustained manner are still in shortage.

SUMMARY

An object of the present invention is to provide an immunoreactive substance carrier with excellent immunotherapeutic effects that stably delivers various immunoreactive substances including antibodies and cytokines to a target site.

To achieve the above objects, the following technical solutions are adopted in the present invention.

1. An immunoreactive substance carrier, including: porous silica particle which carry an antibody or cytokine, wherein the porous silica particles are prepared by: reacting silica particles having pores with a pore diameter of less than 5 nm with a swelling agent at 120 to 180° C. for 24 to 96 hours to expand the pores with a pore diameter of less than 5 nm; and calcining the silica particles having expanded pores at a temperature of 400° C. or higher for at least 3 hours, an average diameter of the porous silica particles ranges from 150 to 1000 nm, a BET surface area ranges from 200 to 700 m$^2$/g, and a volume per g ranges from 0.7 to 2.2 ml, and the porous silica particles are characterized in that t, at which an absorbance ratio in the following Equation 1 becomes ½, is 24 or more, $$A_t/A_0 \qquad \text{[Equation 1]}$$

wherein $A_0$ is absorbance of the porous silica particles measured by placing 5 ml of suspension containing 1 mg/ml of porous silica particles in a cylindrical permeable membrane having pores with a pore diameter of 50 kDa, 15 ml of the same solvent as the suspension comes into contact with outside of the permeable membrane, and the inside/outside of the permeable membrane is horizontally stirred at 60 rpm and 37° C., pH of the suspension is 7.4, and $A_t$ indicates absorbance of the porous silica particle measured after lapse of "t" hours since $A_0$ was measured).

2. The immunoreactive substance carrier according to the above 1, wherein the antibody is an antibody specifically bound to interleukins or interferon protein.

3. The immunoreactive substance carrier according to the above 1, wherein the antibody is IgG or an antibody specifically bound to at least one protein selected from the group consisting of PD-1, CTLA-4, TIM-3, BTLA, VISTA, LAG-3, PD-L1, PD-L2, B7-H3, B7-H4, CD28, CD27, CD137, HVEM, GITR, VEGFR, VEGF, EGFR, EGF, IL-1, IL-6, IL-23, TGF-beta, CTGF, TSLP, TNF-alpha, Notch and OX40.

4. The immunoreactive substance carrier according to the above 1, wherein the antibody is an antibody specifically bound to at least one selected from the group consisting of PD-1, PD-L1 and CTLA-4.

5. The immunoreactive substance carrier according to the above 1, wherein the cytokine is interleukins or interferons.

6. The immunoreactive substance carrier according to the above 1, wherein the cytokine is at least one selected from the group consisting of IL-7, IL-10, IL-12, IL-13, IL-15, IL-21, IL-23, IL-24, IL-27, G-CSF, GM-CSF, HGF, EGF, VEGF, LTF, TGF-β and IL-2.

7. The immunoreactive substance carrier according to the above 1, wherein the cytokine is at least one selected from the group consisting of IL-2, IL-12, IL-15, IL-21, IL-24 and IL-13.

8. The immunoreactive substance carrier according to the above 1, wherein the porous silica particles are charged at neutral pH on an outer surface thereof or an inside of the pores.

9. The immunoreactive substance carrier according to the above 1, wherein the porous silica particles have hydrophilic or hydrophobic functional groups on the outer surface thereof or an inside the pores.
10. The immunoreactive substance carrier according to the above 1, wherein the carrier includes the porous silica particles loaded with the antibody and the porous silica particles loaded with the cytokine.
11. An immunotherapeutic composition, including the immunoreactive substance carrier according to any one of the above 1 to 10.
12. A pharmaceutical composition for prevention or treatment of cancers or immune diseases, including the immunoreactive substance carrier according to any one of claims 1 to 10.

The immunoreactive substance carrier of the present invention may stably deliver various immunoreactive substances, including antibodies and cytokines, to a target site, thereby exhibiting excellent immunotherapeutic effects.

DDV (Degradable Delivery Vehicle) is the particles according to an embodiment, wherein the number in parenthesis means the diameter of the particle and the number of subscripts means the pore diameter. For example, DDV(200)$_{10}$ refers to a particle having a particle diameter (that is, particle size) of 200 nm and a pore diameter of 10 nm according to an embodiment.

Figure 6:
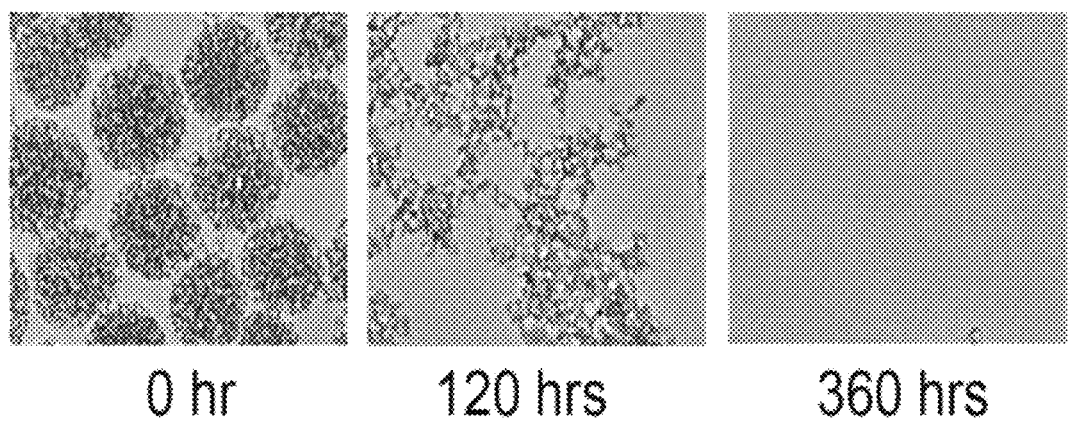

FIG. 6 is micrographs of the porous silica particles for each pore diameter according to one embodiment of the present invention.

Figure 7:
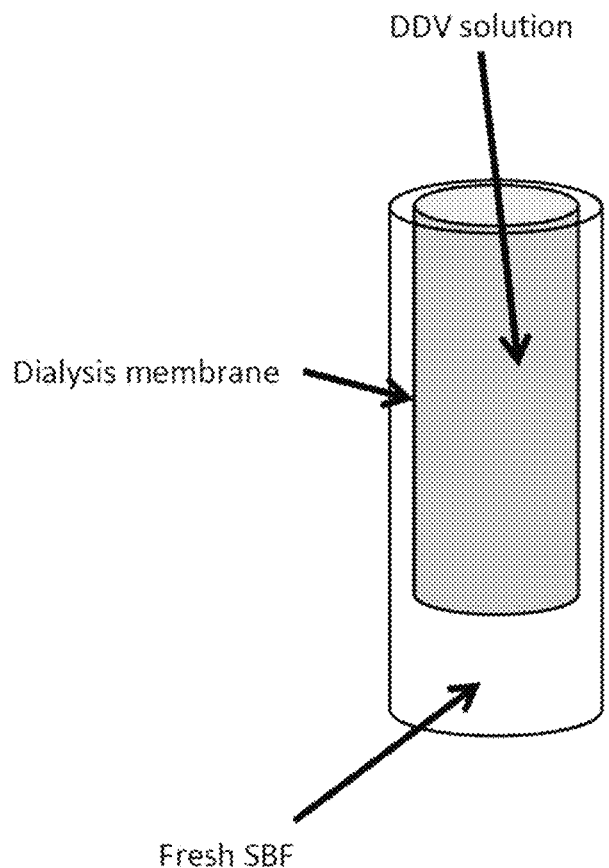

FIG. 7 is micrographs to identify biodegradability of the porous silica particles according to one embodiment of the present invention.

Figure 8:
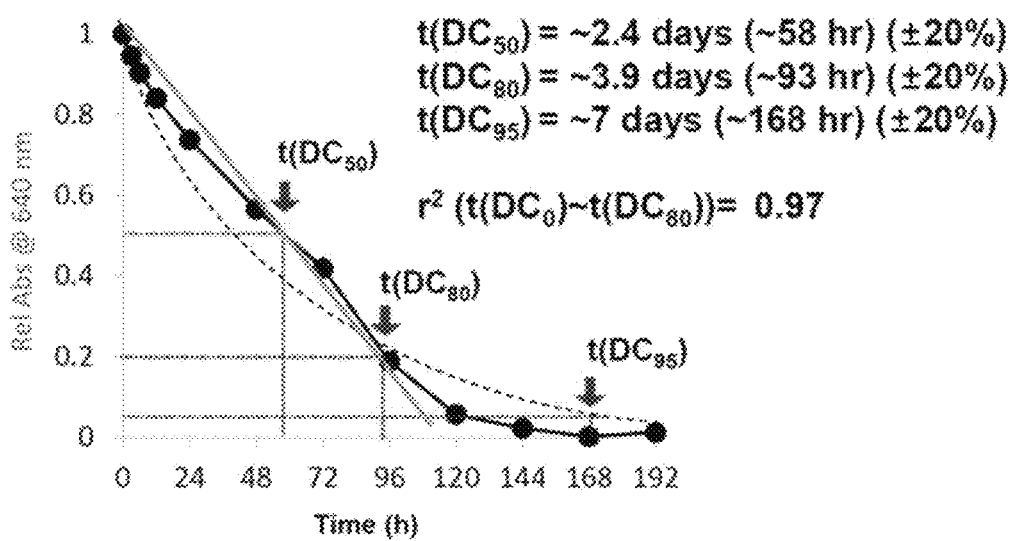

FIG. 8 is a view illustrating a tube having a cylindrical permeable membrane according to one illustrative example.

Figure 9:
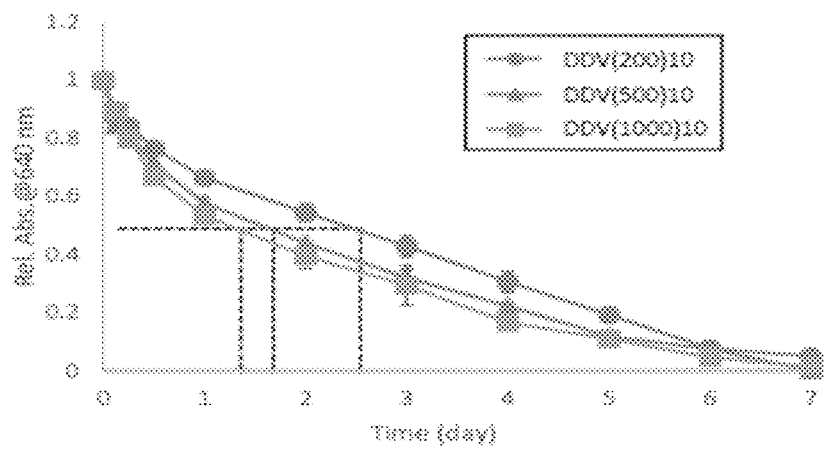

FIG. 9 is a graph illustrating results of decreasing absorbance of the porous silica particles over time according to one embodiment of the present invention.

Figure 10:
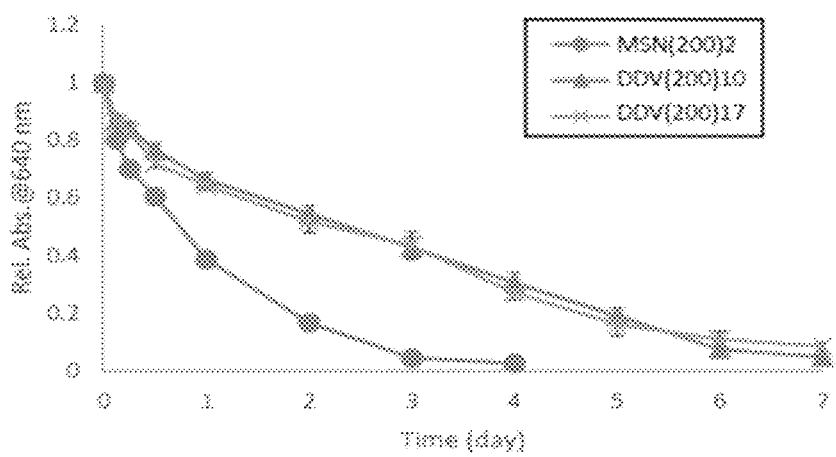

FIG. 10 is diagrams illustrating results of decreasing absorbance of the porous silica particles for each particle size over time according to one embodiment of the present invention.

Figure 11:
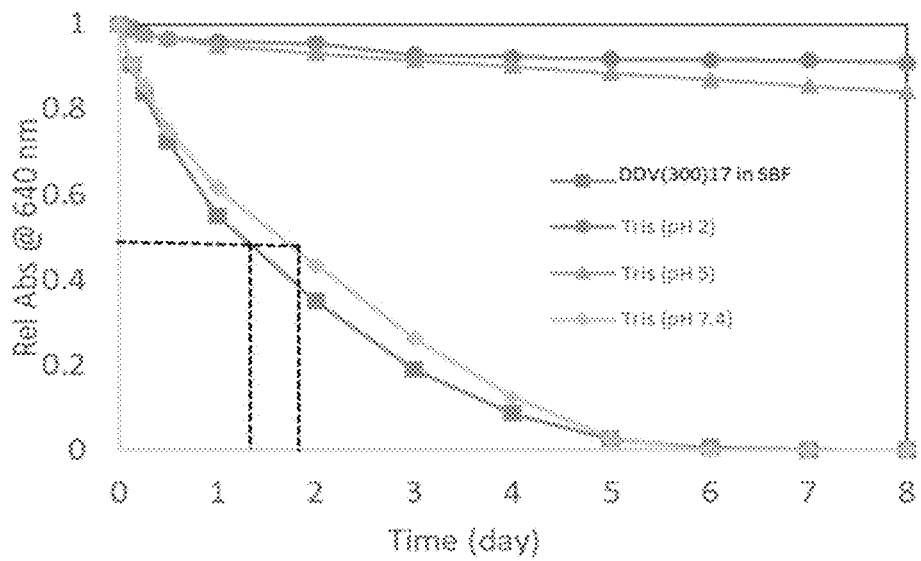

FIG. 11 is diagrams illustrating results of decreasing absorbance of the porous silica particles for each pore diameter over time according to one embodiment of the present invention.

Figure 12:
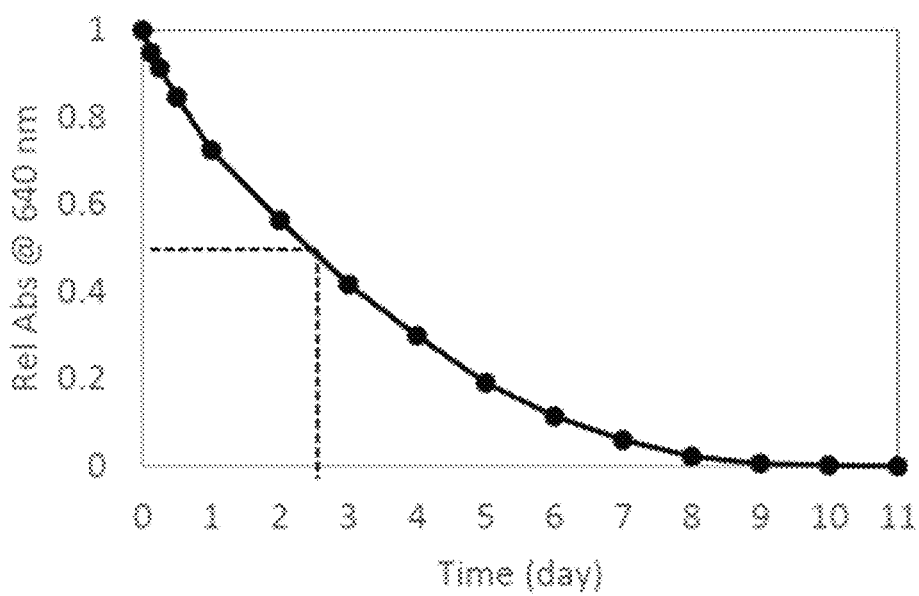

FIG. 12 is a graph illustrating results of decreasing absorbance of the porous silica particles for each pH of the environment over time according to one embodiment of the present invention.

Figure 13:
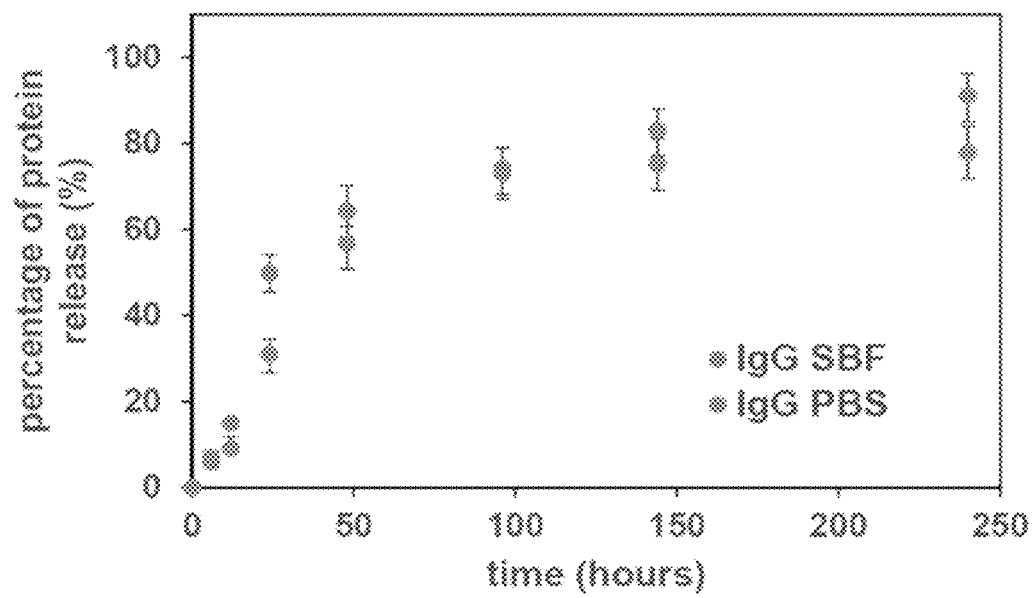
Figure 14:
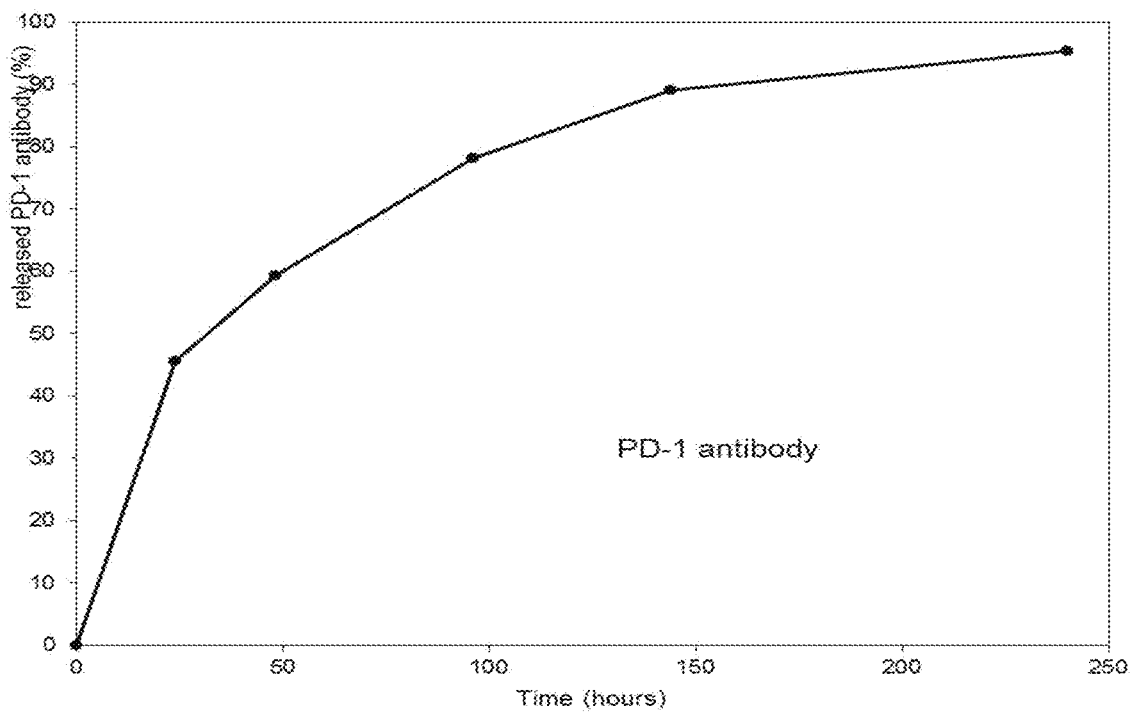
Figure 15:
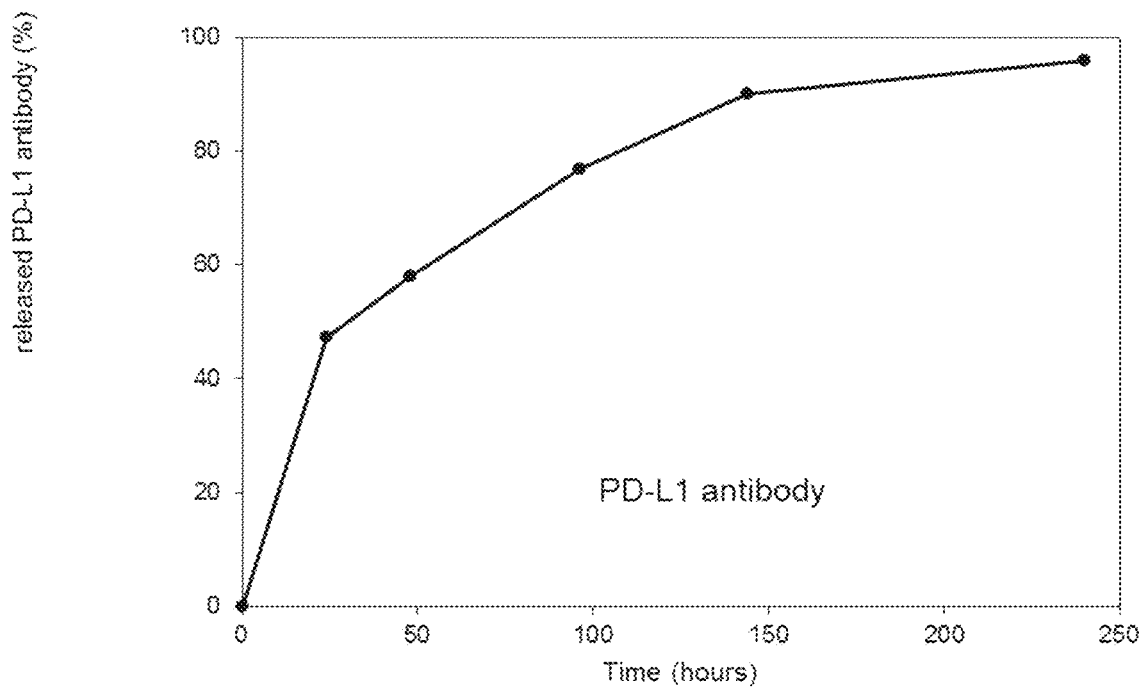

FIGS. 13 to 15 are diagrams illustrating cumulative amounts released after loading IgG, PD-1, and PD-L1 antibodies on porous silica particles, respectively.

Figure 16:
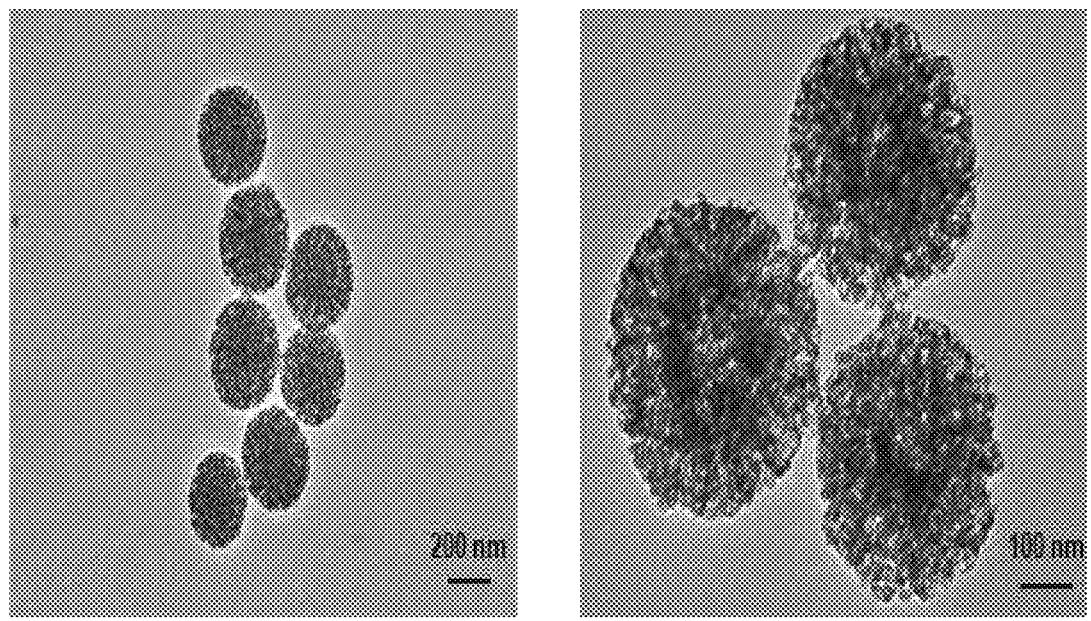
Figure 17:
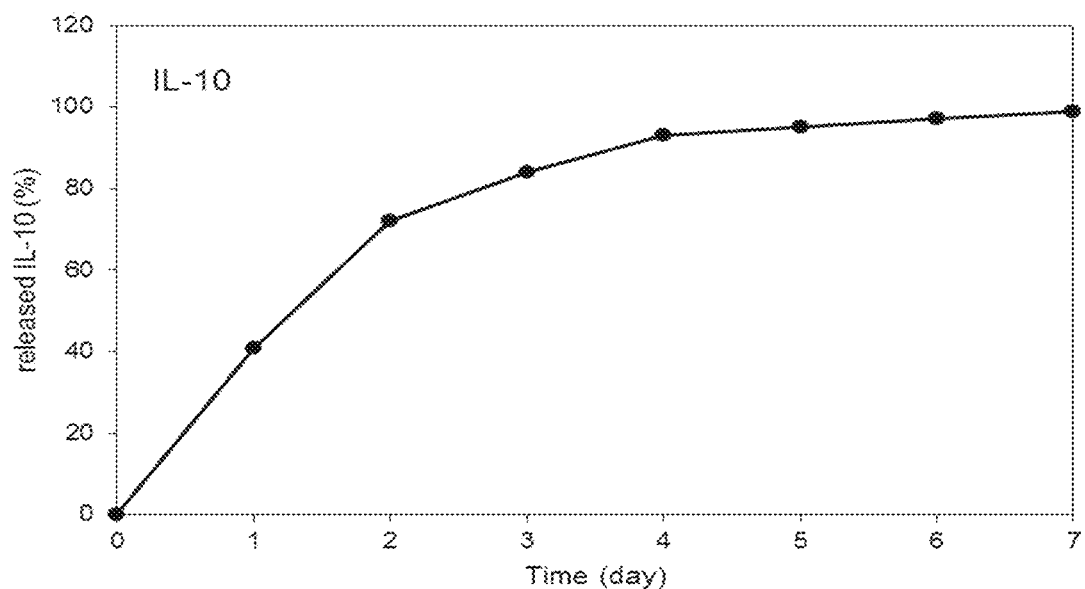
Figure 18:
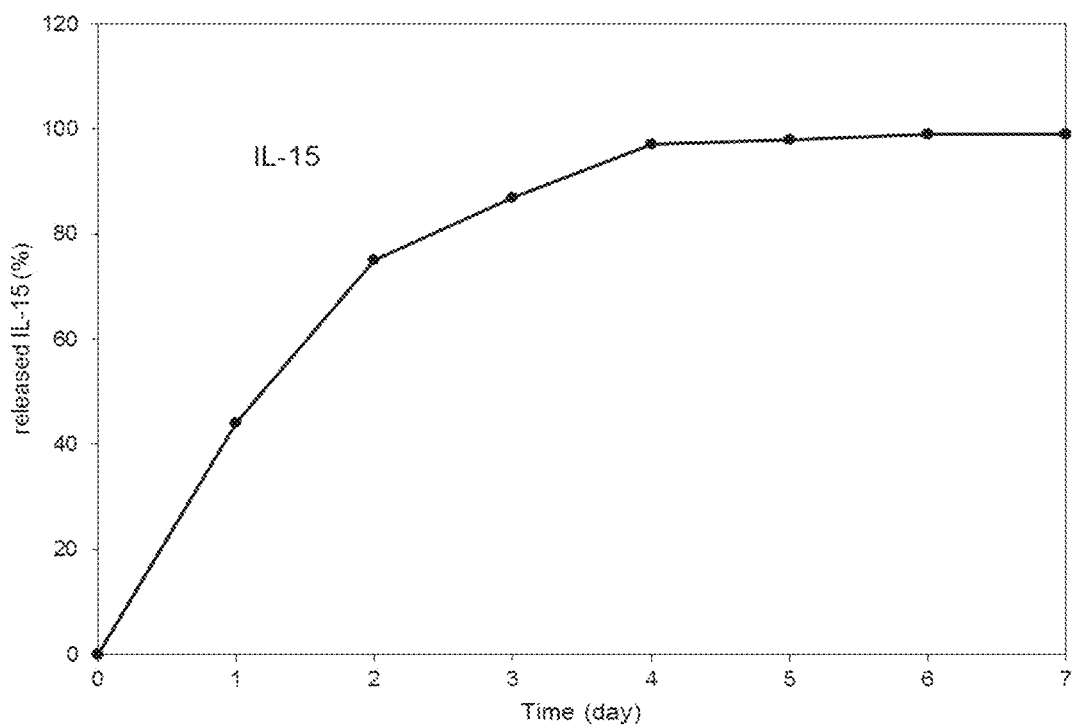
Figure 19:
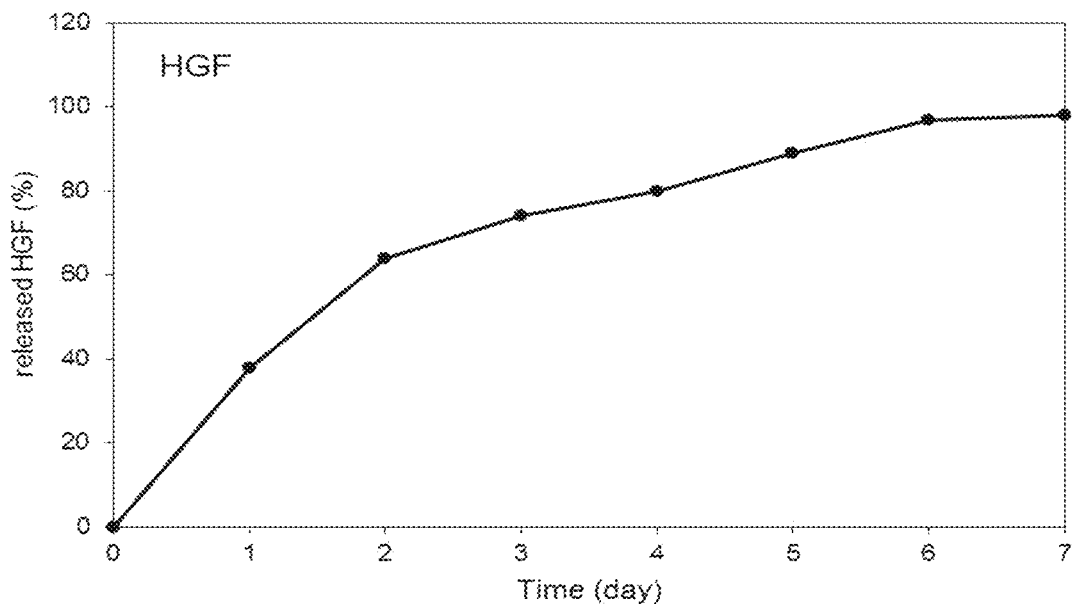
Figure 20:
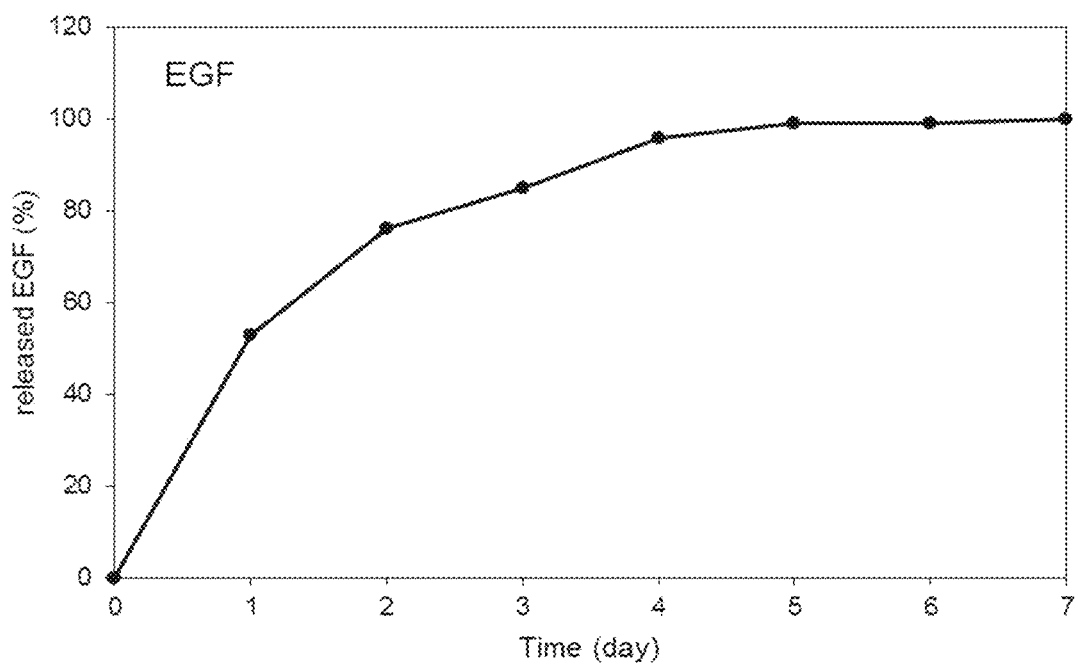
Figure 21:
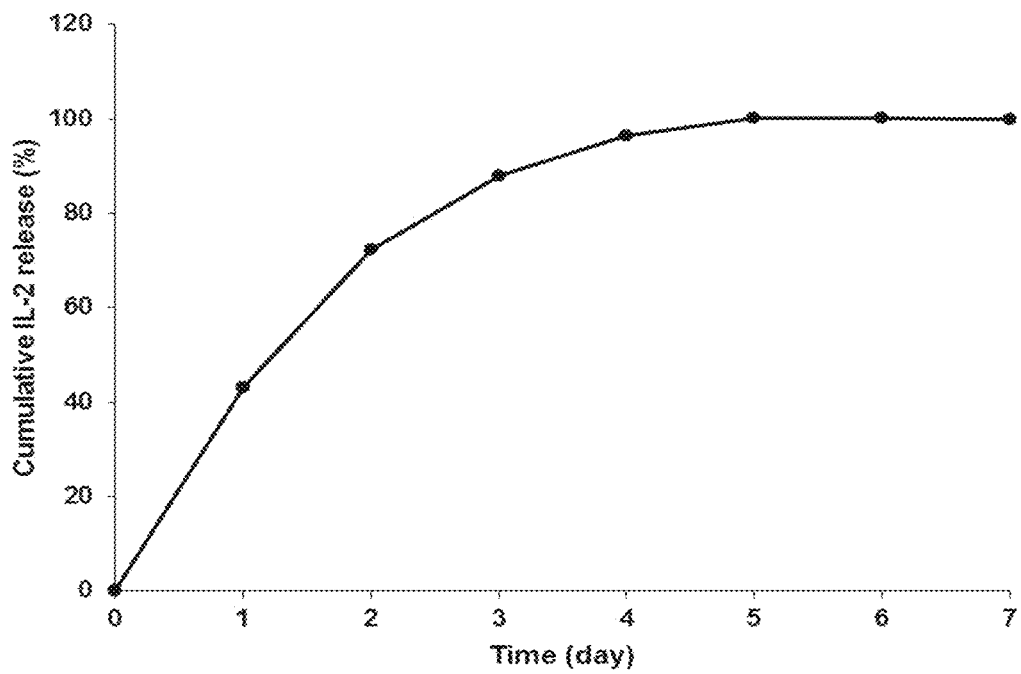
Figure 22:
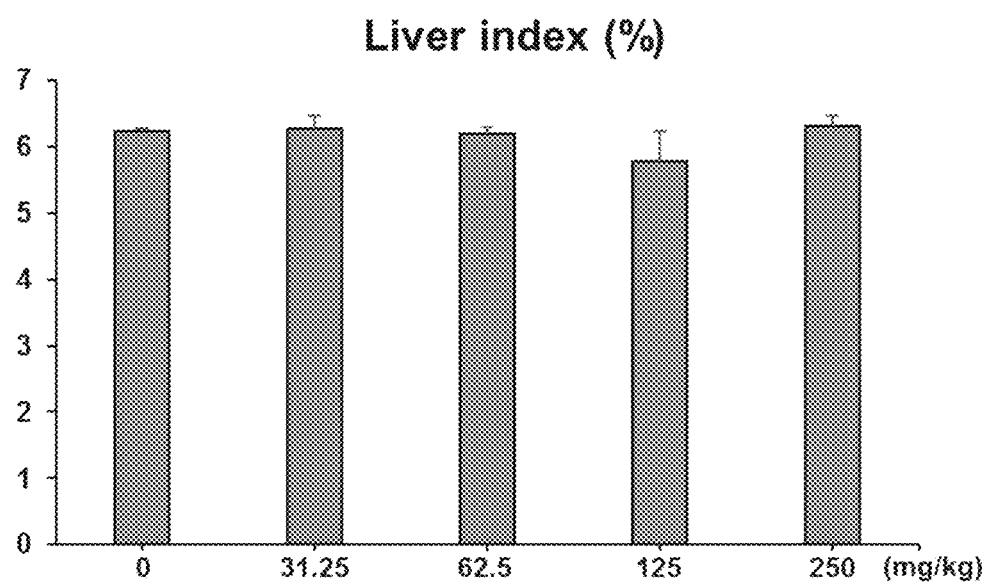
Figure 23:
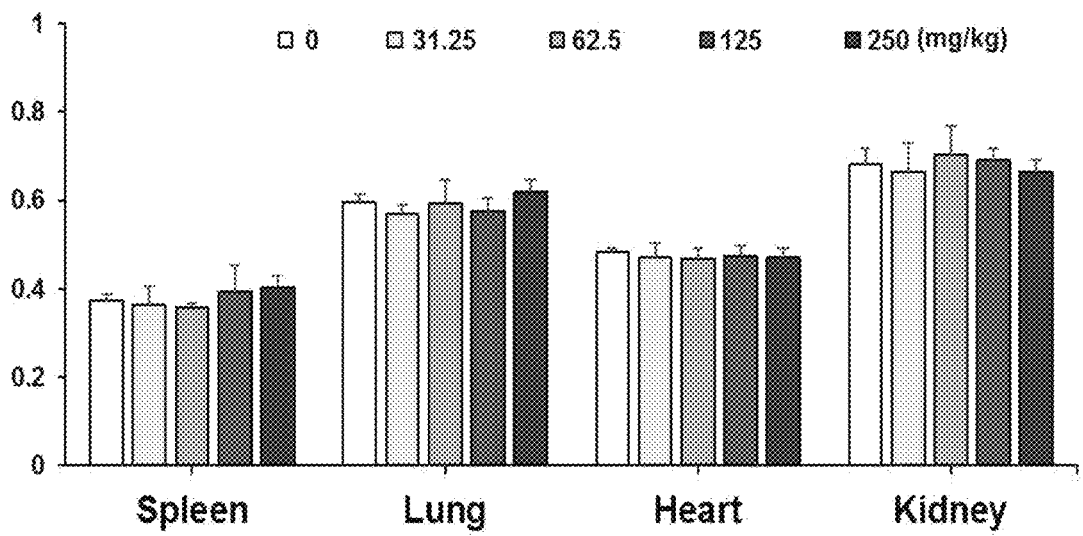
Figure 24:
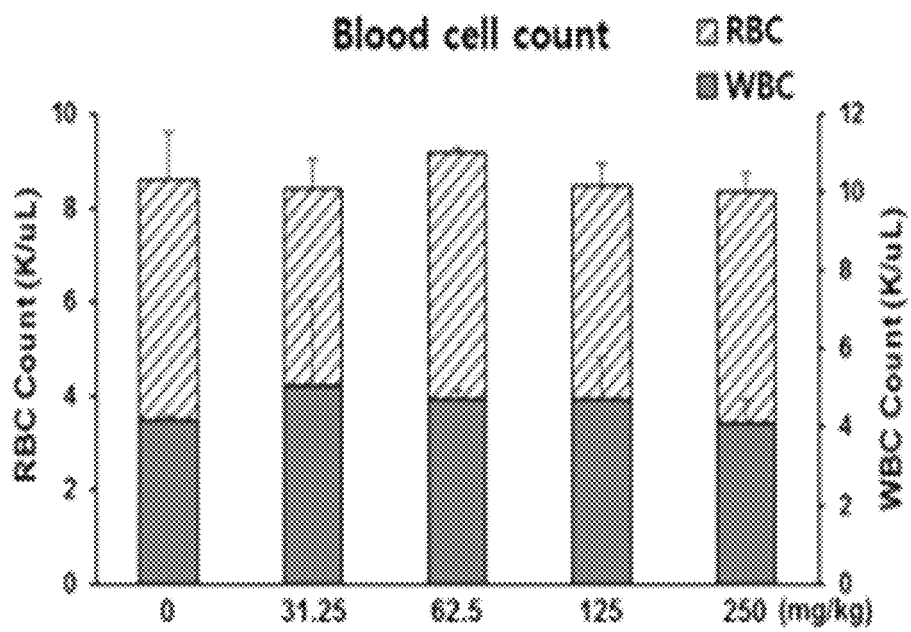
Figure 25:
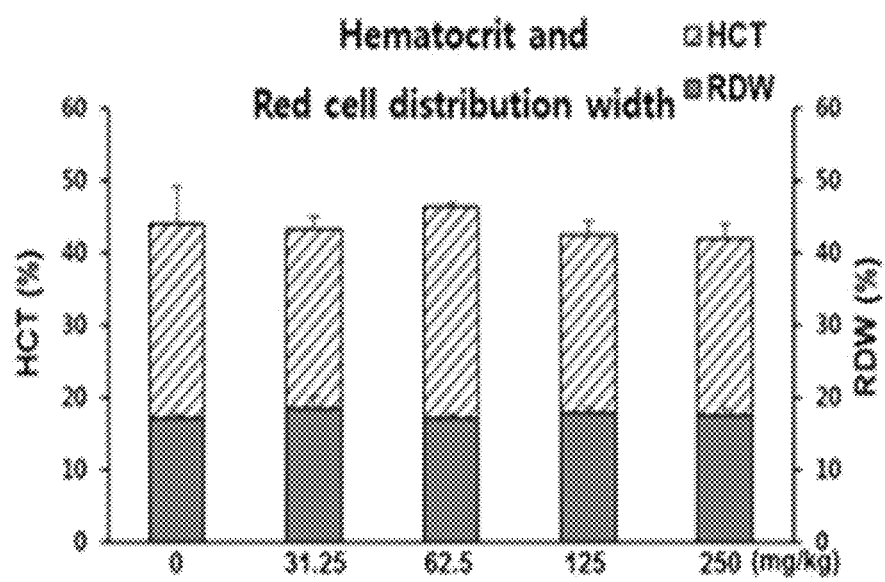
Figure 26:
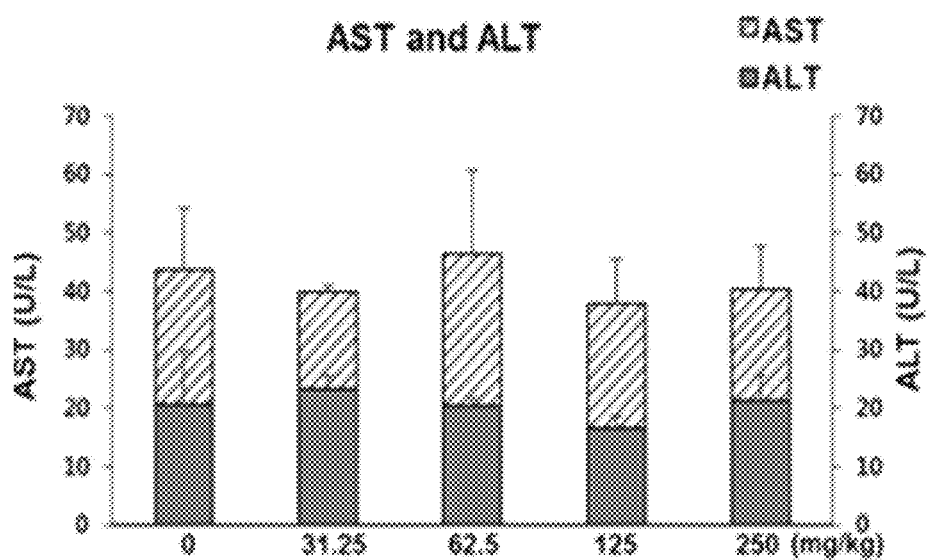
Figure 27:
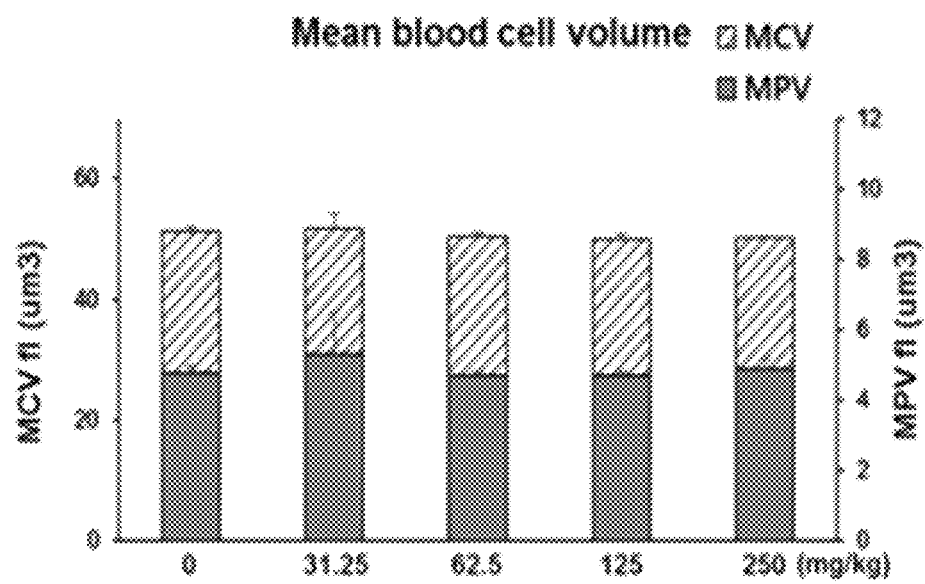
Figure 28:
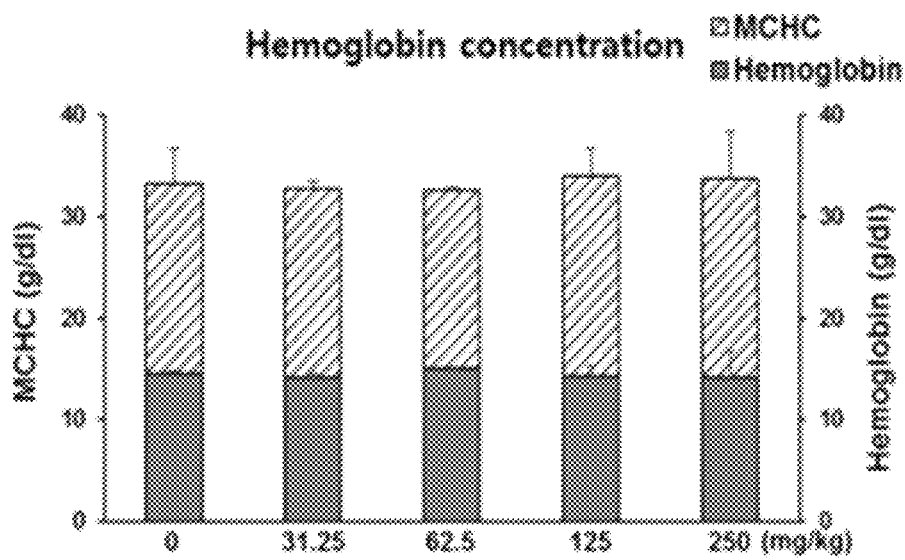
Figure 29:
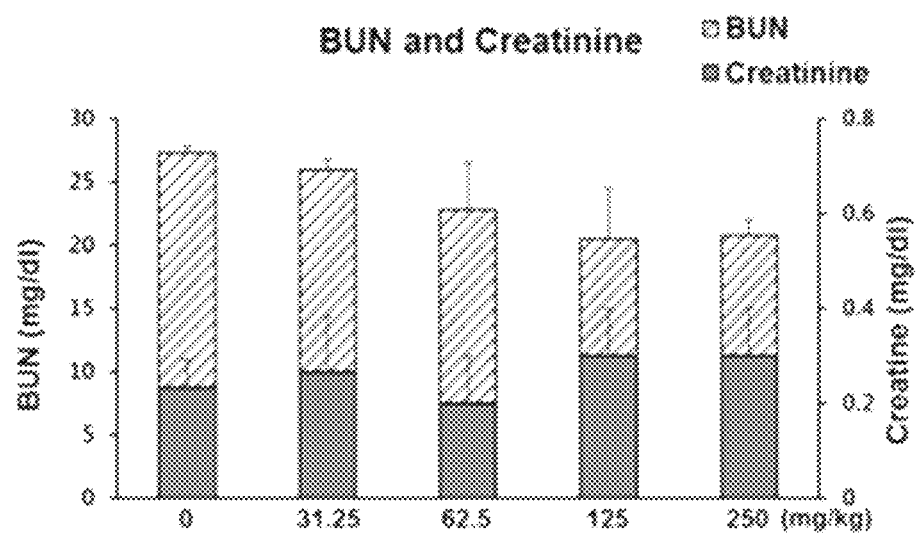
Figure 30:
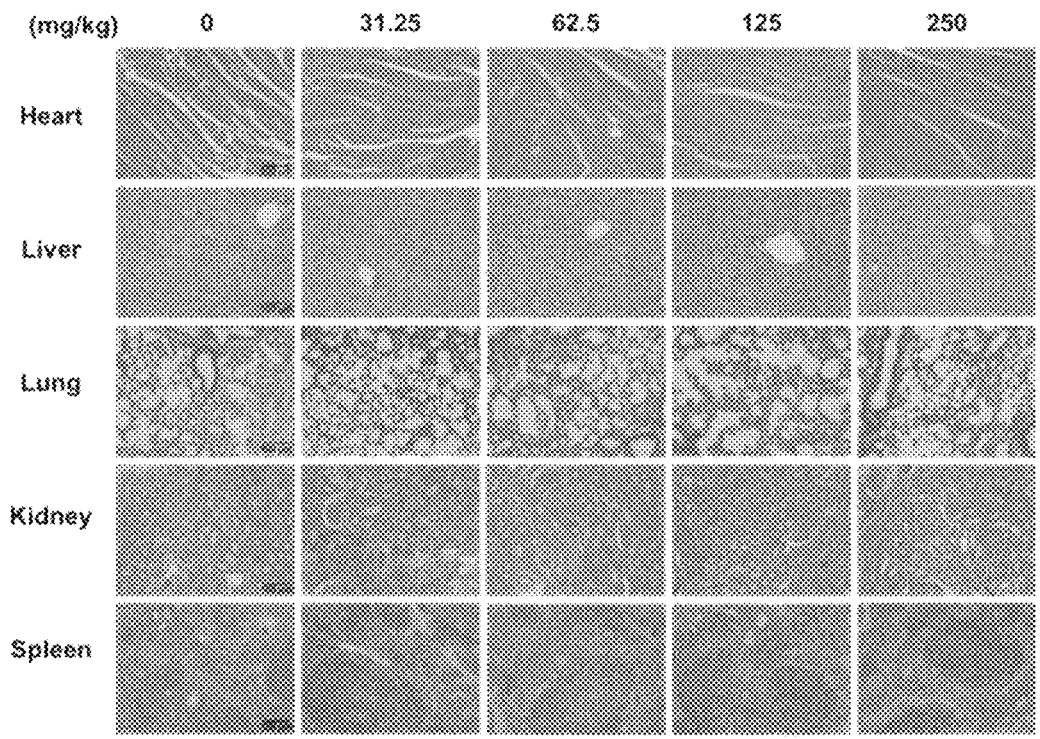
Figure 31:
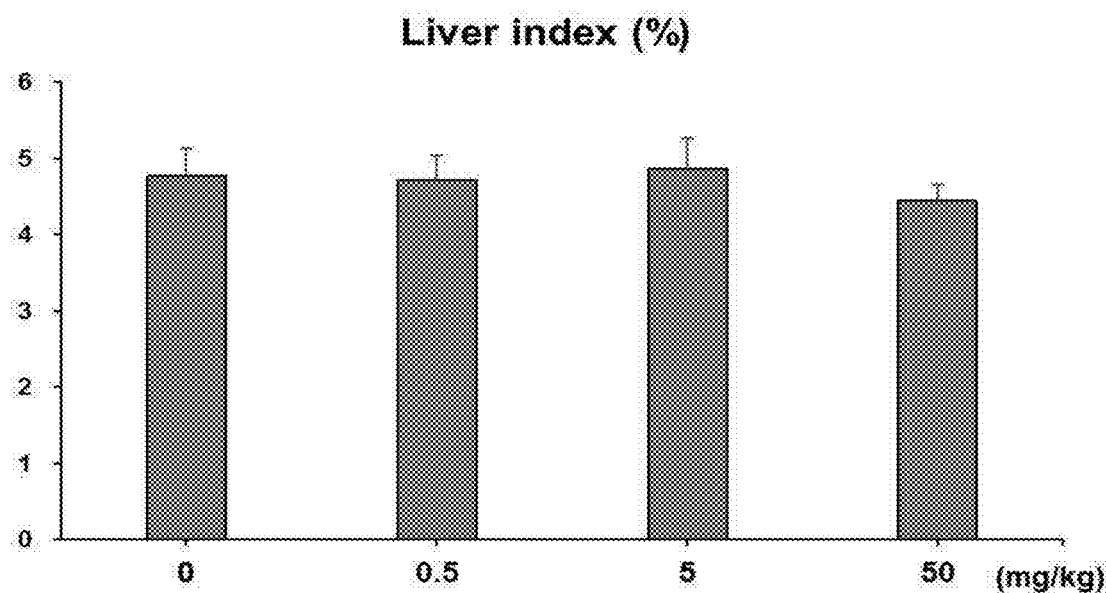
Figure 32:
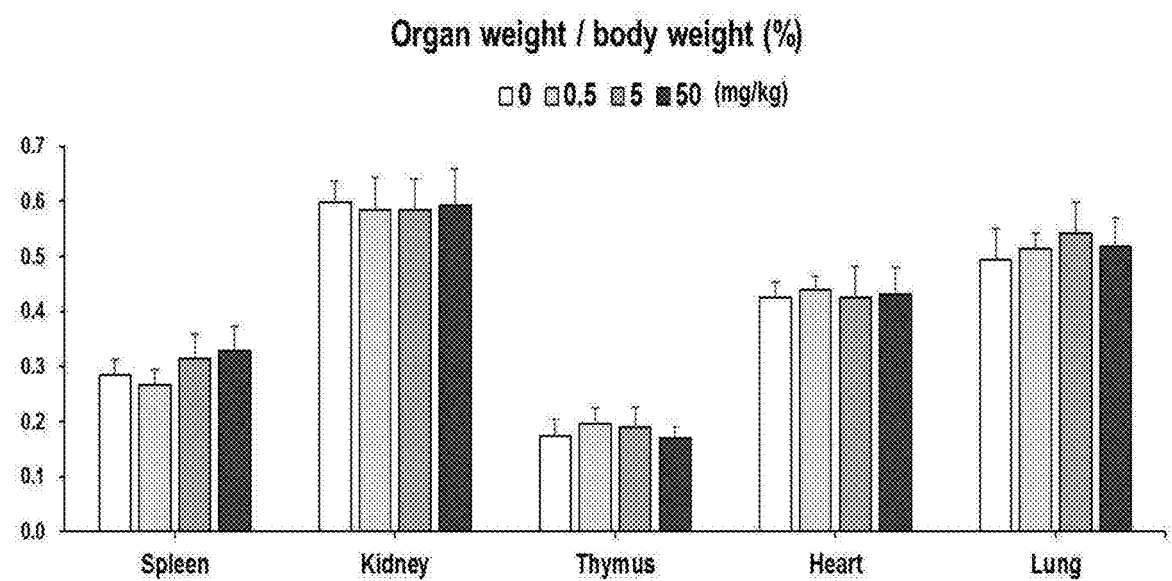
Figure 33:
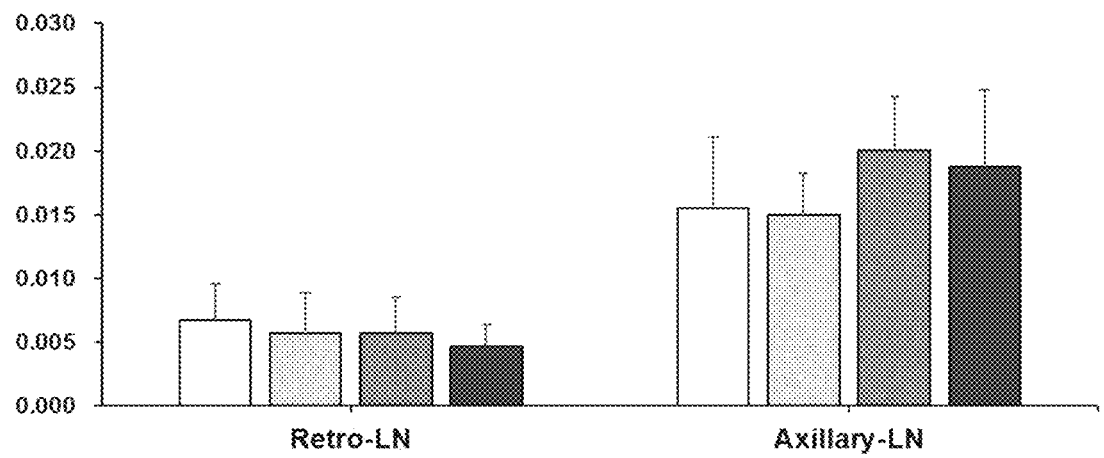

FIG. 16 is TEM images illustrating the porous silica particles used to carry IL-2 cytokines.

FIGS. 17 to 21 are diagrams illustrating cumulative amounts released after loading IL-10, IL-15, HGF, EGF and IL-2 on porous silica particles, respectively.

FIGS. 22 to 43 are diagrams illustrating results of identifying toxicity of the porous silica particles according to the present invention.

Figure 44:
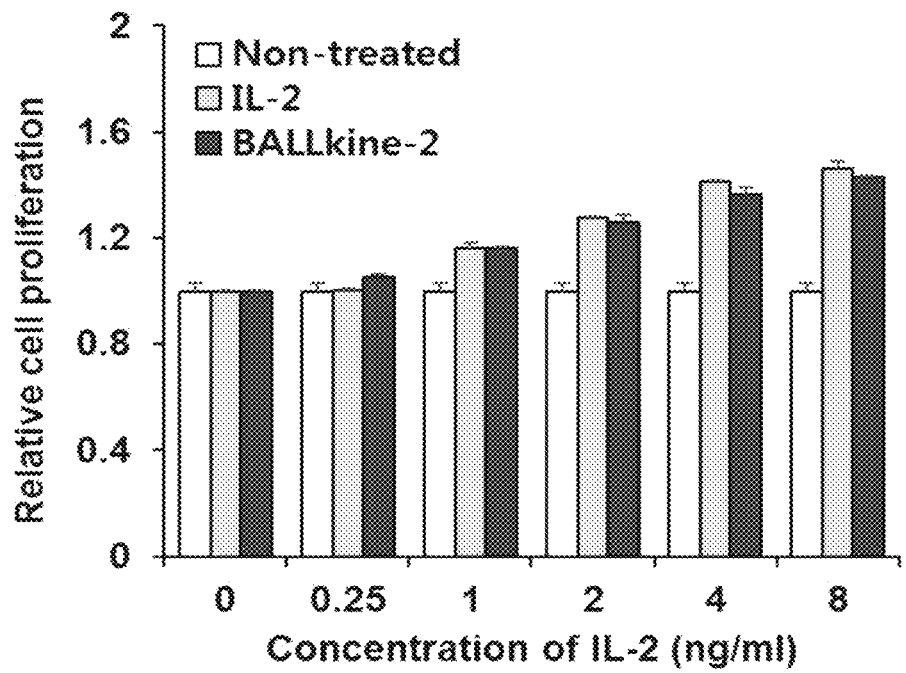
Figure 45:
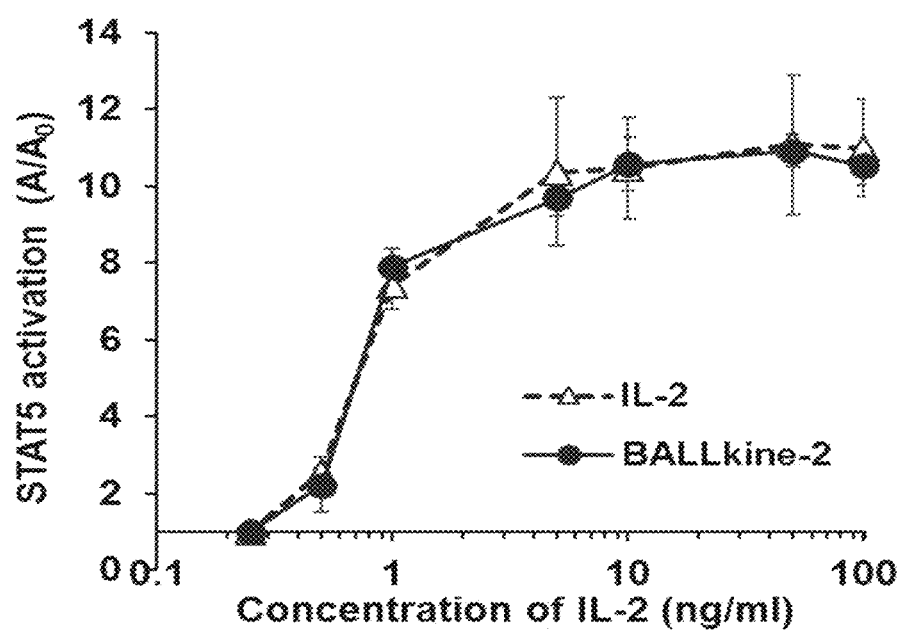

FIGS. 44 and 45 are diagrams illustrating results of identifying biological activity of the immunoreactive substance supported on the porous silica particles.

Figure 46:
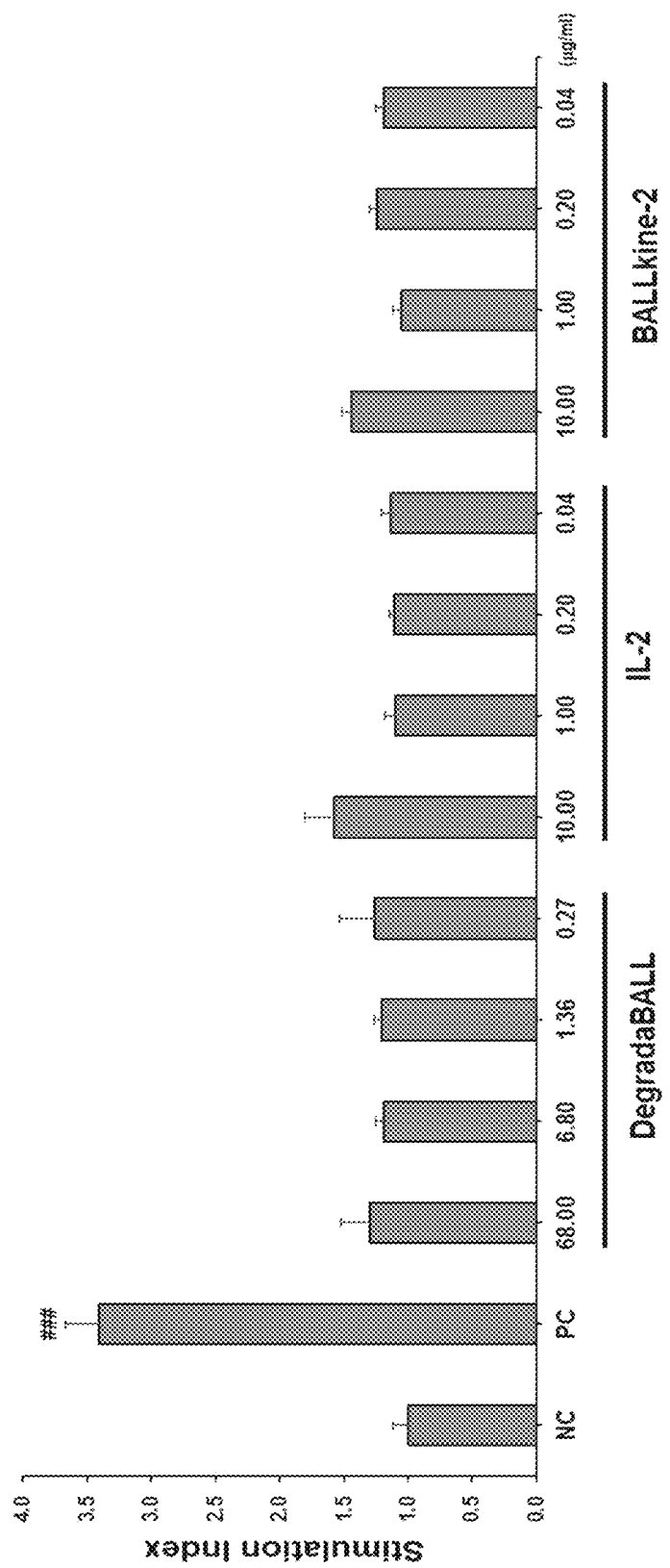

FIG. 46 is a graph illustrating results of identifying hypersensitivity in response by the carrier of the present invention.

FIGS. 47 to 55 are diagrams illustrating identification of stable delivery and targeting property of the antibody or cytokine supported on the carrier of the present invention.

FIGS. 56 to 82 are diagrams illustrating results of identifying cancer immunotherapeutic efficacy of the carrier according to the present invention.

FIGS. 83 to 92 are diagrams illustrating results of identifying reduction in side effects (VLS or CLS) of the carrier according to the present invention carrier.

DETAILED DESCRIPTION

Hereinafter, the present invention will be described in detail.

The present invention provides an immunoreactive substance carrier, including porous silica particles which carry an antibody or cytokine.

Specifically, the cytokine may be interleukins or interferon.

The cytokine may be at least one selected from the group consisting of IL-7, IL-10, IL-12, IL-13, IL-15, IL-21, IL-23, IL-24, IL-27, G-CSF, GM-CSF, HGF, EGF, VEGF, LTF, TGF-β, IL-2, A2M, ABI3BP, acidic fibroblast growth factor, ACVRIB, ADAM17, ADAMTS6, ADMLX, aFGF, AGPATI, AGPAT2, AIF1, AIMP1, AKR1C1, AKT1S1, allograft-inflammatory factor-1, amac-1, AMH, ANGPTL2, ANGPTL3, ANKFN1, ANKRD1, ankyrin repeat and SOCS box-containing protein 3 isoform a variant, ankyrin repeat domain-containing SOCS box protein ASB11, ankyrin repeat domain-containing SOCS box protein Asb-13, ankyrin repeat domain-containing SOCS box protein Asb-14, ankyrin repeat domain-containing SOCS box protein Asb-15, ankyrin repeat-containing protein ASB-2, ankyrin repeat-containing SOCS box protein 7, ANOS1, Apo-2 ligand, APOC1, ARHGAP10, ASB1, ASB-1 protein, ASB10, ASB-10, ASB11, ASB12, ASB13, ASB14, ASB15, ASB16, ASB17, ASB18, ASB2, ASB-2, ASB3, ASB-3 protein, ASB4, ASB-4 protein, ASB5, ASB6, ASB7, ASB8, ASB9, ASTN2, ATP10A, ATP1A1, ATP8A1, AXL, B219/OB receptor isoform HuB219.1 precursor, B219/OB receptor isoform HuB219.2 precursor, B219/OB receptor isoform HuB219.3 precursor, BATF, BCL2A1, BCL3, BCO2, BIG-2, BMP6, BOC, BTNL2, byk, C10orf99, C11orf40, C17, C17orf99, C19orf66, CIGALTICI, ClQTNF4, C22orf39, C2orf83, C3orf39, C6 beta-chemokine, C6orfl20, C8orf44-SGK3, CALL, CAMKMT, CARD14, cardiotrophin-like cytokine CLC, CASP1, cathepsin X, CBLB, CBLN4, CCDCl34, CCDC86, CCL1, CCL11, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL3L1, CCL3L3, CCL4, CCL4L, CCL4L1, CCL4L2, CCL5, CCL7, CCL8, CCR4, CCR8, CD200R1, CD274, CD28, CD300LB, CD34, CD36, CD3D, CD40LG, CD53, CD70, CD74, CD74-ROS1_C6,R32, CD80, CD83, CD84, CD86, CDO, CDON, CEBPD, CERI, CFC1, chemokine (C—C motif) ligand 13, chemokine (C—C motif) ligand 3, CHL1, CHUK, CIAPINI, ciliary neurotrophic factor receptor, CIP29, CIS2, CIS3, CIS4, CISH, CISH6, CITED2, CKId, CKIe, CKLF, CKLF1, CKLFSF1, CLC, CLCF1, CLEC1IA, CLECIB, CLEC2D, CLF-1, CLNK, c-mer, c-mpl-K, c-mpl-P, CMYA5, CNAIP, CNTF, CNTFR, CNTN1, CNTN2, CNTN3, CNTN4, CNTN5, CNTN6, CNTNAP4, CNTRL, Col VII, COL12A1, COL14A1, COL20A1, COL28A1, COL7A1, collagen VII, colony stimulating factor 2 receptor alpha subunit splice variant, colony stimulating factor 3 receptor isoform c precursor variant, CPEB 4 variant, CPEB4, CR6, CREME9, CRF2/12, CRIP2, CRL1, CRL2, CRL3, CRLF1, CRLF2, CRLF3, CRNDE, CRP, CRTAM, CS box-containing WD protein, CSA2, CSBP1, CSBP2, CSF1, CSF1R, CSF2, CSF2RA, CSF2RB, CSF3, CSF3R, CSN1S1, CTF1, CTLA4, CTLA8, CTSG, CUA001, CX3CL1, CXCL10, CXCL11, CXCL12, CXCL13, CXCL14, CXCL16, CXCL3, CXCL5, CXCL6, CXCL8, CXCL9, CXCR2, CXCR3, CXCR5, CXXC5, cyclon, CYP4F3, CYTIP, CYTL1, cytokine CX2 precursor, cytokine receptor CRL2 precursor, cytokine receptor-like factor 2 variant, cytokine SDF-1-beta, cytokine type 1 receptor CRLP-1 precursor, cytokine-inducible inhibitor of signaling type 1b, cytokine-inducible SH2-containing protein, cytokine-like nuclear factor n-pac, cytokine-like nuclear factor n-pac-like protein, cytokine-like protein 2-21, cytokine-like protein EF-7, CYTOR4, cytotoxic lymphocyte maturation factor 40 kDa subunit, DAGLA, DCC, DCSTAMP, DDT, DEFB103B, delta 4-delta 7/11 truncated prolactin receptor, delta 4-SF1b truncated prolactin receptor, dendritic cell associated lectin 2, density enhanced phosphatase-1, DHX58, DIP2C, DNAH3, DNAH9, Down syndrome cell adhesion molecule isoform CHD2-42 precursor variant, DRT, DSCAM, DSCAM2, DSCAML1, DTK, DTL, DUB3, DVL2, EBJ3, ECK, EDIL3, eEF1A2 binding protein, EFNA5, EGFLAM, EGR4, ELAC1, ELAVL1, ELAVL3, ELP2, endothelial-monocyte activating polypeptide II, EOMES, eotaxin precursor, EPGN, EPHA1, EPHA10, EPHA2, EPHA3, EPHA4, EPHA5, EPHA6, EPHA7, EPHA8, EPHB1, EPHB2, EPHB2 variant protein, EPHB3, EPHB4, EPHB6, EphB6 variant protein, ephrin receptor EphA5 isoform a variant, ephrin receptor EphA7 variant, ephrin receptor EphB4 precursor variant, EPO, EPOR, ERK, ESOP1, FABP5, factor for adipocyte differentiation 104 variant, fad104, FAM19A4, FAM213A, FAM3A, FAM3B, FAM3C, FAM3D, FANK1, FBRS, FCAR, FCER1A, FCER1G, FCGR2C, FCN3, FES, FGF19, FGF9, FGF-9, fibronectin, Fibronectin 1 variant, FIL1-theta, FILIPIL, FLJ00133, FLJ00148, FLJ00154, FLJ00236, FLJ00376, FLT3, FLT3LG, FN1, FNDC1, FNDC3A, FNDC3B, FNDC4, FNDC5, FNDC7, FNDC8, FOSB, FOSL1, FOXP3, FRMD1, FSD1, FSD1L, FSD2, FSTL3, FUCA2, GOS3, G18, G-26, GAB2, GAB3, gamma.1, GBP4, G-CSFR-1, G-CSFR-2, GDF15, GDF2, GHR, GJA1, GLEPP1, GLYRI, GM-CSF receptor beta chain, gp130, gp130-like monocyte receptor, gp250 precursor, GPI, GPR15, GPR75-ASB3, GPSM1, GRAIL, granulocyte colony-stimulating factor receptor, granulocyte macrophage-colony stimulating factor, granulocyte-macrophage colony stimulating factor 2, granulocyte-macrophage colony-stimulating factor precursor, GRAP2, GRO-beta, GRO-gamma, growth-inhibiting protein 45, GZMK, HAVCR2, HAX1, HBD, HCF-2, HCFC1, HCFC2, HCV NS5A-binding protein NS5ABP37, HDAC11, hDDM36, HEK, HEK11, HEK5, HEK7, HEK8, hematopoietic stem/progenitor cell induced protein 1, hematopoietic stem/progenitor cell induced protein 2, hematopoietic stem/progenitor cell induced protein 3, HES4, HGF, HGS, HIBDL, hIL-2Rg, HILPDA, HIN-1 putative cytokine, HMGB1, hmrp-2a, hmrp-2b, hNB-2, hNB-2s, hNB-3, host cell factor C2 variant, HOXB5, hp40, HSD13, hSHIP, HSP90B1, HSSOCS-2, HTK, HTPZP2, hTroy, Humig, HXB, hypothetical protein, ICOSLG, IFI16, IFI30, IFNA1, IFNA10, IFNA17, IFNA2, IFNA4, IFNA8, IFNAR1, IFNAR2, IFNB1, IFNG, IFNGR1, IFNGR2, IFNK, IFNL1, IFNL2, IFNL3, IFNLR1, IFNW1, IGANRP, IGDCC3, IGDCC4, IGF1R, IGFN1, IGSF22, IGSF9, IGSF9B, IK, IKBKB, IKK alpha, Interleukins, IL10, IL10RB, IL11, ILIIRA, I1-12 receptor beta2, IL12 receptor component, IL12A, IL12B, IL12RB1, IL12RB2, IL13, IL-13Ra, IL13RA1, IL13RA2, IL15, IL15RA, IL16, IL-17, IL-17 receptor, IL17A, IL17B, IL17BR, IL17C, IL17D, IL-17D, IL17D precursor, IL17E, IL17F, IL17RA, IL17RB, IL17RC, IL-17RC, IL-17RD, IL-17RE, IL18, IL-18 receptor beta splice variant, IL18BP, IL18R1, ILi8RAP, IL19, IL1A, IL1B, IL1BCE, IL1F10, IL1F7, IL1L1, IL1R1, IL1R2, ILIRAP, ILIRAPLI, IL1RAPL2, IL1RL1, IL1RL2, IL1RN, IL2, IL15, IL20, IL20RA, IL20RB, IL21, IL-21, IL21R, IL22, IL22BP, IL22R, IL22RA1, IL22RA2, IL23A, IL23R, IL-23R, IL-24 splice variant delE3, IL-24 splice variant delE5, IL25, IL26, IL27, IL27RA, IL28A, IL28B, IL28C, IL28RA, IL29, IL30, IL2RA, IL2RB, IL2RG, IL3, IL31, IL31RA, IL32, IL33, IL34, IL36A, IL36B, IL36G, IL36RN, IL37, IL3RA, IL4, IL411, IL4R, IL5, IL5RA, IL6, IL6R, IL6ST, IL7, IL7R, IL9, IL9R, il-xr, ING3, INPP5D, INSR, INSRR, insulin receptor variant, insulin responsive sequence DNA binding protein-1, integrin beta 4 isoform 3 precursor variant, interferon alpha 2b, interferon gamma, interferon-lambdal, interferon-lambda2, interferon-lambda3, interleukin 10 receptor, beta, interleukin 11 receptor, alpha, interleukin 12, P40, interleukin 13, interleukin 13 receptor, alpha 1 precursor variant, interleukin 17A, interleukin 17B, interleukin 17C, interleukin 18 precursor, interleukin 23 p19 subunit, interleukin 23 receptor isoform 1, interleukin 32 variant, interleukin 34 isoform 1 precursor, interleukin 34 isoform 2 precursor, interleukin 4 receptor alpha chain isoform a precursor variant, interleukin 6 receptor isoform 1 precursor variant, interleukin-1 homolog 1, interleukin-1 homolog 2, interleukin-1 homolog 4, interleukin-11 receptor alpha chain, interleukin-13 receptor, interleukin-17 beta, interleukin-1-related protein long isoform, interleukin-1-related protein long isoform a, interleukin-1-related protein short isoform, interleukin-2, interleukin-32 small, interleukin-32 theta, interleukin-33, intermediate prolactin receptor isoform, IRAK1, IRAK3, IREB2 variant, IRF9, IRS2, ISG15, ITGA1, ITGAL, ITGB2, ITGB4, ITPK1, JAB, JAK2, JAK3, JAKMIP1, JOSD2, KAL, KAL1, KALIG-1, KALRN, KAT6B, KCNA3, KCNJ12, KIAA0273, KIAA0282, KIAA0283, KIAA0318, KIAA0343, KIAA0671, KIAA0756, KIAA0970, KIAA1030, KIAA1132, KIAA1146, KIAA1297, KIAA1355, KIAA1397, KIAA1459, KIAA1496, KIAA1497, KIAA1510, KIAA1514, KIAA1568, KIAA1628, KIAA1666, KIAA1866, KLF8, KLRF1, LiCAM, LAR, LBP, LD78 alpha beta, LEPR, leptin receptor, LGI3, LICR2, LIF, LIFR, LILRA2, LIMK2, LOC57019, LOC728835, long myosin light chain kinase, LRG1, LRRC20, LRRC70, LRRFIP2, LRRN1, LRRN4, LTA, LTB, LTBP1, LTBP2, lymphokine, lymphotoxin beta isoform variant, lysophosphatidic acid acyltransferase-alpha, lysophosphatidic acid acyltransferase-beta, macrophage colony-stimulating factor 1, MAF, magic roundabout, MAPK14, MCP3, MCP-3, MCP4, MCP-4, MDK, MEP1B, MERTK, MEX3C, MGDF, MIC-1, microtubule-associated protein GLFND, MIP-1 delta, MIPla, MIP2a, mitochondria associated granulocyte macrophage CSF signaling molecule Magmas, ML1, MLCK, MMP9, MNAT1, MON1B, MOV10, MPIF-1, MPL, MRPL17, MSLN, MTHFD2L, MTUS1, MUSK, MYBPC1, MYBPC2, MYBPC3, MYBPH, MYBPHL, MYDGF, myeloproliferative leukemia virus oncogene, MYLK, MYOM1, MYOM2, MYOM3, NAA35, NAMPT, NC28, NCAM, N-CAM, NCAM1, NCAM2, NCAM21, Nck, Ash and phospholipase C gamma-binding protein NAP4, NCR1, NCR3, NCR3LG1, NCSTN, NDFIP1, NDUFA2, NDUFB6, NEO1, neogenin, neogenin homolog 1 variant, neshbp, NET PTK, Neural cell adhesion molecule 1, 120 kDa isoform precursor variant, neural cell adhesion molecule CD56, Neural cell adhesion molecule variant, neurotrophin-1/B-cell stimulating factor-3, NFAM1, NFASC, NFAT1, NFATC1, NFATC4, NHLH1, NILR, NIPSNAP1, NIPSNAP2, NKSF1, NKSF2, NLRC5, NLRP11, NLRP12, NLRP13, NLRP2, NLRP4, NLRP6, NLRP7, NLRR-1, NOX5, N-PAC, NR2C2, NR4A1, NRCAM, OBSCN, OC-116KDa, OCLN, OPTC, OR2H1, OSM, OSMR, OSMRB, osteoprotegerin ligand, OTUB1, OTUD6B, OTUD7B, P2RY8/CRLF2 fusion, p48, PANX2, PARC, PDCD1LG2, PGLYRP1, PHF11, PHYHIP, PHYHIPL, P19, PIAS1, PIBF1, PIK3R3, PLA2G2D, PLAC8, pLD78 peptide, PLK3, PLTP, PLXNC1, POMGNT2, PP14212, PPBP, PPIA, PPM1F, PPM1H, PPP2R5A, PPP3CC, PPP5C, PPY, PREX1, prk, PRLR, PR00915, prolactin receptor, prolactin receptor delta 7/11, prolactin receptor isoform delta Si precursor, proliferation associated cytokine-inducible protein CIP29, protein tyrosine phosphatase delta, protein tyrosine phosphatase sigma, protein tyrosine phosphatase, receptor type, D isoform 4 precursor variant, protein tyrosine phosphatase, receptor type, F isoform 2 precursor variant, protein tyrosine phosphatase, receptor type, G precursor variant, protein tyrosine phosphatase, receptor type, K precursor variant, protein tyrosine phosphatase, receptor type, sigma isoform 3 precursor variant, protein-tyrosine phosphatase, PRR16, PRSS27, PRTG, PSMA4, PTCHD1, PTGDR, PTGES, PTN, PTPRB, PTPRC, PTPRD, PTPRE, PTPRF, PTPRG, PTPRH, PTPRJ, PTPRK, PTPRM, PTPRO, PTPRQ, PTPRS, PTPRT, PTPRU, PTPRZ, PTPRZ1, PTPsigma, PTX4, PUS7L, putative cytokine receptor CRL4 precursor, PYPAF6, PYRIN-containing Apafl-like protein 2, PYRIN-containing Apafl-like protein 3, PYRIN-containing APAF1-like protein 4, PYRIN-containing APAF1-like protein 5, PYRIN-containing APAF1-like protein 7, PYY, RAB40A, RAB40AL, RAB40B, RAB40B, member RAS oncogene family variant, RAB40C, RAB6B, RANTES precursor, Rar protein, Rar-2 protein, RBM15, RBM5 variant, RCAN3, receptor protein tyrosine phosphatase hPTP-J precursor, Receptor protein tyrosine phosphatase hPTP-J precursor variant, receptor tyrosine kinase, receptor-type protein tyrosine phosphatase 0 isoform a precursor variant, RGS2, RIMBP2, RIMBP3, RIMBP3B, RIMBP3C, RIPK4, RMC1, RNASE10, RNASE7, RNASE9, RNASET2, RNF113A, RNF128, RNF41, ROBO1, ROBO2, ROBO2 isoform a, ROBO2 isoform b, ROBO3, ROBO4, RORC, ROS1, RPL27, RPL36, RPS21, R-PTP-kappa, RPTP-rho, rse, RSL24D1, S100A12, S100A8, S100A9, SIPR4, SAC3D1, SAP/SH2D1A, SAP-1, SARNP, SASH1, SCAMP5, SCGB3A1, SCGB3A2, SCM-1, SCYA13, SCYA16, SCYA26, SCYEl, SDC4, SDC4-ROS1_S2,R32, SDC4-ROS1_S4,R32, SDK1, SDK2, secreted osteoclastogenic factor of activated T cells, SELE, SEMA7A, SENP3, SER-PINB9, serum/glucocorticoid regulated kinase-like isoform 1 variant, SETDIB, SGK3, SGK-like protein SGKL, SH2 domain containing SOCS box protein SOCS4, SH2B1, SH2B3, shen-dan, SIGIRR, SIGLECi4, Similar to RIKEN cDNA 3930401K13 gene, SKIP1, SKIP3, sky, SLAMF9, SLC2A5, SLC2A9, SLC34A2/ROS fusion, SLC34A2-ROS1, SLC39A13, SLC39A3, SLC4A3, SLC9A8, SLC9B2, SLURPI, small cytokine B subfamily member 11 SCYB11 precursor, SMIM27, SMPD2, SNED1, SNX10, SOCS box containing protein RAR2A, SOCS box protein ASB-5, SOCS1, SOCS-1, SOCS2, SOCS3, SOCS4, SOCS5, SOCS6, SOCS7, SORL1, SPATA2, SPOCK3, SPP1, SPPL2B, SPRY domain-containing SOCS box protein SSB-1, SPRY domain-containing SOCS box protein SSB-1 variant, SPRY domain-containing SOCS box protein SSB-2, SPRY domain-containing SOCS box protein SSB-3, SPRY domain-containing SOCS box protein SSB-4, SPSB1, SPSB2, SPSB3, SPSB4, STAM, STAM2, STAMBP, STAT induced STAT inhibitor-1, STAT induced STAT inhibitor-2, STAT induced STAT inhibitor-3, STAT1, STAT5A, STAT5B, STAT-induced STAT inhibitor-2, stem cell factor, STIMATE, STK35, STK40, striated muscle preferentially expressed protein, suppressor of cytokine signaling 3, surface glycoprotein, Ig superfamily member variant, SUSD2, SWIP1, SYNJ2BP, synleurin, TACC2, TAIF, TARM1, TBX21, TBX5, TCEB1, TCIRGI, TEC, TEK, TEK tyrosine kinase variant, tenascin XB isoform 1 variant, tenascin-C isoform 14/AD1/16, testicular tissue protein Li 126, testicular tissue protein Li 64, testis tissue sperm-binding protein Li 57p, TEX12, TFPI, THEMIS2, THNSL2, THPO, thymic stromal lymphopoietin protein receptor TSLPR, thymic stromal lymphopoietin protein TSLP, TIE, tie receptor tyrosine kinase, TIEl, Tie-2, TIGIT, TIMP1, tip3, TIRAP, Titin, TLRI, TLR3, TLR6, TM7SF3, TMEM102, TMEM110-MUSTNI, TMSB4X, TMX2, TNC, TNC variant protein, TNF, TNFAIP3, TNFAIP8L2, TNFRSF11B, TNFRSF12A, TNFRSF13C, TNFRSF21, TNFRSF25, TNFRSF4, TNFRSF8, TNFSF10, TNFSF11, TNFSF12, TNFSF13, TNFSF13B, TNFSF15, TNFSF18, TNFSF4, TNFSF8, TNFSF9, TNL, TNN, TNR, TNXB, TOPORS, Trad, TRAF6, TRIM21, TRIM3, TRIM42, TRIM46, TRIM67, TRIM8, TRIM9, TRPM4, TSLP, TTN, TULP4, tumor necrosis factor receptor, TUSP, TUT4, TUT7, TWIST2, TYK2, type VII collagen, type XII collagen, type-I T cell cytokine receptor, TYRO3, tyrosyl-tRNA synthetase, tyrosyl-tRNA synthetase variant, U2AF1L4, UBA6, UBAP1, ubiquitin ligase E3 alpha-I, ubiquitin ligase E3 alpha-II, UBR2, UFO, undulin 1, undulin 2, UNQ1942, UNQ2421, UNQ288, UNQ296, UNQ3121, UNQ421, UNQ5793, UNQ604, UNQ6309, UNQ6368, UNQ6389, UNQ6504, UNQ693, UQCRH, USH2A, USMG5, USP15, USP17L10, USP17LII, USP17L12, USP17L13, USP17L15, USP17L17, USP17L18, USP17L19, USP17L2, USP17L20, USP17L21, USP17L22, USP17L24, USP17L25, USP17L26, USP17L27, USP17L28, USP17L29, USP17L3, USP17L30, USP17L4, USP17L5, USP17L7, USP17L8, USP18, USP36, UTY, V alpha 1, V alpha 13, VCAM1, VESPR, VNN2, VSIG2, VWA1, WARS, WD SOCS-box protein 1 isoform 1 variant, WDR26, WSB1, WSB-1, WSB-1 isoform, WSB-1 protein, WSB2, WSB-2, WSX1, WWOX, XA, XB, XBP1, XCL1, XCL2, XKR4, YARS, ZBED3, ZBP1, ZC3H12D, ZC3H15, ZCYTO10, zcytor5, ZCYTOR7, ZFP36, ZNF366, ZNF580 및 ZNF827, but it is not limited thereto.

Specifically, the antibody may be an antibody bound to interleukins or interferon protein.

The antibody may be IgG or an antibody specifically bound to at least one protein selected from the group consisting of PD-1, CTLA-4, TIM-3, BTLA, VISTA, LAG-3, PD-L1, PD-L2, B7-H3, B7-H4, CD28, CD27, CD137, HVEM, GITR, VEGFR, VEGF, EGFR, EGF, IL-1, IL-6, IL-23, TGF-beta, CTGF, TSLP, TNF-alpha, Notch and OX40, but it is not limited thereto, as long as it is recognized as a conventional antibody from a biological point of view.

The porous silica particles are particles based on silica ($SiO_2$) material and have a nano-scale particle size.

The porous silica nanoparticles of the present invention are porous particles, each of which has nano-scale pores and can carry an antibody or cytokine on a surface thereof and/or an inside of the pores.

The porous silica particles of the present invention are biodegradable particles, which carry an antibody or cytokine, and can release the same, that is, an antibody or cytokine while being biodegraded in the body when administered to the body. The porous silica particles of the present invention may be slowly degraded in the body to allow sustained release of the supported antibody or cytokine. For example, "t", at which a ratio of absorbance of the following Equation 1 becomesb ½, is 24 or more:

$$A_t/A_0$$ [Equation 1]

(wherein $A_0$ is absorbance of the porous silica particles measured by putting 5 ml of suspension containing 1 mg/ml of porous silica particles into a cylindrical permeable membrane having pores with a pore diameter of 50 kDa, 15 ml of the same solvent as the suspension comes into contact with an outside of the permeable membrane, and the inside/outside of the permeable membrane are horizontally stirred at 60 rpm and at 37° C., pH of the suspension is 7.4, and $A_t$ indicates absorbance of the porous silica particle measured after lapse of "t" hours since $A_0$ was measured).

The above Equation 1 means what a rate the porous silica particles are degraded in an environment similar to the body.

Figure 34:
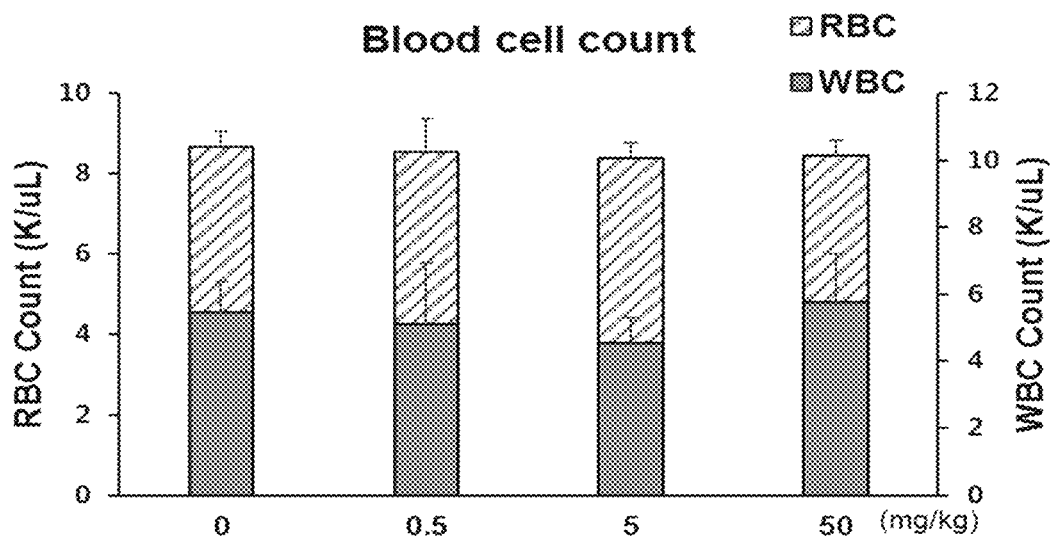
Figure 35:
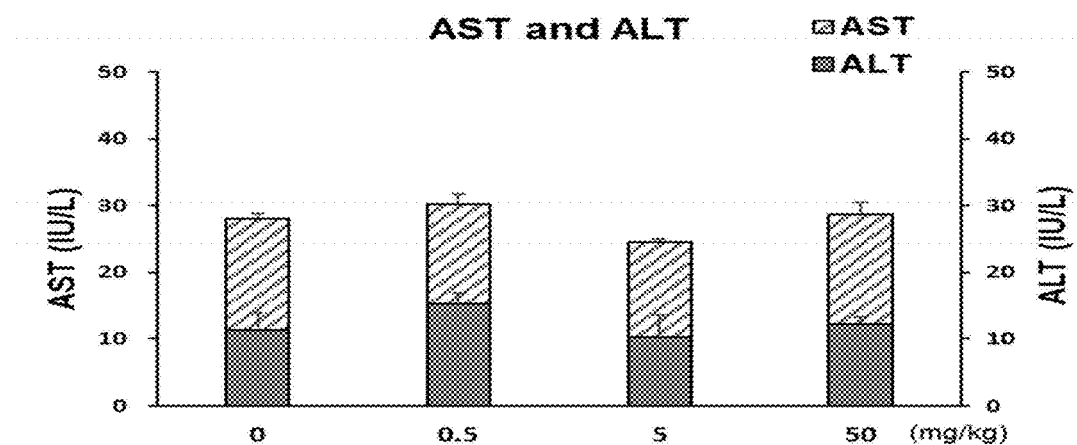
Figure 36:
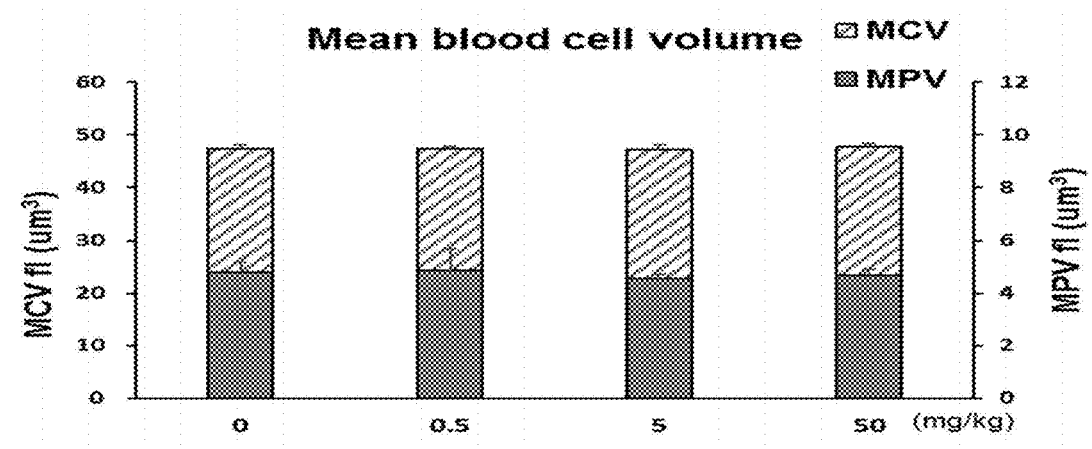
Figure 37:
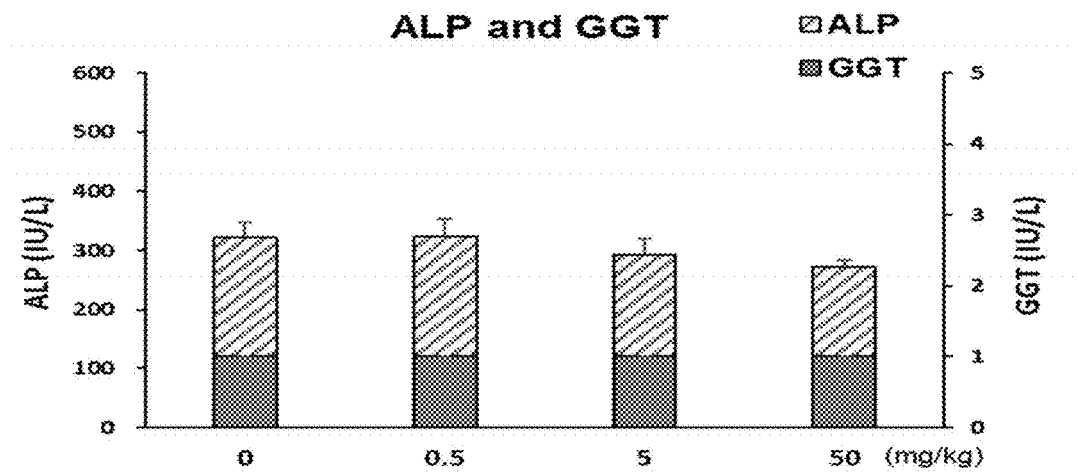
Figure 38:
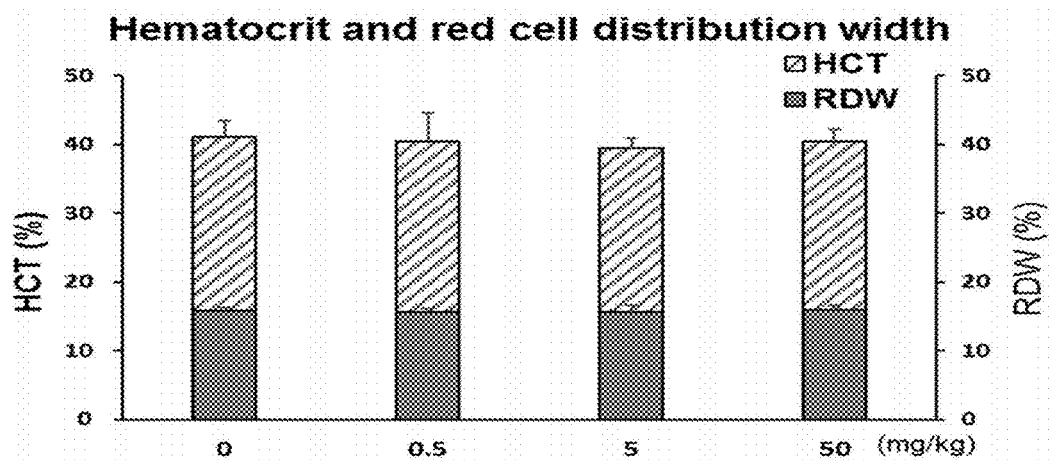
Figure 39:
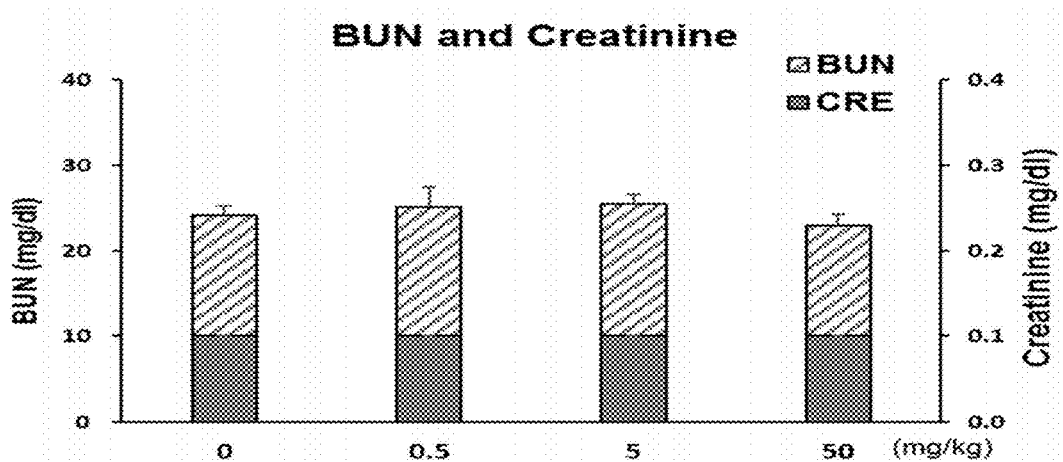
Figure 40:
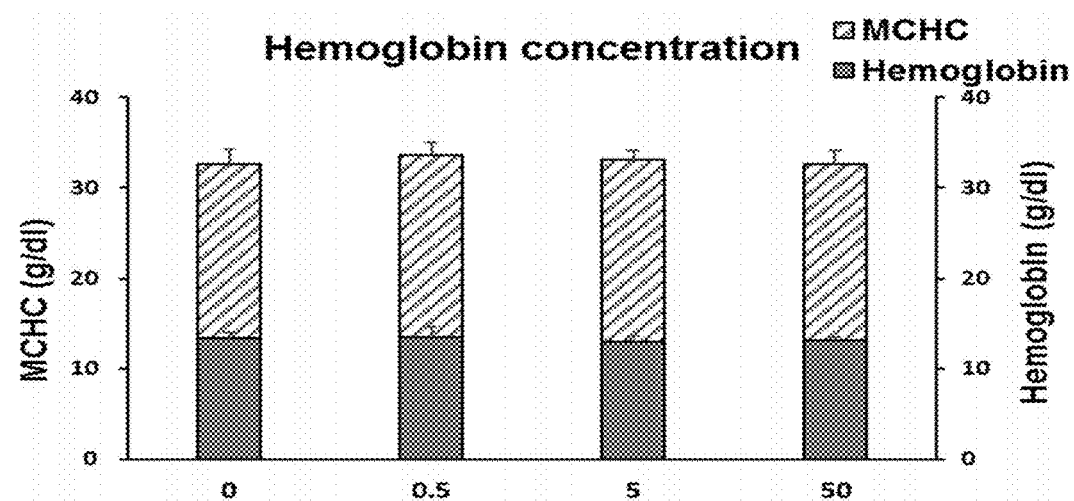
Figure 41:
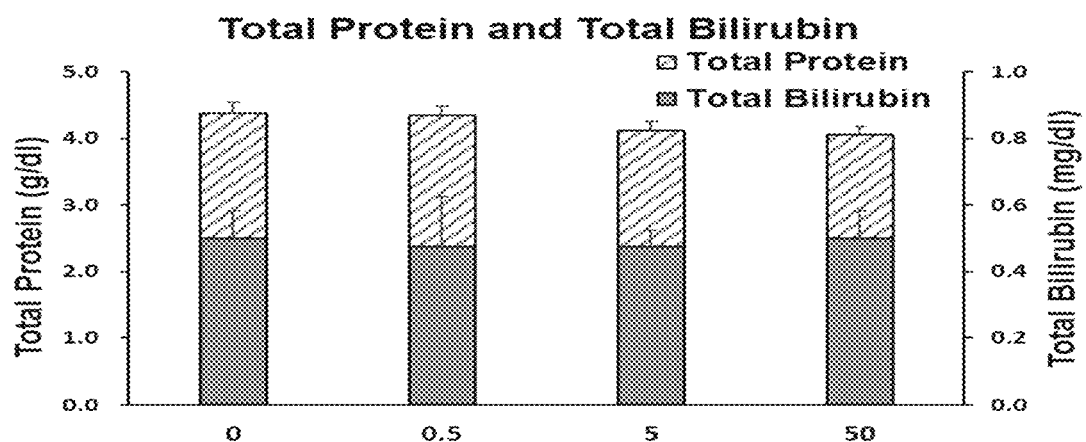
Figure 42:
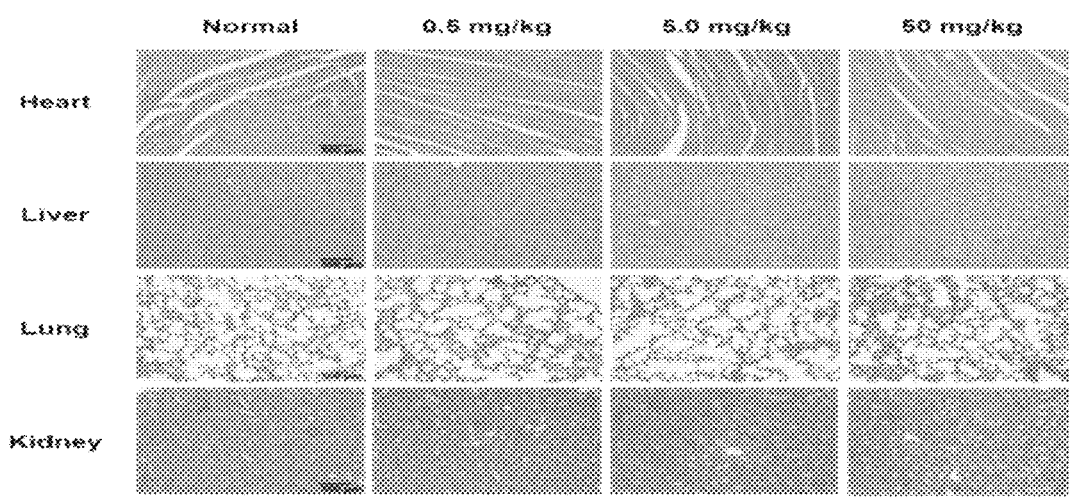
Figure 43:
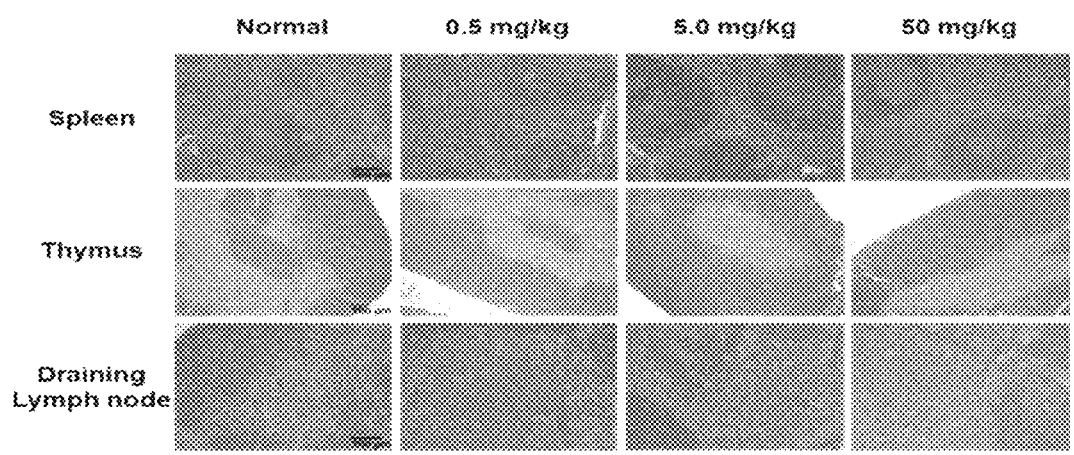

As shown in FIG. 34, for example, absorbances $A_0$ and $A_t$ in the above Equation 1 may be measured after placing porous silica particles and a suspension in a cylindrical permeable membrane and also placing the same suspension outside the permeable membrane.

The porous silica particles of the present invention are biodegradable, and may be slowly degraded in the suspension. The diameter of 50 kDa corresponds to about 5 nm, which allows biodegradable porous silica particles to pass through a permeable membrane having a diameter of 50 kDa, and a cylindrical permeable membrane is under horizontal agitation at 60 rpm to evenly blend the suspension, such that the degraded porous silica particles can come out of the permeable membrane.

The absorbance in the above Equation 1 may be measured, for example, under an environment in which the suspension outside the permeable membrane is replaced with a new suspension. The suspension may be continuously replaced, or replaced every period wherein the period is periodic or irregular. For example, the suspension may be replaced at 1 hour interval, 2 hours interval, 3 hours interval, 6 hours interval, 12 hours interval, 24 hours interval, 2 days interval, 3 days interval, 4 days interval, 7 days interval, etc., within a range of 1 hour to 1 week, but it is not limited thereto.

The absorbance ratio of ½ means that the absorbance is half of the initial absorbance after t hours, that is, that approximately half of the porous silica particles are degraded.

The suspension may be a buffer solution, for example, at least one selected from the group consisting of phosphate buffered saline (PBS) and simulated body fluid (SBF), and more specifically, PBS.

"t" in the above Equation 1 of the present invention, at which the absorbance ratio becomes ½, may be 24 or more, for example, t may range from 24 to 120. That is, within the above range, t may range from 24 to 96, 24 to 72, 30 to 70, 40 to 70, 50 to 65, etc., but it is not limited thereto.

With regard to the porous silica particles of the present invention, t at which the absorbance ratio in the above Equation 1 becomes ⅕ may range from 70 to 140. For example, t may range from 80 to 140, 80 to 120, 80 to 110, 70 to 140, 70 to 120, 70 to 110, etc. within the above range, but it is not limited thereto.

With regard to the porous silica particles of the present invention, t at which the absorbance ratio in the above Equation 1 becomes 1/20 may range from 130 to 220. For example, t may range from 130 to 200, 140 to 200, 140 to 180, 150 to 180, etc. within the above range, but it is not limited thereto.

With regard to the porous silica particles of the present invention, t at which the absorbance ratio in the above Equation 1 becomes 0.01 or less may be 250 or more. For example, t may be 300 or more, 350 or more, 400 or more, 500 or more, 1000 or more, etc. and the upper limit may be 2000, but it is not limited thereto.

With regard to the porous silica particles of the present invention, the absorbance ratio and t in the above Equation 1 have high positive correlation. For example, Pearson correlation coefficient may be 0.8 or more, and for example, 0.9 or more and 0.95 or more.

"t" in the above Equation 1 means how fast the porous silica particles are degraded under the environment similar to the body. That is, t may be regulated by adjusting, for example, a surface area, a particle size, a pore diameter, substituents on the surface of the porous silica particles and/or the inside of the pores, compactness of the surface and the like.

For example, the surface area of the particles may be increased to reduce t, or the surface area may be decreased to increase t. The surface area may be regulated by adjusting the particle size and the pore diameter of the particles. Further, if direct exposure of the porous silica particles to the environment (such as solvents) is reduced by placing substituents on the surface of the particles and/or the inside of the pores, t may be increased. Further, when the porous silica particles support or carry an antibody or cytokine, and when increasing affinity between the antibody or cytokine and the porous silica particles, direct exposure of the porous silica particles to the environment may be reduced, thereby increasing t. In addition, t may be increased by preparing the particles with more compact surface. As described above, various examples of adjusting t in the above Equation 1 have been described, but it is not limited thereto.

The porous silica particles of the present invention may have a spherical shape, but it is not limited thereto.

The porous silica particles of the present invention may have an average diameter of, for example, 150 to 1000 nm. For example, the average diameter may range from 150 to 800 nm, 150 to 500 nm, 150 to 400 nm, 150 to 300 nm, and 150 to 200 nm, etc. within the above range, but it is not limited thereto.

The porous silica particles of the present invention may have an average pore diameter of, for example, 1 to 100 nm. For example, the pore diameter may range from 5 to 100 nm, 7 to 100 nm, 7 to 50 nm, 10 to 50 nm, 10 to 30 nm, 7 to 30 nm, etc., within the above range, but it is not limited thereto. The porous silica particles having a large diameter as described above may carry a large amount of the antibody or cytokine, and may further carry a large-sized antibody or cytokine.

The porous silica particles of the present invention may have a BET surface area of, for example, 200 to 700 $m^2/g$. For example, the BET surface area may range from 200 to 700 $m^2/g$, 200 to 650 $m^2/g$, 250 to 650 $m^2/g$, 300 to 700 $m^2/g$, 300 to 650 $m^2/g$, 300 to 600 $m^2/g$, 300 to 550 $m^2/g$, 300 to 500 $m^2/g$, 300 to 450 $m^2/g$, etc. within the above range, but it is not limited thereto.

Porous silica nanoparticles of the present invention may have a volume per gram, for example, 0.7 to 2.2 ml. For example, the volume may range from 0.7 to 2.0 ml, 0.8 to 2.2 ml, 0.8 to 2.0 ml, 0.9 to 2.0 ml, 1.0 to 2.0 ml, etc. within the above range, but it is not limited thereto. If the volume per gram is too small, a degradation rate may be too high. Further, it is difficult to manufacture excessively large particles or particles having an intact shape.

The porous silica particles of the present invention may have hydrophilic substituents and/or hydrophobic substituents on an outer surface thereof and/or an inside of the pores. For example, only hydrophilic substituents or only hydrophobic substituents may exist on both the surface of the particles and inside of the pores, hydrophilic substituents or hydrophobic substituents may be present on either the surface of the particles or the inside of the pores, or hydrophilic substituents may be present on the surface of the particles while hydrophobic substituents may exist inside of the pores, or vice versa.

Release of the antibody or cytokine supported on the porous silica particles according to the present invention is mainly performed by degradation of nanoparticles. Specifically, interaction of the porous silica particles with the release environment of the antibody or cytokine is adjusted to regulate a degradation rate of the nanoparticles, so that a release rate of the antibody or cytokine may be regulated. Further, the antibody or cytokine may be diffused and released from the nanoparticles, wherein adjusting substituents may regulate a binding force of the antibody or cytokine to the nanoparticles, thereby controlling release of the antibody or cytokine.

Further, in order to increase a binding force of the silica particles to the poorly soluble (hydrophobic) antibody, cytokine or material, hydrophobic substituents may be present inside of the pores of the particle. Further, in aspects of easy use and formulation, the surface of the particles may also be treated to have hydrophilic substituents.

The hydrophilic substituents may include, for example, hydroxyl group, carboxy group, amino group, carbonyl group, sulfhydryl group, phosphate group, thiol group, ammonium group, ester group, imide group, thioimide group, keto group, ether group, indene group, sulfonyl group, polyethyleneglycol group and the like. Further, the hydrophobic substituent may include, for example, substituted or unsubstituted C1 to C30 alkyl group, substituted or unsubstituted C3 to C30 cycloalkyl group, substituted or unsubstituted C6 to C30 aryl group, substituted or unsubstituted C2 to C30 heteroaryl group, halogen group, C1 to C30 ester group, halogen-containing group and the like.

Further, the porous silica particles of the present invention may be positively charged, negatively charged and/or uncharged at an outer surface thereof and/or an inside of the pores. For example, both the surface of the particles and the inside of the pores may be positively charged or negatively charged, only the surface of the particles or the inside of the pores may be positively charged or negatively charged. Alternatively, the surface of the particles may be positively charged while the inside of the pores may be negatively charged or vice versa, which is similar to the case of being uncharged.

The charging may be performed, for example, by the presence of a nonionic substituent, a cationic substituent or an anionic substituent.

The cationic substituent may include, for example, amino group or any other nitrogen-containing group as a basic group, and the anionic substituent may include, for example, a carboxy group (—COOH), sulfonic acid group (~SO3H), thiol group (—SH), etc. as an acidic group, but it is not limited thereto.

Likewise, when interaction of the porous silica particles with release environment of the antibody or cytokine is regulated by adjusting the substituents through charging, a degradation rate of nanoparticles may be regulated to control a release rate of the antibody or cytokine. Further, the antibody or cytokine may be diffused and released from the nanoparticles. In this regard, adjusting the substituents may regulate a binding force of the antibody or cytokine to the nanoparticles, thereby controlling release of the antibody or cytokine.

Further, the porous silica particles of the present invention may include substituents for the purposes of: supporting the antibody or cytokine on the surface of the particles and/or the inside of the pores; delivery of the antibody or cytokine into a target cell; supporting other substances for other purposes; or binding of additional substituents. Further, the porous silica particles may also include antibodies, ligands, cell permeable peptides, or aptamers bound thereto.

The substituents on the surface of the particles and/or the inside of the pores, charge, binders, etc. described above may be added by, for example, surface modification.

Surface modification may be performed, for example, by reacting a compound having a substituent to be introduced with the particles, wherein the compound may be, for example, alkoxysilane having C1 to C10 alkoxy group, but it is not limited thereto. The alkoxysilane has one or more alkoxy groups, for example, 1 to 3 alkoxy groups. Further, there may be a substituent to be introduced into a site where the alkoxy group is not bound, or a substituent substituted with the same.

The porous silica particles of the present invention may be manufactured, for example, through small pore particle preparation and pore expansion processes and, if necessary, may be manufactured further through calcination, or surface modification process and the like. If both the calcination and the surface modification processes have been implemented, the particles may be surface-modified after calcination.

The small pore particles may be, for example, particles having an average pore diameter of 1 to 5 nm.

The small pore particles may be harvested by adding a surfactant and a silica precursor in a solvent, followed by agitation and homogenization.

The solvent may be water and/or an organic solvent, and the organic solvent may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, γ-butyrolactone, 1,3-dimethyl-imidazolidinone, methylethylketone, cyclohexanone, cyclopentanone, 4-hydroxy-4-methyl-2-pentanone, etc.; aromatic carbon-based materials such as benzene, toluene, xylene, tetramethylbenzene, etc.; alkyl amides such as N,N-dimethylformamide, N,N-dibutylformamide, N,N-dimethylacetamide, N-methylpyrrolidone, etc.; alcohols such as methanol, ethanol, propanol, butanol, etc.; glycol ethers (cellosolve) such as ethyleneglycol monoethyl ether, ethyleneglycol monomethyl ether, ethyleneglycol monobutyl ether, diethyleneglycol monoethyl ether, diethyleneglycol monomethyl ether, diethyleneglycol monobutyl ether, propyleneglycol monomethyl ether, propyleneglycol monoethyl ether, dipropyleneglycol diethyl ether, triethyleneglycol monoethyl ether, etc.; others such as dimethylacetamide (DMAc), N,N-diethylacetamide, dimethylformamide (DMF), diethylformamide (DEF), N,N-dimethylacetamide (DMAc), N-methylpyrrolidone (NMP), N-ethylpyrrolidone (NEP), 1,3-dimethyl-2-imidazolidinone, N,N-dimethylmethoxyacetamide, dimethyl sulfoxide, pyridine, dimethyl sulfone, hexamethylphosphoamide, tetramethylurea, N-methylcarrolactam, tetrahydrofuran, m-dioxane, P-dioxane, 1,2-dimethoxyethane and the like. Specifically, alcohol, more specifically methanol may be used, but it is not limited thereto.

When using a mixed solvent of water and the organic solvent, a relative ratio of water and organic solvent may be, for example, in a volume ratio of 1:0.7 to 1.5, for example, 1:0.8 to 1.3, but it is not limited thereto.

The surfactant may include, for example, cetyltrimethylammonium bromide (CTAB), hexadecyltrimethylammonium bromide (TMABr), hexadecyltrimethylpyridinium chloride (TMPrCl), tetramethylammonium chloride (TMACl), etc., and specifically, CTAB may be used.

The surfactant may be added, for example, in an amount of 1 to 10 g, for example, 1 to 8 g, 2 to 8 μg or 3 to 8 μg per liter of solvent, but it is not limited thereto.

The silica precursor may be added after stirring with addition of a surfactant to the solvent. The silica precursor may be, for example, tetramethyl orthosilicate (TMOS), but it is not limited thereto.

The stirring may be conducted, for example, for 10 to 30 minutes, but it is not limited thereto The silica precursor may be added in an amount of 0.5 to 5 ml per liter of solvent, for example, 0.5 ml to 4 ml, 0.5 to 3 ml, 0.5 to 2 ml, 1 to 2 ml, etc. within the above range, but it is not limited thereto.

If necessary, sodium hydroxide may further be used as a catalyst, specifically, and may be added under stirring after addition of the surfactant and before addition of the silica precursor to the solvent.

The sodium hydroxide may be added in an amount of 0.5 to 8 ml per liter of solvent, for example, 0.5 to 5 ml, 0.5 to 4 ml, 1 to 4 ml, 1 to 3 ml, 2 to 3 ml, etc. within the above range with respect to 1 M aqueous sodium hydroxide solution, but it is not thereto.

After addition of the silica precursor, the solution may be reacted with stirring. The stirring may be conducted for 2 to 15 hours, for example, 3 to 15 hours, 4 to 15 hours, 4 to 13 hours, 5 to 12 hours, 6 to 12 hours, 6 to 10 hours, etc. within the above range, but it is not limited thereto. If the stirring time (reaction time) is too short, nucleation may be insufficient.

After agitation, the solution may be aged. Aging may be performed for 8 to 24 hours, for example, for 8 to 20 hours, 8 to 18 hours, 8 to 16 hours, 8 to 14 hours, 10 to 16 hours, 10 to 14 hours, etc. within the above range, but it is not limited thereto.

Thereafter, the reaction product may be washed and dried to harvest porous silica particles and, if necessary, separation of unreacted material may proceed before washing.

Separation of the unreacted material may be implemented by separating the supernatant, for example, through centrifugation. For example, centrifugation may be conducted at 6,000 to 10,000 rpm, and the centrifugation time may range from 3 to 60 minutes, for example, 3 to 30 minutes, 3 to 30 minutes, 5 to 30 minutes, etc. within the above range, but it is not limited thereto.

The washing may be conducted with water and/or an organic solvent. Specifically, since different substances are dissolved in different solvents, water and the organic solvent may be used alternately once or several times, or the washing may be conducted with water or the organic solvent alone once or several times. The several times described above may be 2 times or more and 10 times or less, for example, 3 times or more and 10 times or less, 4 times or more and 8 times or less, 4 times or more and 6 times or less.

The organic solvent may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, γ-butyrolactone, 1,3-dimethyl-imidazolidinone, methylethylketone, cyclohexanone, cyclopentanone, 4-hydroxy-4-methyl-2-pentanone, etc.; aromatic carbon-based materials such as benzene, toluene, xylene, tetramethylbenzene, etc.; alkyl amides such as N,N-dimethylformamide, N,N-dibutylformamide, N,N-dimethylacetamide, N-methylpyrrolidone, etc.; alcohols such as methanol, ethanol, propanol, butanol, etc.; glycol ethers (cellosolve) such as ethyleneglycol monoethyl ether, ethyleneglycol monomethyl ether, ethyleneglycol monobutyl ether, diethyleneglycol monoethyl ether, diethyleneglycol monomethyl ether, diethyleneglycol monobutyl ether, propyleneglycol monomethyl ether, propyleneglycol monoethyl ether, dipropyleneglycol diethyl ether, triethyleneglycol monoethyl ether, etc.; others such as dimethylacetamide (DMAc), N,N-diethylacetamide, dimethylformamide (DMF), diethylformamide (DEF), N,N-dimethylacetamide (DMAc), N-methylpyrrolidone (NMP), N-ethylpyrrolidone (NEP), 1,3-dimethyl-2-imidazolidinone, N,N-dimethylmethoxyacetamide, dimethyl sulfoxide, pyridine, dimethyl sulfone, hexamethylphosphoamide, tetramethylurea, N-methylcarrolactam, tetrahydrofuran, m-dioxane, P-dioxane, 1,2-dimethoxyethane and the like. Specifically, alcohol, more specifically methanol may be used, but it is not limited thereto.

The washing may be conducted under centrifugation, for example, at 6,000 to 10,000 rpm, and the centrifugation time may range from 3 to 60 minutes, for example, 3 to 30 minutes, 3 to 30 minutes, 5 to 30 minutes, etc. within the above range, but it is not limited thereto.

Alternatively, the washing may be conducted by filtering out particles through a filter without centrifugation. The filter may have pores in a size of less than or equal to the diameter of the porous silica particles. When filtering the reaction solution with such a filter as described above, only particles remain on the filter, which may be washed by pouring water and/or an organic solvent on the filter.

In the washing, water and the organic solvent may be used alternately once or several times, or the washing may be conducted with water or the organic solvent alone once or several times. The several times described above may be 2 times or more and 10 times or less, for example, 3 times or more and 10 times or less, 4 times or more and 8 times or less, 4 times or more and 6 times or less.

The drying may be conducted, for example, at 20 to 100° C., but it is not limited thereto, and may also be conducted in a vacuum state.

Thereafter, the pore of the harvested porous silica particles may be expanded, and such pore expansion may be conducted using a pore swelling agent.

The pore swelling agent may include, for example, trimethylbenzene, triethylbenzene, tripropylbenzene, tributylbenzene, tripentylbenzene, trihexylbenzene, toluene, benzene, etc., and specifically, trimethylbenzene may be used, but it is not limited thereto.

Further, the pore swelling agent used herein may be, for example, N,N-dimethylhexadecylamine (DMHA), but it is not limited thereto.

The pore expansion may be performed, for example, by mixing the porous silica particles in the solvent with a pore swelling agent and heating the mixture to induce reaction.

The solvent may be water and/or an organic solvent, and the organic solvent may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, cyclohexanone, etc.; aromatic carbon-based materials such as benzene, toluene, xylene, etc.; alkyl amides such as N,N-dimethylformamide, N,N-dibutylformamide, N,N-dimethylacetamide, N-methylpyrrolidone, etc.; alcohols such as methanol, ethanol, propanol, butanol and the like. Specifically, alcohol, more specifically methanol may be used, but it is not limited thereto.

The porous silica particles may be added in a ratio of 10 to 200 μg per liter of solvent, for example, 10 to 150 g, 10 to 100 g, 30 to 100 g, 40 to 100 g, 50 to 100 g, 50 to 80 g, 60 to 80 g, etc., within the above range, but it is not limited thereto.

The porous silica particles may be evenly dispersed in a solvent. For example, the porous silica particles may be added to the solvent and ultrasonically dispersed. In the case of using a mixed solvent, the porous silica particles may be dispersed in a first solvent, followed by adding a second solvent thereto.

The pore swelling agent may be added in a ratio of 10 to 200 parts by volume ("vol. parts") to 100 vol. parts of solvent, for example, 10 to 150 vol. parts, 10 to 100 vol. parts, 10 to 80 vol. parts, 30 to 80 vol. parts, 30 to 70 vol. parts, etc. within the above range, but it is not limited thereto.

The reaction may be carried out at 120 to 190° C., for example, 120 to 190° C., 120 to 180° C., 120 to 170° C., 130 to 170° C., 130 to 160° C., 130 to 150° C., 130 to 140° C., etc. within the above range, but it is not limited thereto.

The reaction may be carried out for 6 to 96 hours, for example, 30 to 96 hours, 30 to 96 hours, 30 to 80 hours, 30 to 72 hours, 24 to 80 hours, 24 to 72 hours, 36 to 96 hours, 36 to 80 hours, 36 to 72 hours, 36 to 66 hours, 36 to 60 hours, 48 to 96 hours, 48 to 88 hours, 48 to 80 hours, 48 to 72 hours, 6 to 96 hours, 7 to 96 hours, 8 to 80 hours, 9 to 72 hours, 9 to 80 hours, 6 to 72 hours, 9 to 96 hours, 10 to 80 hours, 10 to 72 hours, 12 to 66 hours, 13 to 60 hours, 14 to 96 hours, 15 to 88 hours, 16 to 80 hours, 17 to 72 hours, etc. within the above range, but it is not limited thereto.

The time and temperature may be desirably adjusted within the ranges exemplified above so that the reaction may be carried out sufficiently but not excessively. For example, when the reaction temperature is reduced, the reaction time may be increased, and when the reaction temperature is increased, the reaction time may be shortened. If the reaction is not sufficiently performed, pore expansion may be insufficient. On the other hand, if the reaction proceeds excessively, the particles may collapse due to overexpansion of the pores.

The reaction may be carried out, for example, by gradually raising the temperature. Specifically, the reaction may be carried out by gradually raising the temperature at a rate of 0.5 to 15° C./min from the room temperature to the above-defined temperature. For example, the temperature may be raised at a rate of 1 to 15° C./min, 3 to 15° C./min, 3 to 12° C./min, 3 to 10° C./min, etc., but it is not limited thereto.

The reaction may be carried out under stirring. For example, the stirring may be implemented at a speed of 100 rpm or more, and specifically, at a speed of 100 to 1000 rpm, but it is not limited thereto.

After the reaction, the reaction solution may be cooled slowly, for example, by gradually decreasing the temperature. Specifically, the reaction may be carried out by gradually decreasing the temperature at a rate of 0.5 to 20° C./min from the above-defined temperature to room temperature. For example, the temperature may be decreased at a rate of 1 to 20° C./min, 3 to 20° C./min, 3 to 12° C./min, 3 to 10° C./min, etc. within the above range, but it is not limited thereto.

After cooling, the reaction product may be washed and dried to harvest porous silica particles having expanded pores. If necessary, unreacted material may be first separated before washing.

Separation of the unreacted material may be implemented by separating the supernatant, for example, through centrifugation. Herein, centrifugation may be conducted, for example, at 6,000 to 10,000 rpm, and the centrifugation time may range from 3 minutes to 60 minutes. For example, the centrifugation may be conducted for 3 to 30 minutes, 3 to 30 minutes, 5 to 30 minutes, etc. within the above range, but it is not limited thereto.

The washing may be conducted with water and/or an organic solvent. Specifically, since different substances are dissolved in different solvents, water and the organic solvent may be used alternately once or several times, or the washing may be conducted with water or the organic solvent alone once or several times. The several times described above may be 2 times or more and 10 times or less, for example, 3 times, 4 times, 5 times, 6 times, 7 times, 8 times, etc.

The organic solvent may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, cyclohexanone, etc.; aromatic carbon-based materials such as benzene, toluene, xylene, etc.; alkyl amides such as N,N-dimethylformamide, N,N-dibutylformamide, N,N-dimethylacetamide, N-methylpyrrolidone, etc.; alcohols such as methanol, ethanol, propanol, butanol and the like. Specifically, alcohol, more specifically methanol may be used, but it is not limited thereto.

The washing may be conducted under centrifugation, for example, at 6,000 to 10,000 rpm, and the centrifugation time may range from 3 to 60 minutes, for example, 3 to 30 minutes, 3 to 30 minutes, 5 to 30 minutes, etc. within the above range, but it is not limited thereto.

Alternatively, the washing may be conducted by filtering out particles through a filter without centrifugation. The filter may have pores in a size of less than or equal to the diameter of the porous silica particles. When filtering the reaction solution with such a filter as described above, only particles remain on the filter, which may be washed by pouring water and/or an organic solvent on the filter.

In the washing, water and the organic solvent may be used alternately once or several times, or the washing may be conducted with water or the organic solvent alone once or several times. The several times described above may be 2 times or more and 10 times or less, for example, 3 times or more and 10 times or less, 4 times or more and 8 times or less, 4 times or more and 6 times or less.

The drying may be conducted, for example, at 20 to 100° C., but it is not limited thereto, and may also be conducted in a vacuum state.

Thereafter, the harvested particles may be subjected to calcination, which is a process of heating the particles to remove silanol groups present on the surface of the particles and inside of the pores so as to reduce reactivity of the particles, provide a more compact structure, and remove organic matter filling the pores. For example, the particles may be heated to a temperature of 400° C. or higher. The upper limit of the temperature is not particularly limited but may be 1000° C., 900° C., 800° C., 700° C., etc. The heating may be conducted, for example, for 3 hours or more. The upper limit of the heating time is not particularly limited but may be 24 hours, 12 hours, 10 hours, 8 hours, 6 hours, etc. More particularly, the heating may be conducted at 400 to 700° C. for 3 to 8 hours or at 500 to 600° C. for 4 to 5 hours, but it is not limited thereto.

Removing the organic matter filling the pores can prevent some problems of cytotoxicity or foaming caused by the remaining organic matter.

Then, the harvested porous silica particles may be subjected to surface modification, and the surface modification may be performed on the surface of the particles and/or the inside of the pores. Both the particle surface and the inside of the pores may be surface-modified in the same manner, or may be surface-modified differently.

The particles may be charged or have hydrophilic and/or hydrophobic properties through surface modification.

More specifically, in order to effectively support the antibody or cytokine, surface modification of the porous silica particles may be performed by having at least one substituent selected from the group consisting of amino, aminoalkyl, alkylamino, heterocyclic aromatic compound group containing a nitrogen atom, cyan and guanidine groups.

Surface modification may be performed, for example, by reacting a compound having a hydrophilic, hydrophobic, cationic or anionic substituent to be introduced with the particles, wherein the compound may be, for example, alkoxysilane having a C1 to C10 alkoxy group, but it is not limited thereto.

The alkoxysilane has one or more alkoxy groups, for example, 1 to 3 alkoxy groups. Further, there may be a substituent to be introduced into a site where the alkoxy group is not bound, or a substituent substituted with the same.

When alkoxysilane reacts with the porous silica particles, a covalent bond is formed between a silicon atom and an oxygen atom so that the alkoxysilane may be bound to the surface of the porous silica particles and/or the inside of the pores. Since the alkoxysilane has a substituent to be introduced, the corresponding substituent may be introduced into the surface of the porous silica particles and/or the inside of the pores.

The reaction may be carried out by reacting the porous silica particles dispersed in a solvent with alkoxysilane.

The solvent may be water and/or an organic solvent, and the organic solvent may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, γ-butyrolactone, 1,3-dimethyl-imidazolidinone, methylethylketone, cyclohexanone, cyclopentanone, 4-hydroxy-4-methyl-2-pentanone, etc.; aromatic carbon-based materials such as benzene, toluene, xylene, tetramethylbenzene, etc.; alkyl amides such as N,N-dimethylformamide, N,N-dibutylformamide, N,N-dimethylacetamide, N-methylpyrrolidone, etc.; alcohols such as methanol, ethanol, propanol, butanol, etc.; glycol ethers (cellosolve) such as ethyleneglycol monoethyl ether, ethyleneglycol monomethyl ether, ethyleneglycol monobutyl ether, diethyleneglycol monoethyl ether, diethyleneglycol monomethyl ether, diethyleneglycol monobutyl ether, propyleneglycol monomethyl ether, propyleneglycol monoethyl ether, dipropyleneglycol diethyl ether, triethyleneglycol monoethyl ether, etc.; others such as dimethylacetamide (DMAc), N,N-diethylacetamide, dimethylformamide (DMF), diethylformamide (DEF), N,N-dimethylacetamide (DMAc), N-methylpyrrolidone (NMP), N-ethylpyrrolidone (NEP), 1,3-dimethyl-2-imidazolidinone, N,N-dimethylmethoxyacetamide, dimethyl sulfoxide, pyridine, dimethyl sulfone, hexamethylphosphoamide, tetramethylurea, N-methylcarrolactam, tetrahydrofuran, m-dioxane, P-dioxane, 1,2-dimethoxyethane and the like. Specifically, alcohol, more specifically methanol may be used, but it is not limited thereto.

The positively charging may be performed by reacting the porous silica particles with alkoxysilane having a basic group such as a nitrogen-containing group, for example, an amino group or an aminoalkyl group. Specifically, N-[3-(trimethoxysilyl)propyl]ethylenediamine, N1-(3-trimethoxysilylpropyl)diethylenetriamine, (3-aminopropyl)trimethoxysilane, N-[3-(trimethoxysilyl)propyl]aniline, trimethoxy[3-(methylamino)propyl]silane, 3-(2-aminoethylamino)propyldimethoxymethylsilane, etc. may be used, but it is not limited thereto.

The negatively charging may be performed by reacting the porous silica particles with alkoxysilane having an acidic group such as a carboxyl group, a sulfonic acid group, a thiol group, etc. Specifically, (3-Mercaptopropyl) trimethoxysilane may be used, but it is not limited thereto.

The hydrophilic property may be obtained by reacting the porous silica particles with alkoxysilane having a hydrophilic group, for example, hydroxyl group, carboxy group, amino group, carbonyl group, sulfhydryl group, phosphate group, thiol group, ammonium group, ester group, imide group, thioimide group, keto group, ether group, indene group, sulfonyl group, polyethyleneglycol group and the like. Specifically, N-[3-(trimethoxysilyl)propyl]ethylenediamine, N1-(3-trimethoxysilylpropyl)diethylenetriamine, (3-aminopropyl)trimethoxysilane, (3-mercaptopropyl) trimethoxysilane, trimethoxy[3-(methylamino)propyl]silane, 3-(2-aminoethylamino)propyldimethoxymethylsilane may be used, but it is not limited thereto.

The hydrophobic property may be obtained by reacting the porous silica particles with alkoxysilane having a hydrophobic substituent, for example, substituted or unsubstituted C1 to C30 alkyl group, substituted or unsubstituted C3 to C30 cycloalkyl group, substituted or unsubstituted C6 to C30 aryl group, substituted or unsubstituted C2 to C30 heteroaryl group, halogen group, C1 to C30 ester group, halogen-containing group and the like. Specifically, trimethoxy(octadecyl)silane, trimethoxy-n-octylsilane, trimethoxy(propyl)silane, isobutyl(trimethoxy)silane, trimethoxy(7-octen-1-yl)silane, trimethoxy(3,3,3-trifluoropropyl)silane, trimethoxy(2-phenylethyl)silane, vinyltrimethoxysilane, cyanomethyl, 3-(trimethoxysilyl)propyl] trithiocarbonate, (3-bromopropyl)trimethoxysilane, etc. may be used, but it is not limited thereto.

Further, in order to increase a binding ability of the silica particles to a poorly soluble (hydrophobic) antibody, cytokine or material through surface modification, hydrophobic substituents may be present inside of the pores of the particle. Further, in aspects of easy use and formulation, the surface of the particles may also be treated to have hydrophilic substituents. In addition, there may be a substituent on the surface of the particles in order to bind another antibody, cytokine or material.

Further, the surface modification may be performed in combination. For example, surface modification may be performed twice or more on the outer surface of the particles or the inside of the pores. As a specific example, a compound including a carboxyl group may be bound to silica particles having amino groups introduced therein through amide bond in order to change the positively-charged particles to have different surface properties, but it is not limited thereto.

The reaction of the porous silica particles with alkoxysilane may be carried out, for example, under heating. The heating may be conducted at 80 to 180° C., for example, 80 to 160° C., 80 to 150° C., 100 to 160° C., 100 to 150° C., 110 to 150° C., etc. within the above range, but it is not limited thereto.

The reaction of the porous silica particles with alkoxysilane may be carried out for 4 to 20 hours, for example, 4 to 18 hours, 4 to 16 hours, 6 to 18 hours, 6 to 16 hours, 8 to 18 hours, 8 to 16 hours, 8 to 14 hours, 10 to 14 hours, etc. within the above range, but it is not limited thereto.

The reaction temperature, time and an amount of the compound used for surface modification may be desirably selected according to an extent of surface modification, and reaction conditions will vary depending on hydrophilic property, hydrophobic property and a level of charge with regard to the antibody, cytokine or material of the present invention. By controlling the hydrophilic property, hydrophobic property and the level of charge of the porous silica particles, a release rate of an antibody, cytokine or material may be controlled. For example, if the antibody, cytokine or material have strong negative charge at neutral pH, the reaction temperature may be raised, the reaction time may be extended or the amount of the treated compound may be increased so as to make the porous silica particles to have strong positive charge, but it is not limited thereto.

Further, the porous silica particles of the present invention may be manufactured through, for example, preparation of small pore particles, pore expansion, surface modification, and internal pore modification.

Preparation of small pore particles and pore expansion may be performed by the above-described processes and, after preparation of the small pore particles and after pore expansion, washing and drying processes may be implemented.

If necessary, unreacted materials may be separated before washing, and separation of the unreacted materials may be conducted by separating the supernatant through centrifugation.

Centrifugation may be conducted at 6,000 to 10,000 rpm, and the centrifugation time may range from 3 to 60 minutes, for example, 3 to 30 minutes, 3 to 30 minutes, 5 to 30 minutes, etc. within the above range, but it is not limited thereto.

The washing after preparation of small pore particles may be conducted by a method/condition within the above-described range, but it is not limited thereto.

The washing after pore expansion may be conducted under more moderate conditions than the above embodiments. For example, washing may be conducted three times or less, but it is not limited thereto.

The surface modification and internal pore modification may be performed by the above-described processes, respectively. Herein, surface modification and then internal pore modification may be performed in this order, and a washing process may be further conducted between the above two processes.

When the washing is conducted in more moderated conditions after preparation of small pore particles and pore expansion, a reaction solution such as a surfactant used for particle production and pore expansion is filled in the pores so that the inside of the pores is not modified during surface modification and, instead, only the surface of the particles may be modified. Thereafter, the reaction solution inside of the pores may be washed out and removed.

Particle washing between the surface modification and the internal pore modification processes may be carried out using water and/or an organic solvent. Specifically, since different substances are dissolved in different solvents, water and the organic solvent may be used alternately once or several times, or the washing may be conducted with water or the organic solvent alone once or several times. The several times described above may be 2 times or more and 10 times or less, for example, 3 times or more and 10 times or less, 4 times or more and 8 times or less, 4 times or more and 6 times or less.

The washing may be carried out under centrifugation, for example at 6,000 to 10,000 rpm, and the centrifugation time may range from 3 to 60 minutes, for example, 3 to 30 minutes, 3 to 30 minutes, 5 to 30 minutes, etc. within the above range, but it is not limited thereto.

Alternatively, the washing may be conducted by filtering out particles through a filter without centrifugation. The filter may have pores in a size of less than or equal to the diameter of the porous silica particles. When filtering the reaction solution with such a filter as described above, only particles remain on the filter, which may be washed by pouring water and/or an organic solvent on the filter.

In the washing, water and the organic solvent may be used alternately once or several times, or the washing may be conducted with water or the organic solvent alone once or several times. The several times described above may be 2 times or more and 10 times or less, for example, 3 times or more and 10 times or less, 4 times or more and 8 times or less, 4 times or more and 6 times or less.

The drying may be conducted, for example, at 20 to 100° C., but it is not limited thereto, and may also be conducted in a vacuum state.

The antibody or cytokine may be supported on the surface of the porous silica particles and/or the inside of the pores.

Herein, the supporting may be performed, for example, by mixing porous silica particles in a solvent with the antibody or cytokine.

The solvent may be water and/or an organic solvent, and the solvent may include, for example: ethers such as 1,4-dioxane (particularly cyclic ethers); halogenated hydrocarbons such as chloroform, methylene chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methylisobutylketone, cyclohexanone, etc.; aromatic carbon-based materials such as benzene, toluene, xylene, etc.; alkyl amides such as N,N-dimethylformamide, N,N-dibutylformamide, N,N-dimethylacetamide, N-methylpyrrolidone, etc.; alcohols such as methanol, ethanol, propanol, butanol and the like. Specifically, alcohol, more specifically methanol may be used, but it is not limited thereto.

Further, PBS (phosphate buffered saline solution), SBF (simulated body fluid), borate-buffered saline, tris-buffered saline may be used as the solvent.

A relative ratio of the porous silica particles to the oligonucleotides of the present invention is not particularly limited but may be 1:0.05 to 0.8 in weight ratio, for example, 1:0.05 to 0.7, 1:0.05 to 0.6, 1:0.1 to 0.8, 1:0.1 to 0.6, 1:0.2 to 0.8, 1:0.2 to 0.6, etc. within the above range.

The antibody or cytokine supported on the porous silica particles may be gradually released over an extended time. Such sustained release may be continuous or discontinuous, or linear or nonlinear. Further, the release may vary depending upon characteristics of the porous silica particles and/or interaction between the porous silica particles and the antibody or cytokine.

The antibody or cytokine supported on the porous silica particles are released when the porous silica particles are biodegraded. Specifically, the porous silica particles according to the present invention are slowly degraded to allow release of the antibody or cytokine in a sustained manner. Such release may be controlled by, for example, adjusting surface area, particle size, pore diameter, substituents on the surface of the particles and/or the inside of the pores, surface compactness, etc. with regard to the porous silica particles, but it is not limited thereto.

The antibody or cytokine supported on the porous silica particles may be released while being separated and diffused from the porous silica particles. Such release is influenced by correlations between the porous silica particles, the antibody or cytokine, and release environment of the same. Therefore, regulating the correlations may control the release of the antibody or cytokine. For example, by enhancing or weakening a binding force of the porous silica particles to the antibody or cytokine through surface modification, the release of the antibody or cytokine may be controlled.

More specifically, in the case where the supported antibody, cytokine or material are poorly soluble (hydrophobic), the surface of the particles and/or the inside of the pores have hydrophobic substituents so as to increase a binding force of the porous silica particles to the antibody, cytokine or material, whereby the antibody, cytokine or material may be released in a sustained manner. For example, the porous silica particles may be surface-modified with alkoxysilane having a hydrophobic substituent.

As used herein, the term "poorly soluble" means to be insoluble, practically insoluble or only slightly soluble (in water), which is a word defined in "Pharmaceutical Science" 18$^{th}$ Edition (issued by U.S.P., Remington, Mack Publishing Company).

The poorly soluble material may have, for example, water solubility of less than 10 g/L, specifically, less than 5 g/L, and more specifically, less than 1 g/L at 1 atmosphere and 25° C., but it is not limited thereto.

When the supported antibody, cytokine or material is water-soluble (hydrophilic), the surface of the particles and/or the inside of the pores have hydrophilic substituents so as to increase a binding force of the porous silica particles to the antibody, cytokine or material, whereby the antibody, cytokine or material may be released in a sustained manner. For example, the porous silica particles may be surface-modified with alkoxysilane having a hydrophilic substituent.

For example, the water-soluble material may have a water solubility of 10 g/L or more at 1 atmosphere and 25° C., but it is not limited thereto.

In the case where the supported antibody, cytokine or material is charged, the surface of the particles and/or the inside of the pores are charged with opposite charges, so as to increase the binding force of the porous silica particles to the antibody, cytokine or material, whereby the antibody, cytokine or material may be released in a sustained manner. For example, the porous silica particles may be surface-modified with alkoxysilane having an acidic group or a basic group.

Specifically, if the antibody, cytokine or material is positively charged at neutral pH, the surface of the particles and/or the inside of the pores may be negatively charged at neutral pH so as to increase a binding force of the porous silica particles to the antibody, cytokine or material, whereby the antibody, cytokine or material may be released in a sustained manner. For example, the porous silica particles may be surface-modified with alkoxysilane having an acidic group such as a carboxyl group (—COOH), a sulfonic acid group (~SO3H), etc.

Further, if the antibody, cytokine or material is negatively charged at neutral pH, the surface of the particles and/or the inside of the pores may be positively charged at neutral pH, so as to increase a binding force of the porous silica particles to the antibody, cytokine or material, whereby the antibody, cytokine or material may be released in a sustained manner. For example, the porous silica particles may be surface-modified with alkoxysilane having a basic group such as an amino group or any other nitrogen-containing group.

The antibody, cytokine or material may be released for a period of, for example, 7 days to 1 year or more, depending upon types of treatment to be required, release environments and types of porous silica particles to be used.

Further, since the porous silica particles of the present invention are 100% biodegradable, the antibody, cytokine or material may be 100% released.

The present invention provides an immunotherapeutic composition, including the carrier described above.

Immunotherapy refers to planning of patient treatment by immunological methods, and may include specific immunotherapy involving only immune response to specific antigens and nonspecific immunotherapy effective for the entire immune system without limitation of specific antigens. The specific immunotherapy may include a method of administering an antibody, while a representative example of the nonspecific immunotherapy may include a method of administering cytokines.

The immunotherapeutic composition of the present invention may include porous silica particles that carry an immunoreactive substance containing the above-described antibody or cytokine, and can stably deliver the loaded immunoreactive substance into the body in a sustained manner. Further, the composition has effective superiority to reduce inherent side effects of the immunoreactive substance and may be used in immunotherapy so as to achieve excellent effects in prevention or treatment of various cancers or immune diseases.

The cancer described above may include any one selected from the group consisting of: carcinoma such as bladder cancer, breast cancer, colon cancer, kidney cancer, liver cancer, lung cancer, ovarian cancer, prostate cancer, pancreatic cancer, gastric cancer, cervical cancer, thyroid cancer and skin cancer including squamous cell carcinoma; lymphoid hematopoietic tumors such as leukemia, acute lymphocytic leukemia, acute lymphocytic leukemia, B-cell lymphoma, T-cell lymphoma, Hodgkins lymphoma, non-Hodgkins lymphoma, hairy cell lymphoma and Bucket lymphoma; myeloid hematopoietic tumors such as acute and chronic myeloid leukemia and promyelocytic leukemia; mesenchymal-derived tumors such as fibrosarcoma and rhabdomyosarcoma; other tumors such as melanoma, seminoma, teratocarcinoma, neuroblastoma and glioma; tumors of the central and peripheral nervous system such as astrocytoma, neuroblastoma, glioma and schhwannoma; mesenchymal-derived tumors such as fibrosarcoma, rhabdomyosarcoma, and osteosarcoma; and other tumors such as melanoma, xeroderma pigmentosum, kerotoacanthoma, seminoma, thyroid follicular cancers, and teratocarcinoma.

The immune disease refers to a disease in which components of the mammalian immune system cause, mediate or contribute to pathology of the mammals, and all diseases in which the stimulation or interruption of an immune response has compensatory effects on the progression of the disease. Further, all autoimmune diseases, infectious diseases, inflammatory diseases or transplant rejection diseases of cells, tissues or organs, and the like, may be included. Specifically, Behcet's disease, multiple myositis/skin myositis, autologous diseases such as autoimmunocytopenia, autoimmune myocarditis, atopic dermatitis, asthma, primary cirrhosis, dermatitis, Goodpasture's syndrome, autoimmune meningitis, obesity, Sjogren's syndrome, ankylosing spondylitis, systemic lupus erythematosus, Addison's disease, alopecia areata, autoimmune hepatitis, autoimmune mumps, Crohn's disease, insulin dependent diabetes mellitus, dystrophic bullous epidermal detachment, epididymitis, glomerulonephritis, Graves' disease, Guillain-Barré syndrome, Hashimoto's disease, hemolytic anemia, multiple sclerosis, myasthenia gravis, vulgaris, psoriasis, rheumatic fever, rheumatoid arthritis, sarcoidosis, scleroderma, spondyloarthropathy, thyroiditis, vasculitis, vitiligo, myxedema, pernicious anemia, ulcerative colitis, and the like.

Autoimmune diseases as one type of the immune disease are not limited to types thereof, but may include Crohn's disease, erythema, atopicallergy, rheumatoid arthritis, Hashimoto's thyroiditis, pernicious anemia, Edison's disease, type 1 diabetes, lupus, chronic fatigue syndrome, fiber myalgia, hypothyroidism and hyperplasia, scleroderma, Behcet's disease, inflammatory bowel disease, multiple sclerosis, myasthenia gravis, Meniere's syndrome, Guilian-Barre syndrome, Sjogren's syndrome, vitiligo, endometriosis, psoriasis, systemic scleroderma, asthma or ulcerative colitis.

The infectious disease as one type of the immune diseases may be an infectious disease caused by bacteria, parasites, fungi, viruses, viroids and prions.

The virus may be enterovirus, rotorvirus, adenovirus and hepatitis virus. In addition to the above viruses, retroviridae (e.g., human immunodeficiency viruses such as HIV-I (also referred to as HTLV-III, LAV or HTLV-III/LAV, or HIV-III); and other isolates such as HIV-LP); Picornaviridae (e.g., polio virus, hepatitis A virus, enterovirus, human Coxsackie virus, rhinovirus, echovirus); Calciviridae (e.g., species to cause gastroenteritis); Togaviridae (e.g., equine encephalitis virus, rubella virus); Flaviviridae (e.g., dengue virus, encephalitis virus, yellow fever virus); Coronaviridae (e.g., coronavirus); Rhabdoviridae (e.g., vesicular stomatitis virus, rabies virus); Phylloviridae (eg, ebola virus); Pararamyxoviridae (e.g., parainfluenza virus, mumps virus, measles virus, respiratory syncytial virus); Orthomyxoviridae (e.g., influenza virus); Bunyaviridae (e.g., Hantaan virus, bunya virus, phlebovirus and Nairo virus); Arenaviraceae (hemorrhagic fever virus); Reoviridae (e.g., reovirus, orbivirus and rotavirus); Bornaviridae; Hepadnaviridae (Hepatitis B virus); Parvooviridae (Parvoviridae); Papovaviridae (papilloma virus, polyoma virus); Adenoviridae (most Adenoviruses); Herpesviridae (herpes simplex virus (HSV) 1 and 2, varicella zoster virus, cytomegalovirus (CMV), herpes virus); Poxviridae (Variola virus, vaccinia virus. Pox virus); Iridoviridae (e.g., African swine fever virus); unclassified viruses (e.g., delta hepatitis (presumed to be a satellite deficient in hepatitis B), hepatitis C); and Norwalk and related viruses, and formulatios of astro virus may also be included, but it is not limited thereto.

The present invention also provides a pharmaceutical composition for prevention or treatment of cancers or immune diseases, including the above-described carrier.

The composition of the present invention has prophylactic or therapeutic effects of cancers or immune diseases, which are achieved by stably delivering the loaded antibody or cytokine into the body and releasing the same to a target in a sustained manner so as to suppress the growth of cancer (or tumor) and inhibit the transition thereof.

The pharmaceutical composition of the present invention may further include a pharmaceutically acceptable carrier, and may be formulated along with such a carrier. As used herein, the term "pharmaceutically acceptable carrier" refers to a carrier or diluent that does not stimulate the organism and does not inhibit biological activities and properties of the administered compound. Pharmaceutical carriers acceptable in the composition formulated as a liquid solution are sterile and biocompatible, and may include saline, sterile water, Ringer's solution, buffered saline, albumin injectable solutions, dextrose solution, maltodextrin solution, glycerol, ethanol, and a mixture of one or more of these components. Further, if necessary, other typical additives such as antioxidants, buffers and bacteriostatic agents may be added. Diluents, dispersants, surfactants, binders and lubricants may also be added to formulate the pharmaceutical composition into injectable formulations, pills, capsules, granules or tablets such as aqueous solutions, suspensions, emulsions and the like.

The pharmaceutical composition of the present invention is applicable in a form of any formulation containing the carrier of the present invention as an active ingredient, and may be prepared in oral or parenteral formulations. The pharmaceutical formulations of the present invention may include forms suitable for oral, rectal, nasal, topical (including the cheek and sublingual), subcutaneous, vaginal or parenteral (intramuscular, subcutaneous) administration. Alternatively, forms suitable for administration by inhalation or insufflations may also be included.

The pharmaceutical composition of the present invention is administered in a pharmaceutically effective amount. Effective dose levels may be determined depending on types of disease of the patient, severity, activity of drug, sensitivity to drug, administration time, administration route and rate of release, duration of treatment, factors including concurrent medications, and other factors well known in the medical field. The pharmaceutical composition of the present invention may be administered as an individual therapeutic agent or in combination with other therapeutic agents, may be administered sequentially or simultaneously with conventional therapeutic agents, and may be administered in single or multiple doses. Taking all of the above factors into consideration, it is important to administer the pharmaceutical composition in an amount that can achieve maximum effects with a minimum amount without side effects, which may be easily determined by those skilled in the art.

The dosage of the pharmaceutical composition according to the present invention may vary widely depending on the weight, age, sex, health conditions or diet of a patient, administration time, administration method, excretion rate and severity of the disease, and the appropriate dosage depends on, for example, an amount of drug accumulated in the patient's body and/or specific efficacy of the carrier of the present invention used. Generally, the amount may be calculated on the basis of EC50, which is generally determined to be effective in in vivo animal models and in vitro, for example, from 0.01 µg to 1 µg per kg of body weight. Further, the pharmaceutical composition of the present invention may be administered once or several times per unit time during unit periods of time such as daily, weekly, monthly or yearly, or may be continuously administered using an infusion pump for a long time. The number of repeated administration doses is determined in consideration of a residential time of drug in the body, a drug concentration in the body, etc. Even after treatment according to the course of disease treatment, the composition may be further administered for preventing recurrence, i.e., relapse of the disease.

The pharmaceutical composition of the present invention may further include a compound to maintain/increase one or more of active ingredients exhibiting the same or similar functions in relation to treatment of fibroproliferative diseases or the solubility and/or absorption of at least one active ingredient. Further, the composition may also optionally include chemotherapeutic agents, anti-inflammatory agents, antiviral agents and/or immunomodulators and the like.

Further, the pharmaceutical composition of the present invention may be formulated using any method known in the art to allow rapid, sustained or delayed release of the active ingredient after the administration to a mammal. The formulation may be produced in a form of powders, granules, tablets, emulsions, syrups, aerosols, soft or hard gelatin capsules, sterile injectable solutions, sterile powders.

Specific description related to cancer and immune diseases subjected to the afore-mentioned prevention or treatment is the same as described above.

Hereinafter, the present invention will be described in detail with reference to the following examples.

Hereinafter, porous silica particles of the present invention may be abbreviated as 'DEGRADABALL or DDV', and DEGRADABALL carrying IL-2 may be abbreviated as 'BALLkine-2'.

Hereinafter, peri-tumoral injection may be abbreviated as 'p.t', intra-peritoreal injection may be abbreviated as 'i.p,' subcutaneous injection may be abbreviated as 's.c,' and intravenous injection may be abbreviated as 'i.v.'

Example 1. Porous Silica Particles (DDV or DEGRADABALL)

1. Preparation of Porous Silica Particles (1) Preparation of Porous Silica Particles 1) Preparation of Small Pore Particles 960 mL of distilled water (DW) and 810 mL of MeOH were put into a 2 L round bottom flask. 7.88 µg of CTAB was added to the flask, followed by rapid addition of 4.52 mL of 1 M NaOH under stirring. After adding a homogeneous mixture while stirring for 10 minutes, 2.6 mL of TMOS was further added. After stirring for 6 hours to mix uniformly, the reaction solution was aged for 24 hours.

Then, the reaction solution was centrifuged at 8000 rpm and 25° C. for 10 minutes to remove the supernatant, centrifuged at 8000 rpm and 25° C. for 10 minutes, and washed five times with ethanol and distilled water alternately.

Thereafter, the resultant product was dried in an oven at 70° C. to harvest 1.5 µg of powdery microporous silica particles (pore average diameter of 2 nm and particle size of 200 nm).

2) Pore Expansion 1.5 µg of microporous silica particle powder was added to 10 ml of ethanol and subjected to ultrasonic dispersion, and 10 ml of water and 10 ml of TMB (trimethyl benzene) were further added, followed by ultrasonic dispersion.

Thereafter, the dispersion was placed in an autoclave and reacted at 160° C. for 48 hours.

The reaction was initiated at 25° C. and performed while raising the temperature at a rate of 10° C./min, then slowly cooled in an autoclave at a rate of 1 to 10° C./min.

The cooled reaction solution was centrifuged at 8000 rpm for 10 minutes at 25° C. to remove the supernatant, and centrifuged at 8000 rpm for 10 minutes at 25° C. and washed five times with ethanol and distilled water alternately.

Then, the product was dried in an oven at 70° C. to harvest powdery porous silica particles (pore diameter of 10 to 15 nm, and particle size of 200 nm).

3) Calcination

The porous silica particles prepared in 2) were put in a glass vial, heated at 550° C. for 5 hours, and cooled slowly to room temperature after completing the reaction to prepare particles.

(2) Preparation of Porous Silica Particles

Porous silica particles were prepared by the same method as Example 1-1-(1), except that the reaction conditions at the time of pore expansion were changed to 140° C. and 72 hours.

(3) Preparation of Porous Silica Particles (10 L Scale)

Porous silica particles were prepared by the same method as Example 1-1-(1), except that a 5 times larger container was used and each material was used in a 5 times capacity.

(4) Preparation of Porous Silica Particles (Particle Size of 300 nm)

Porous silica particles were prepared by the same method as Example 1-1-(1), except that 920 ml of distilled water and 850 ml of methanol were used to prepare the small pore particles.

(5) Preparation of Porous Silica Particles (Particle Size of 500 nm)

Porous silica particles were prepared by the same method as Example 1-1-(1), except that 800 ml of distilled water, 1010 ml of methanol, and 10.6 µg of CTAB were used to prepare the small pore particles.

(6) Preparation of Porous Silica Particles (Particle Size of 1000 nm)

Porous silica particles were prepared by the same method as Example 1-1-(1), except that 620 ml of distilled water, 1380 ml of methanol, and 7.88 µg of CTAB were used to prepare the small pore particles.

(7) Preparation of Porous Silica Particles (Pore Diameter of 4 nm)

Porous silica particles were prepared by the same method as Example 1-1-(1), except that 2.5 mL of TMB was used for pore expansion.

(8) Preparation of Porous Silica Particles (Pore Diameter of 7 nm)

Porous silica particles were prepared by the same method as Example 1-1-(1), except that 4.5 mL of TMB was used for pore expansion.

(9) Preparation of Porous Silica Particles (Pore Diameter of 17 nm)

Porous silica particles were prepared by the same method as Example 1-1-(1), except that 11 mL of TMB was used for pore expansion.

(10) Preparation of Porous Silica Particles (Pore Diameter of 23 nm)

Porous silica particles were prepared by the same method as Example 1-1-(1), except that 12.5 mL of TMB was used for pore expansion.

(11) Preparation of Porous Silica Particles (Dual Modification)

1) Preparation of Small Pore Particles
Small pore particles were prepared by the same method as Example 1-1-(1)-1).
2) Pore Expansion
Small pore particles were reacted with TMB, cooled and centrifuged by the same method as Example 1-1-(1)-2) to remove the supernatant. Thereafter, the remaining solution was centrifuged under the same conditions as Example 1-1-(1)-2), washed three times with ethanol and distilled water alternately, and then dried under the same conditions as Example 1-1-(1)-2), thereby harvesting powdery porous silica particles (pore diameter 10 to 15 nm, and particle size of 200 nm).
3) Surface Modification
After dispersing 0.8 µg to 1 µg of porous silica particles having expanded pores in 50 mL of toluene, 5 mL of (3-aminopropyl)triethoxysilane was added thereto, followed by heating under reflux at 120° C. for 12 hours. The procedure is followed by the washing and drying procedures described above, followed by 1 mL of triethylene glycol (PEG3, 2-[2-(2-methoxyethoxy)ethoxy]acetic acid) and 100 mg of EDC (1-ethyl-3-(3-dimethylaminopropyl)carbodiimide) and 200 mg of N-hydroxysuccinimide (NHS) were dispersed in 30 mL of PBS and allowed to react at room temperature for 12 hours under stirring. The product was then washed and dried.

Since the reaction solution of the previous step remained inside of the pores, the inside of the pores was not modified.
4) Washing Inside Pores
800 mg of surface-modified particle powder was dissolved in 40 ml of 2M HCl/ethanol and refluxed under vigorous stirring for 12 hours.

Thereafter, the cooled reaction solution was centrifuged at 8000 rpm for 10 minutes to remove the supernatant, centrifuged at 8000 rpm and 25° C. for 10 minutes, and washed five times with ethanol and distilled water alternately.

Thereafter, the product was dried in an oven at 70° C., thereby harvesting powdery porous silica particles.
5) Modifying Inside Pores
① A propyl group was introduced into the pore in the same manner as the method of Example 1-2-(2)-1) described below.
② An octyl group was introduced into the pore in the same manner as the method of Example 1-2-(2)-2) described below.

2. Surface Modification of Porous Silica Particles

(1) Positively Charging

1) Particles with Particle Size of 300 nm
The porous silica particles of Example 1-1-(4) were reacted with (3-aminopropyl)triethoxysilane (APTES) to be positively charged.

Specifically, 100 mg of porous silica particles were dispersed in a 10 mL toluene in a 100 mL round bottom flask with a bath sonicator. Then, 1 mL of APTES was added and stirred at 400 rpm and 130° C. for 12 hours.

After the reaction, the product was slowly cooled to room temperature and centrifuged at 8000 rpm for 10 minutes to remove the supernatant, further centrifuged at 8000 rpm and 25° C. for 10 minutes, and then washed five times with ethanol and distilled water alternately.

Thereafter, the product was dried in an oven at 70° C. to harvest powdery porous silica particles having an amino group on the surface thereof and inside of the pores.
2) Particles with Particle Size of 200 nm
① The porous silica particles of Example 1-1-(1) were positively charged by reacting the particles with (3-aminopropyl)triethoxysilane (APTES), and were modified in the same manner as the method of Example 1-2-(1)-1), except that 0.4 ml of APTES was added and the reaction time was 3 hours.
② The porous silica particles of Example 1-1-(9) were positively charged by reacting the particles with (3-aminopropyl)triethoxysilane (APTES), and were modified in the same manner as the method of Example 1-2-(1)-1).
③ The porous silica particles of Example 1-1-(10) were positively charged by reacting the particles with (3-aminopropyl)triethoxysilane (APTES), and were modified in the same manner as the method of Example 1-2-(1)-1).

(2) Introduction of Hydrophobic Groups

1) Propyl Group
The porous silica particles of Example 1-1-(1) were reacted with trimethoxy(propyl)silane to introduce propyl groups into the surface of the particles and inside of the pores, and were subjected to modification by the same method as Example 1-2-(1), except that 0.35 ml of trimethoxy(propyl)silane was added instead of APTES, followed by 12 hours of reaction.

2) Octyl Group

The porous silica particles of Example 1-1-(1) were reacted with trimethoxy-n-octylsilane to introduce propyl groups on the surface of the particles and inside of the pores, and were subjected to modification by the same method as Example 1-2-(1), except that 0.5 ml of trimethoxy-n-octylsilane was added instead of APTES, followed by 12 hours of reaction.

(3) Negatively Charging

1) Carboxyl Group

The porous silica particles of Example 1-1-(1) were negatively charged by reacting the particles with succinic anhydride.

Further, the charged particles were subjected to modification in the same manner as the method of Example 1-2-(1)-1), except that DMSO (dimethyl sulfoxide) was used instead of toluene, 80 mg of succinic anhydride was added instead of APTES to allow reaction at room temperature for 24 hours under stirring, and DMSO was used instead of distilled water.

2) Thiol Group

The particles were subjected to modification in the same manner as the method of Example 1-2-(1)-1), except that 1.1 mL of MPTES was used instead of APTES.

3) Sulfonic Acid Group 100 mg of the porous silica nanoparticles of Example 1-2-(3)-2) were dispersed in 1 mL of 1 M aqueous sulfuric acid solution and 20 mL of 30% hydrogen peroxide solution, and stirred at room temperature to induce oxidation, thereby oxidizing a thiol group into a sulfonic acid group. Thereafter, the product was washed and dried in the same manner as the method of Example 1-2-(1)-1).

3. Identification of Particle Formation and Pore Expansion

Small pore particles and porous silica particles prepared in Experimental Examples 1-1-(1) to (3) were observed under a microscope to determine whether the small pore particles were uniformly formed or the pores were sufficiently expanded to uniformly form the porous silica particles (FIGS. 1 to 4).

Figure 1:
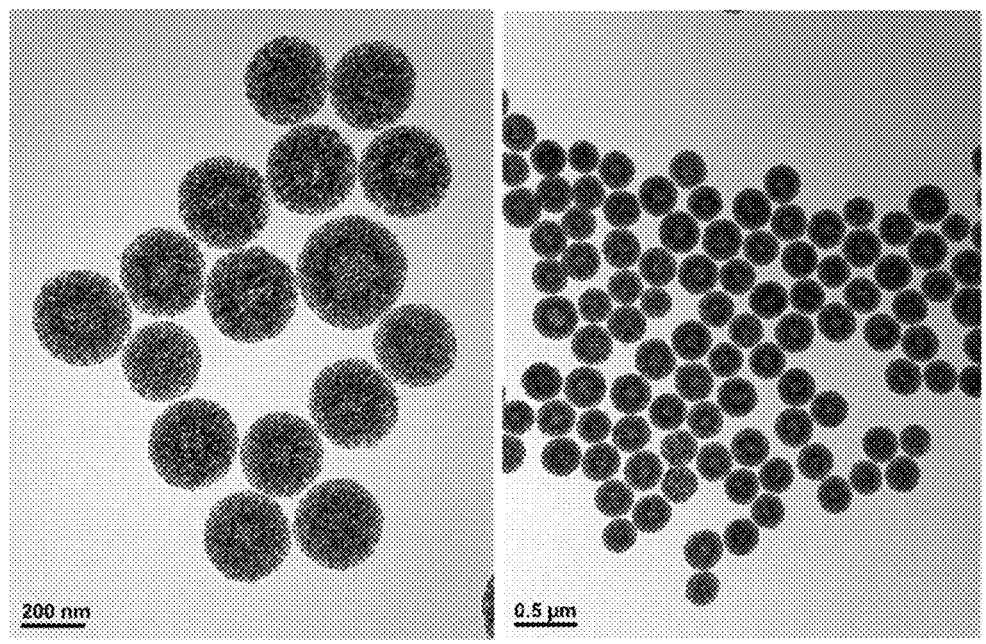
FIG. 1 is diagrams illustrating MS analysis values of the synthesized SLIGRL peptide.
Figure 2:
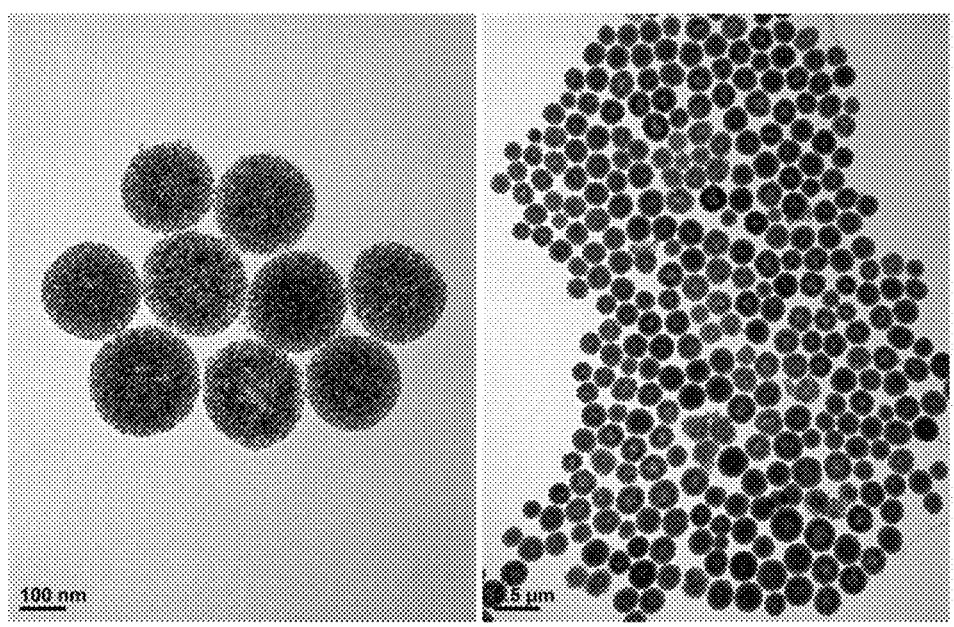
FIG. 2 is micrographs of porous silica particles according to one embodiment of the present invention.

FIG. 1 is photographs of the porous silica particles in Experimental Example 1-1-(1), and FIG. 2 is photographs of the porous silica particles in Experimental Example 1-1-(2), and from these drawings, it can be seen that spherical porous silica particles having sufficiently expanded pores were formed evenly.

Figure 3:
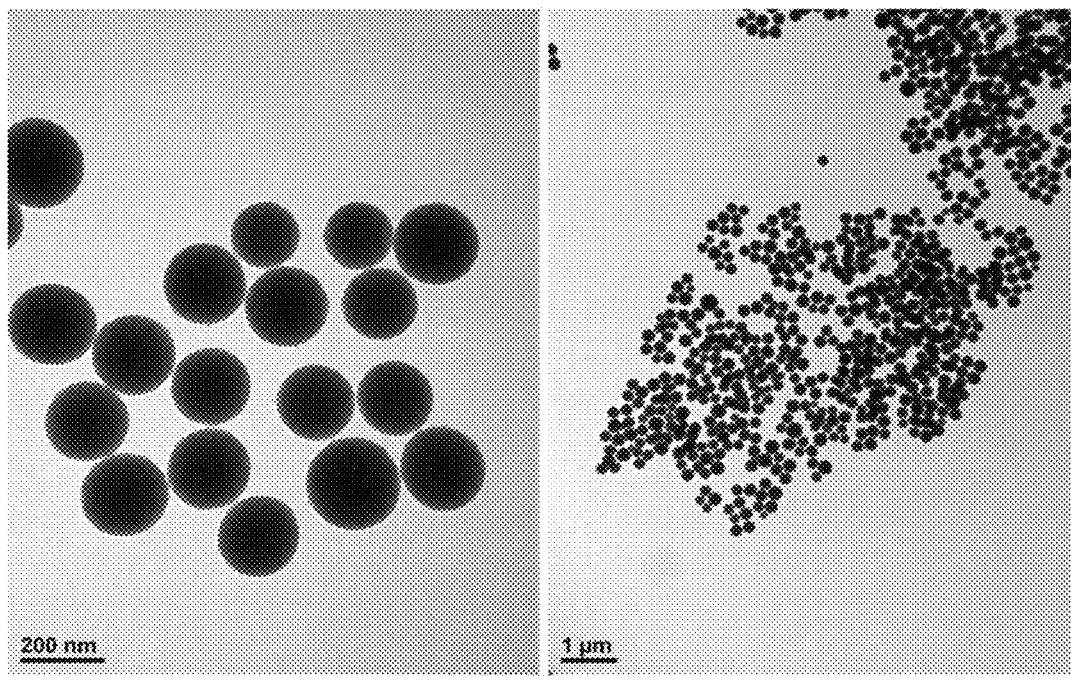
FIG. 3 is micrographs of porous silica particles according one embodiment of the present invention.
Figure 4:
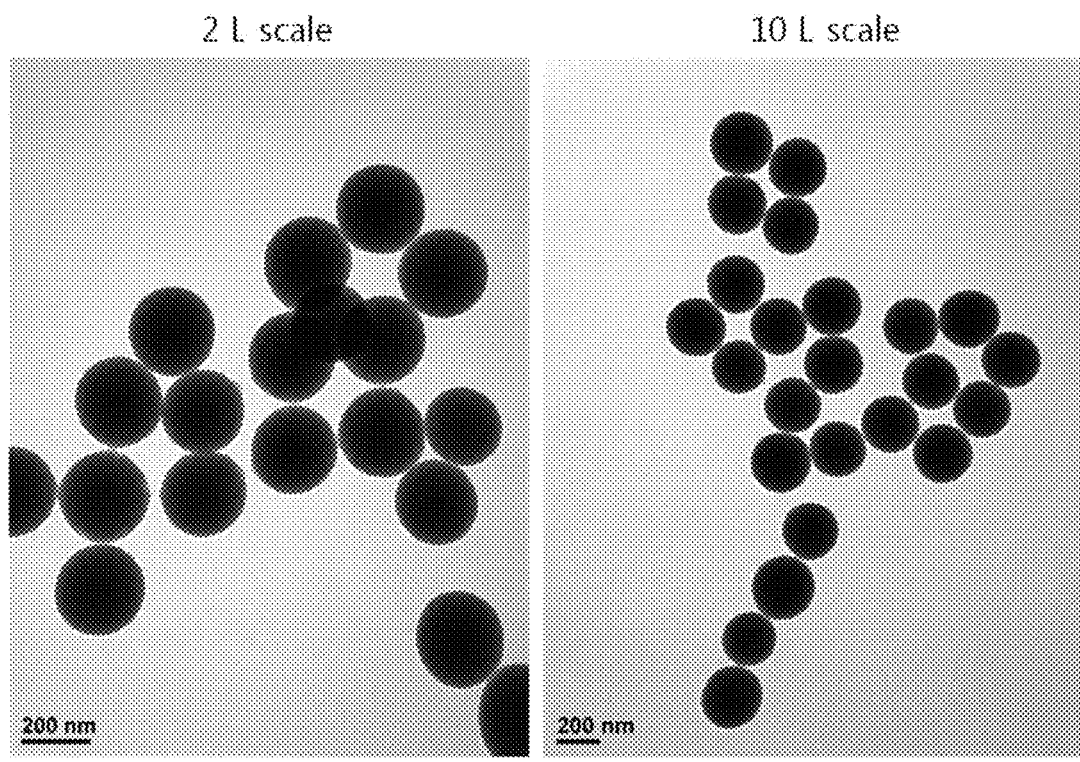
FIG. 4 is micrographs of small pore particles obtained in a manufacturing process of the porous silica particles according to one embodiment of the present invention.

FIG. 3 is photographs of the small pore particles in Experimental Example 1-1-(1), and FIG. 4 is a comparative photograph of the small pore particles in Experimental Examples 1-1-(1) and 1-1-(3), and from these drawings, it can be seen that spherical small pore particles were formed evenly.

4. Calculation of BET Surface Area and Pore Volume

The surface area and pore volume of the small pore particles in Experimental Example 1-1-(1) and the porous silica particles of Experimental Examples 1-1-(1), (7), (8) and (10) were calculated. The surface area was calculated by Brunauer-Emmett-Teller (BET) method, and the pore size distribution was calculated by Barrett-Joyner-Halenda (BJH) method.

Figure 5:
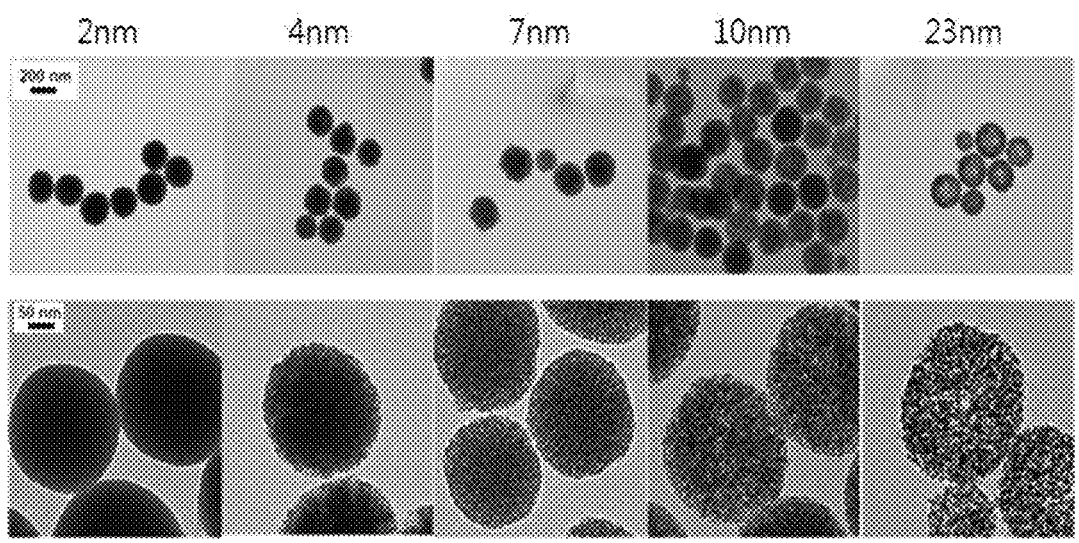
FIG. 5 is micrographs of the small pore particles according to one embodiment of the present invention.

Micrographs of the particles are shown in FIG. 5, and the calculation results are shown in Table 1 below.

TABLE 1

| Section | Pore diameter (nm) | BET surface area ($m^2/g$) | Pore volume (mL/g) |
|---|---|---|---|
| Small pore particles in Example 1-1-(1) | 2.1 | 1337 | 0.69 |
| Example 1-1-(7) | 4.3 | 630 | 0.72 |
| Example 1-1-(8) | 6.9 | 521 | 0.79 |
| Example 1-1-(1) | 10.4 | 486 | 0.82 |
| Example 1-1-(10) | 23 | 395 | 0.97 |

5. Identification of Biodegradability

In order to identify biodegradability of the porous silica particles in Experimental Example 1-1-(1), biodegradability at 37° C. in SBF (pH 7.4) was observed under a microscope at 0 hours, 120 hours and 360 hours, and results thereof are shown in FIG. 6.

Referring to FIG. 6, it could be seen that the porous silica particles are biodegraded and almost degraded after 360 hours.

6. Measurement of Absorbance Ratio

Absorbance ratio over time was measured according to Equation 1 below.

$$A_t/A_0$$ [Equation 1]

(wherein $A_0$ is absorbance of the porous silica particles measured by putting 5 ml of suspension containing 1 mg/ml of the porous silica particles into a cylindrical permeable membrane having pores with a pore diameter of 50 kDa, 15 ml of the same solvent as the suspension comes into contact with an outside of the permeable membrane, and the inside/outside of the permeable membrane are horizontally stirred at 60 rpm and 37° C., and $A_t$ indicates absorbance of the porous silica particles measured after lapse of "t" hours since $A_0$ was measured).

Specifically, 5 mg of porous silica particle powder was dissolved in 5 ml of SBF (pH 7.4). Thereafter, 5 ml of porous silica particle solution was placed in a permeable membrane having pores with a pore diameter of 50 kDa shown in FIG. 7. 15 ml of SBF was added to the outer membrane, and the SBF on the outer membrane was replaced every 12 hours. Degradation of the porous silica particles was performed at 37° C. under horizontal stirring at 60 rpm.

Then, the absorbance was measured by UV-vis spectroscopy and analyzed at λ=640 nm.

(1) Measurement of Absorbance Ratio

Absorbance ratio of the porous silica particles in Experimental Example 1-1-(1) was measured according to the above method, and results thereof are shown in FIG. 8.

Referring to FIG. 8, it can be seen that t, at which the absorbance ratio becomes ½, is about 58 hours to demonstrate very slow degradation.

(2) Particle Size

Absorbances of the porous silica particles in Experimental Examples 1-1-(1), (5), and (6) were measured according to Equation 1 above, and results thereof are shown in FIG. 9 (SBF used as the suspension and the solvent).

Referring to FIG. 9, it can be seen that t is decreased as the particle size is increased.

(3) Average Pore Diameter

Absorbances of the porous silica particles in Experimental Examples 1-1-(1) and (9) and the microporous silica particles in Experimental Example 1-1-(1) as a control were measured according to Equation 1 above, and results thereof are shown in FIG. 10 (SBF used as the suspension and the solvent).

Referring to FIG. 10, it can be seen that the porous silica particles of the inventive example have a significantly larger t than the control.

(4) pH

Absorbance of the porous silica particles in Experimental Example 1-1-(4) for each pH was measured. The absorbance was measured in SBF and in Tris at pH 2, 5, and 7.4, and results thereof are shown in FIG. 11.

Referring to FIG. 11, it could be seen that, although there is a difference in t in relation to pH, t at which all absorbance ratio becomes ½ was 24 or more.

(5) Charging

Absorbance of the porous silica particles in Experimental Example 1-2-(1)-1) was measured, and results thereof are shown in FIG. 12 (Tris (pH 7.4) used as the suspension and the solvent).

Referring to FIG. 12, it could be seen that t at which the absorbance ratio of the positively charged particles becomes ½ was 24 or more.

7. Loading of Antibody or Cytokine

(1) Loading of Antibody

100 µg of the porous silica particle powder of Example 1-2-(1)-2)-② and 10 µg of anti-twist IgG (Santacruz, sc-81417) were mixed in 200 µl of 1×PBS, and then, incubated at room temperature for 1 hour to carry IgG. Other antibodies were also loaded under the same conditions as above.

(2) Loading of Cytokine

After mixing 25 µg of the porous silica particle powder of Example 1-2-(1)-2)-② and 10 µg of IL-2 in 100 µL of PBS or distilled water, and then, incubated for 1 hour to carry IL-2. Other cytokines were also loaded under the same conditions as above.

8. Release of Antibody or Cytokine

(1) Release of Antibody

100 µg of porous silica particles loaded with Fluorescein fluorescence-labeled IgG were resuspended in 200 µl SBF (pH 7.4) or PBS (pH 7.4).

Release of IgG, PD-1 or PD-L1 was performed at 37° C. while horizontally stirring at 60 rpm, and 200 µl of the release solvent was recovered at 6, 12, 24, 48, 96, 144 and 240 hours for fluorescence measurement, and an equivalent amount of SBF or PBS was added. A fluorescence intensity of Fluorescein fluorescence-labeled IgG was measured at 517 nm wavelength ($\lambda_{ex}$=492 nm) to determine a degree of emission of BSA.

Referring to FIGS. 13 to 15, IgG was released in both SBF and PBS in a sustained manner, and it can be seen that all IgG, PD-1 and PD-L1 are released to almost 100% over 250 hours or more.

(2) Release of Cytokine

Porous silica particles carrying FITC-bound cytokines were resuspended in SBF (pH 7.4) at 37° C., and then observed for a predetermined period (1, 2, 3, 4, 5, 6, 7 days). The solution was centrifuged at 8,000 rpm for 10 minutes, and the release of cytokines was confirmed by fluorescence intensity spectra of FITC.

Referring to FIGS. 17 to 21, it can be seen that all IL-10, IL-15, HGF, EGF and IL-2 are released in a sustained manner to almost 100% over 7 hours or more.

Example 2. Identification of Toxicity of Porous Silica Particles

1. Experimental Method

In order to identify single dose toxicity of the porous silica particles of the present invention, 31.25, 62.5, 125 and 250 mg/kg of porous silica particles (DEGRADABALL) were respectively administered to all mice (4 per group), and 5 days after the administration, the mice were sacrificed to isolate major organs (liver, spleen, lung, heart and kidney).

In order to identify repeated dose toxicity of the porous silica particles of the present invention, 0.5, 5 and 50 mg/kg of porous silica particles (DEGRADABALL) were subcutaneously administered up to 9 times every 3 or 4 days to all mice (8 per group). 48 hours after the last administration, all mice were sacrificed to isolate the major organs (liver, spleen, lung, heart and kidney).

2. Experimental Result

Referring to FIGS. 22 to 43, it can be seen that clear pathological or clinical signs of toxicity are not observed in all groups. More specifically, the porous silica particles of the present invention did not induce significant weight loss of the organs (liver, spleen, kidney, thymus, heart, lung and lymph nodes) (data are expressed as mean±standard deviation; significant difference value from the normal group ($p<0.05$)). Further, with regard to various parameters obtained by whole blood analysis and serum biochemical analysis, red blood cell (RBC), white blood cell (WBC) and blood cell volume (i.e., average particulate volume (MCV)), average platelet volume (MPV), average particulate hemoglobin concentration (MCHC), hemoglobin, hematocrit and erythrocyte distribution width (RDW) levels were demonstrated to be within normal ranges, and there was no sign of hepatic damage in ALT (Alanine transaminase), AST (aspartate transaminase), ALP (alkaline phosphatase) and GGT (gamma-glutamyltransferase) levels. Indicators of renal function (blood urea nitrogen (BUN), creatinine) and total protein and bilirubin were also within normal ranges in all groups. In addition, in histological observations of H & E staining (×200) of the heart, liver, lung, kidney and spleen in all groups, no bleeding was observed, and therefore, there was no difference between the groups (the rod shows 100 µm).

Example 3. Identification of Preservation of Biological Activity of Loaded Immunoreactive Substances

1. Experimental Method

In order to identify whether biological activity of an antibody or cytokine supported on the porous silica particles is also preserved as in the case of unsupported antibody or cytokine, cell proliferation in mouse T cells treated with IL-2-loaded porous silica particles (BALLkine-2) was confirmed by CCK assay. Further, STAT5 activity in IL-HEK cells treated with IL-2 loaded porous silica particles (BALLkine-2) was analyzed by means of HEK-Blue™ IL-2 assay (InvivoGen, CA, USA) according to the manufacturer's protocol.

2. Experimental Result

Referring to FIGS. 44 and 45, as compared to the case in which IL-2 is not supported, when IL-2 is supported on the porous silica particles, T cell proliferation and STAT5 activity of mice did not show significant difference regardless of treatment concentration. This result demonstrates that biological activity is well preserved even when the antibody or cytokine is treated while being supported on the porous silica particles of the present invention.

Example 4. Identification of Hypersensitivity by the Carrier of the Present Invention

1. Experimental Method

In vitro MUSST (myeloid U937 skin sensitivity test) assay was performed to assess potential immunogenicity of DEGRADABALL IL-2 and DEGRADABALL loaded with IL-2 (BALLkine-2), in particular, delayed hypersensitive response (type 4 hypersensitivity) thereof. A stimulation index of 3 or less means no response (NC: negative control, PC: positive control, stimulation index=average % of positive cells in test sample/average % of positive cells in NC, significant difference from NC group (##p<0.05)). The test was repeated three times in the NC and PC groups and twice in the other group.

2. Experimental Result

Referring to FIG. 46, all stimulation indices (from 10 times to 1/25 times the theoretical plasma concentration) of all groups were lower than 3.0, indicating no positive reaction. This result demonstrates that the carrier of the present invention did not have hypersensitive response, especially, delayed hypersensitive response.

Example 5. Identification of Stable Delivery and Targeting Property of the Carrier of the Present Invention

1. Delivery of Antibody

Figure 47:
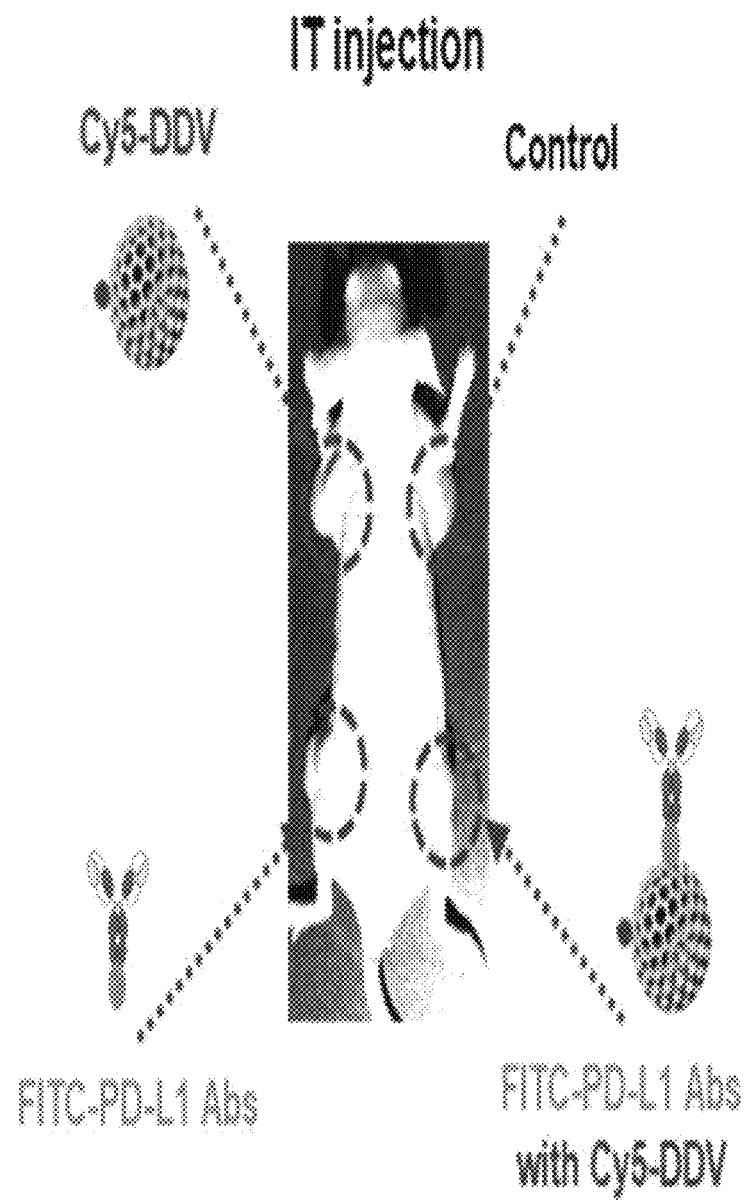
Figure 48:
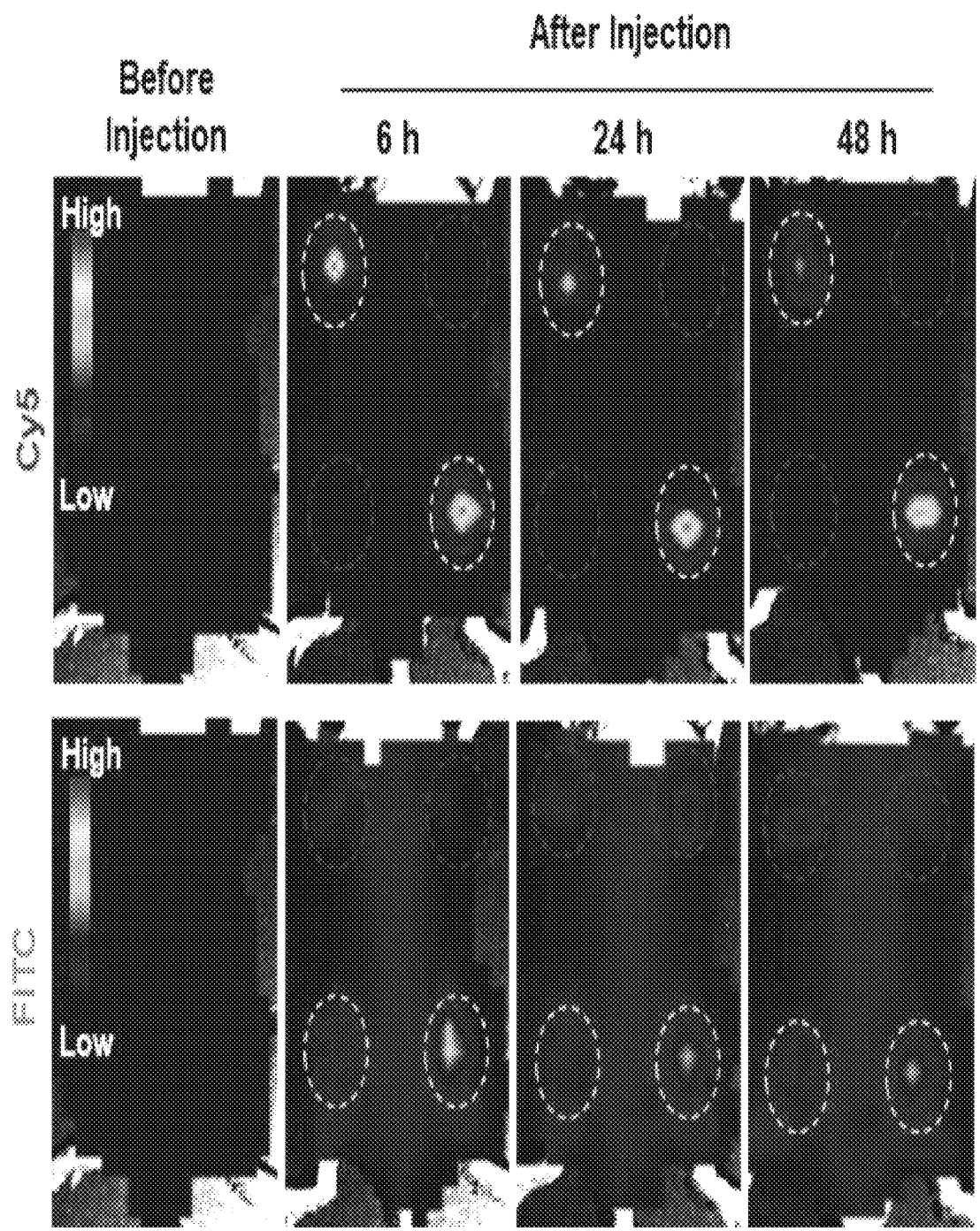

Referring to FIGS. 47 and 48, after labeling FITC and Cy5 on anti-PD-L1 antibody and DDV, respectively, DDV loaded with anti-PD-L1 antibody was intratumorally injected. Thereafter, fluorescence intensities of PD-L1 antibody and DDV were measured in each time interval. From the measured results, it could be seen that DDV and the anti-PD-L1 antibody remained at the administration site for a long time, and this indicates that the carrier of the present invention may stably deliver the loaded anti-PD-L1 antibody and allow the antibody to stay in the tumor and at the administration site for a long time, thereby exhibiting long-term efficacy.

2. Delivery of Cytokine

Figure 49:
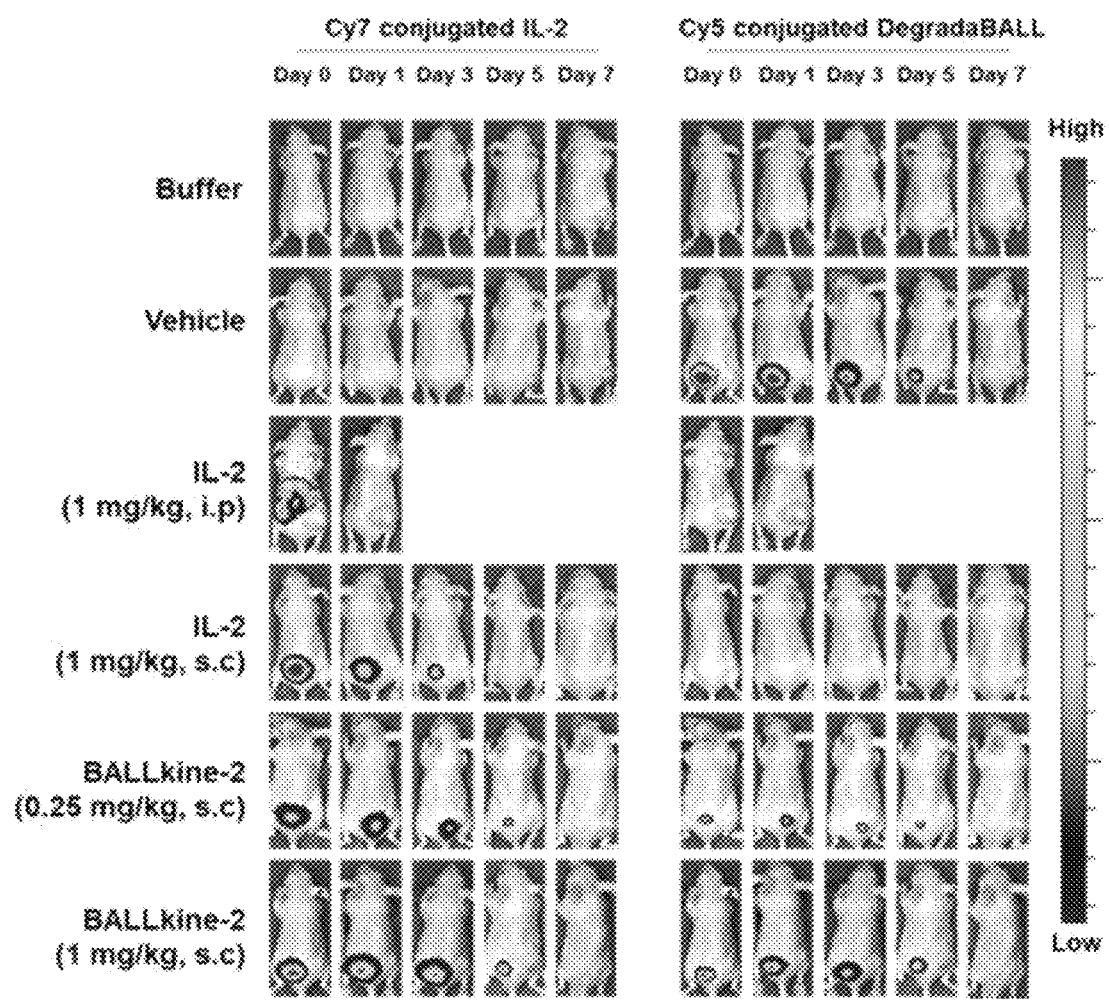

Referring to FIG. 49, after labeling Cy7 and Cy5 to IL-2 and DDV, respectively, DDV loaded with IL-2 (BALLkine-2) was administered through subcutaneous injection (SC injection). Thereafter, fluorescence intensities of IL-2 and DDV were measured in each time interval. From the measured results, it could be seen that DDV and BALLkine-2 remained at the administration site for a long time, and this indicates that the carrier of the present invention may stably deliver the loaded IL-2.

Figure 50:
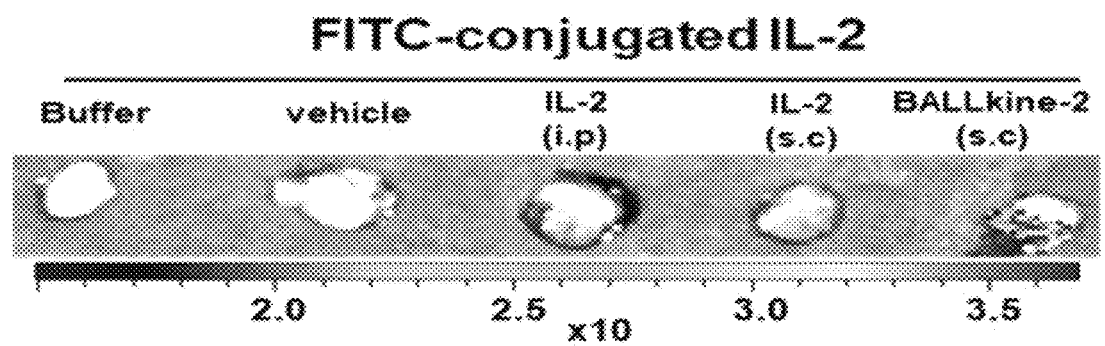
Figure 51:
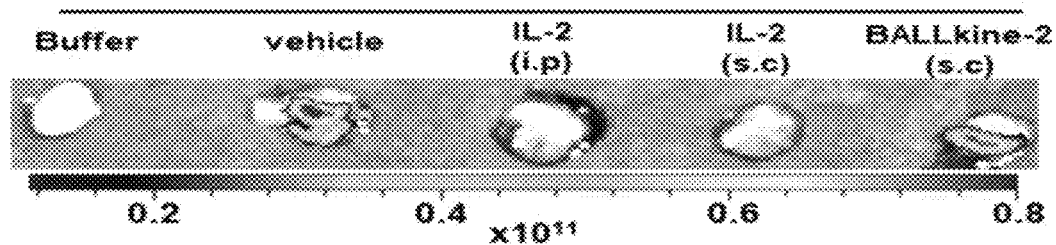

Referring to FIGS. 50 and 51, FITC fluorescence was applied to IL-2 while TAMRA fluorescence was applied to DDV, followed by subcutaneous administration. After 24 hours, lectin labeled with Cy5 fluorescence was injected into the tail vein to stain the blood vessels and then the tumor was extracted to confirm fluorescent image. From the results, it could be seen that DDV and BALLkine-2 were specifically distributed in the tumor tissue, and this indicates that the carrier of the present invention may deliver the loaded IL-2 to a target in a tumor-specifically targeting manner.

Figure 52:
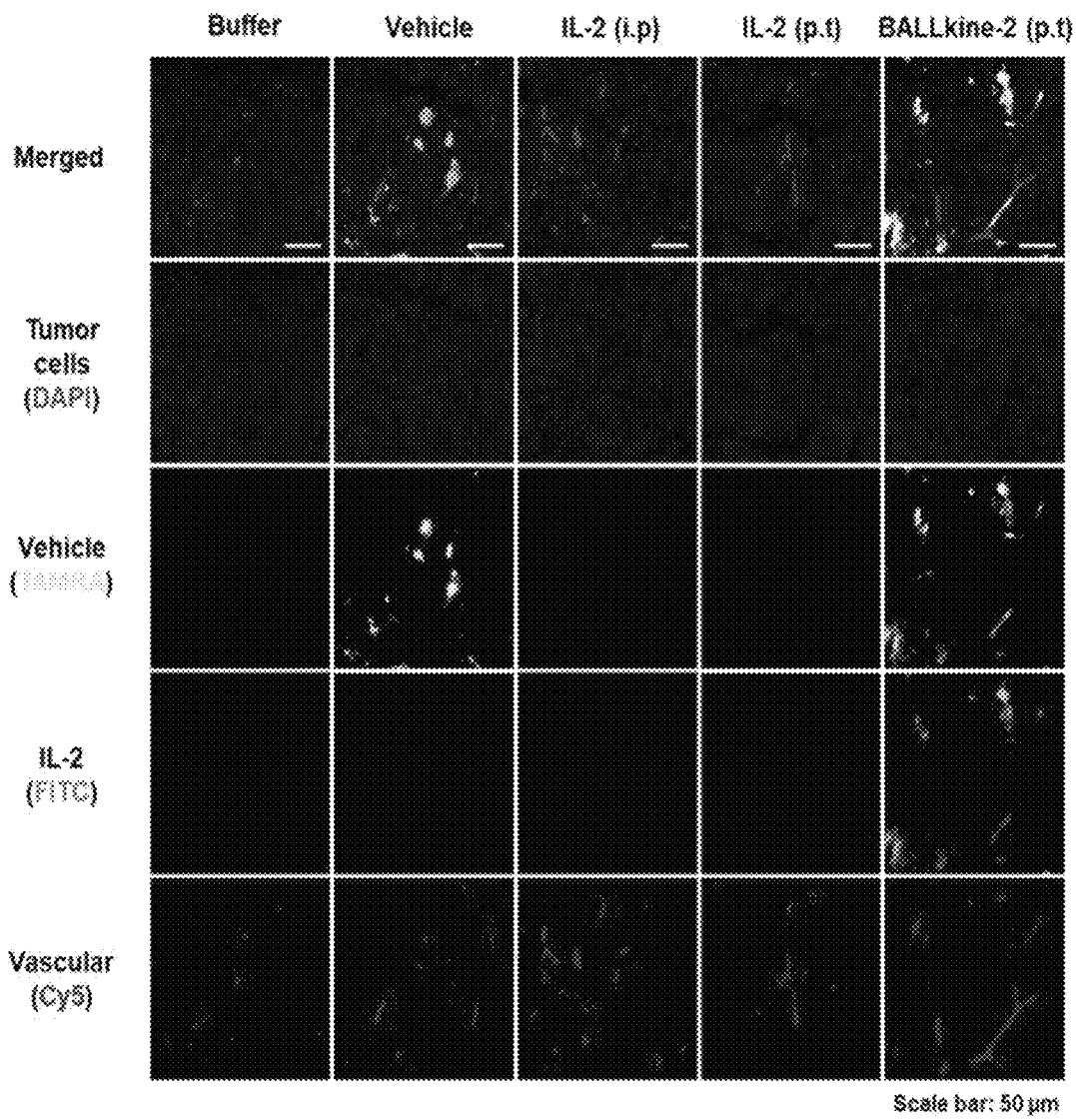
Figure 53:
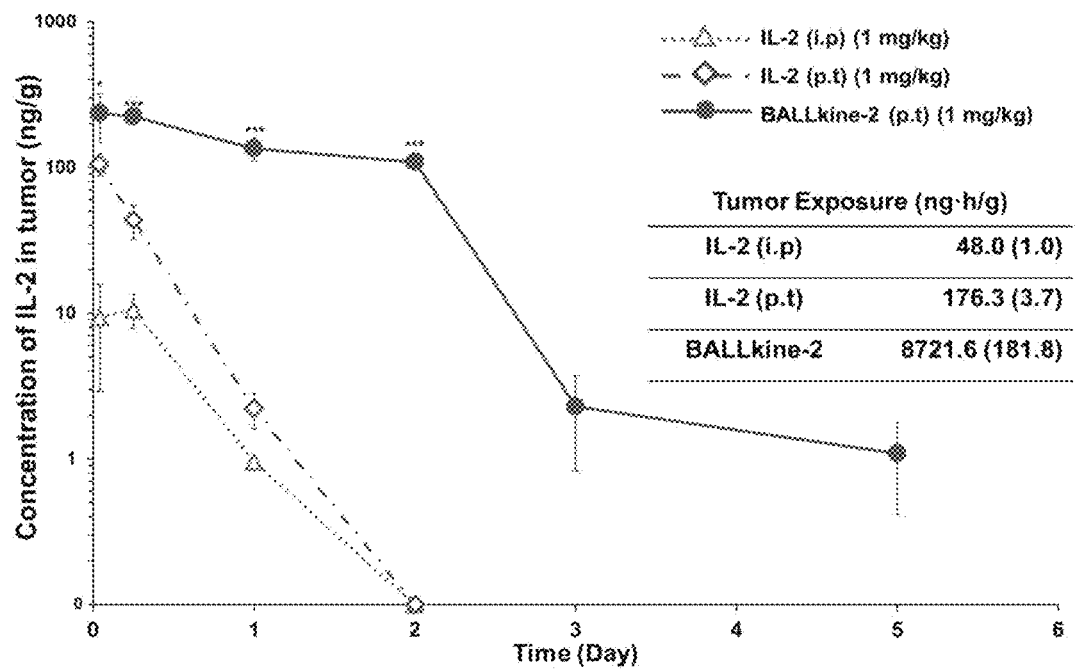

FIG. 52 shows histological cross-sectional images of tumor tissues to demonstrate tumor cells (DAPI), vehicle (TAMRA), IL-2 (FITC) and dylight 649-conjugated lectin, and FIG. 53 illustrates intratumoral pharmacokinetics of BALLkine-2 (p.t.) and IL-2 (i.p. or p.t.) (graphs represent mean±standard deviation of 3 mice per measurement time), wherein an amount of IL-2 in the tumor after subcutaneous injection was measured by ELISA and the measured results were shown in the drawings. Referring to FIGS. 52 and 53, it can be seen that the porous silica particles of the present invention may maintain IL-2 in the tumor and at the administration site for a long time, and stably deliver IL-2 thereto.

Figure 54:
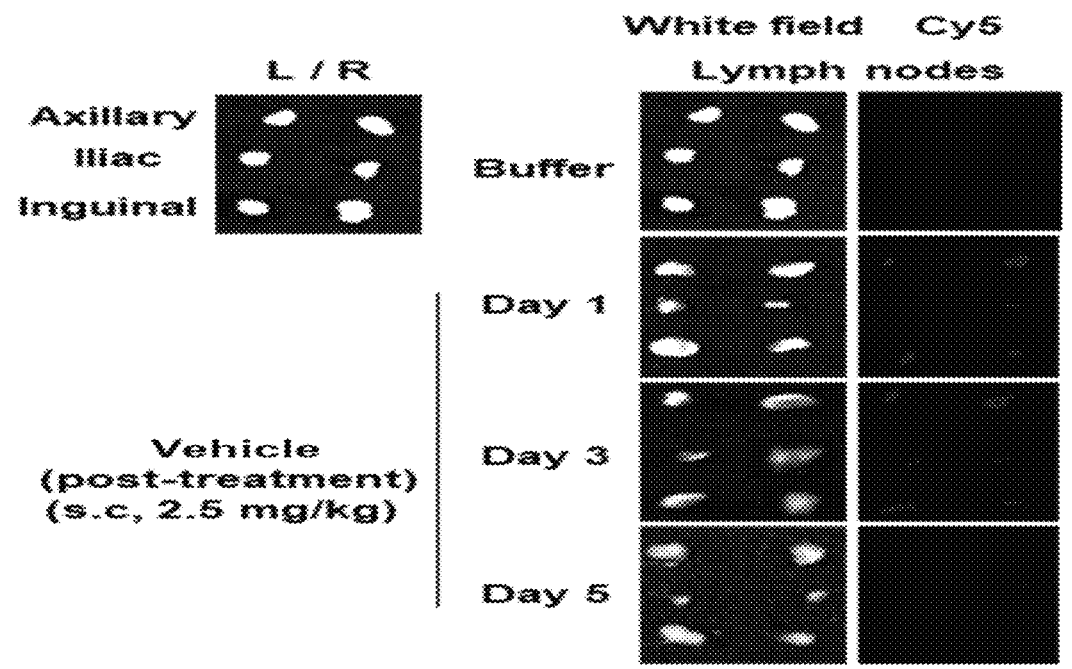
Figure 55:
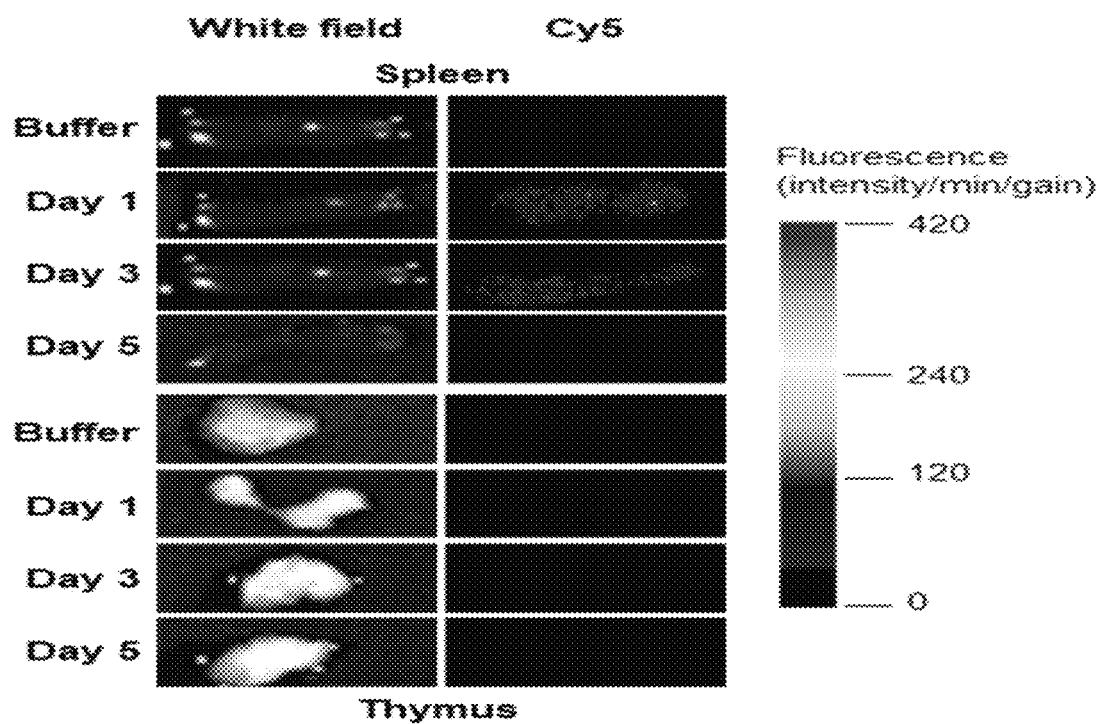

3. Identification of Delivery Ability of Immune Reactant Substance to Immune Organ FIGS. 54 and 55 illustrate fluorescent images of the organs, which were taken by a FOBI imaging system, wherein 1×PBS buffer (100 L) and Cy5-conjugated DEGRADABALL (2.5 mg/kg) were subcutaneously injected to the mice, followed by sacrificing the same at 1, 3 and 5 days after the administration and isolating the organs (skin, thymus, spleen and lymph nodes). From the fluorescent images, it can be seen that the immunoreactive substance is distributed to the immune organs on 1, 3 and 5 days, and this indicates that the porous silica particles of the present invention can stably deliver a variety of immunoreactive substances loaded thereon to the immune system.

Example 6. Identification of Cancer Immunotherapeutic Efficacy of the Carrier of the Present Invention

1. Melanoma Model

Figure 56:
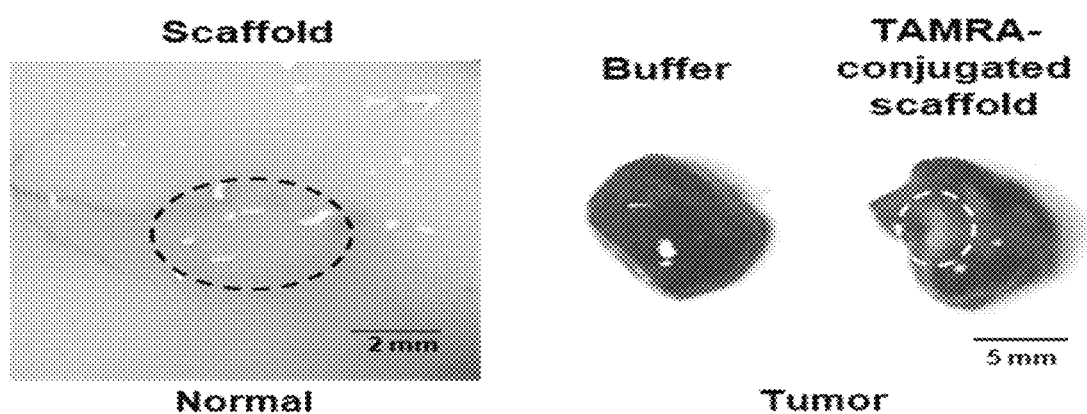
Figure 57:
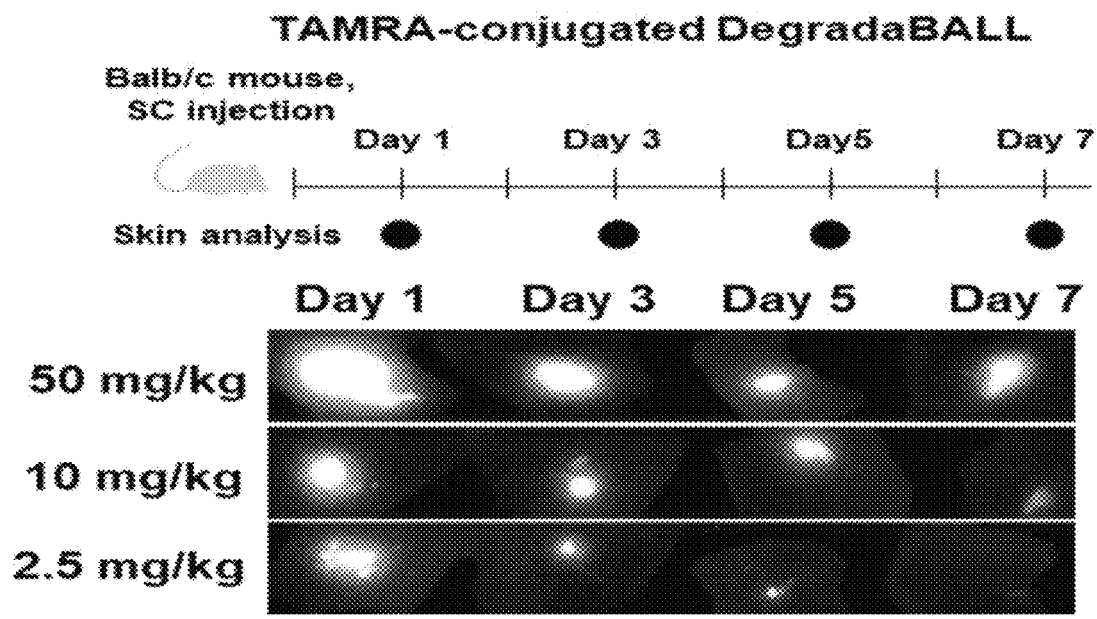

Referring to FIG. 56, DEGRADABALL was injected subcutaneously or around tumors (that is, peritumorally) of the normal mice and the melanoma tumor bearing mice, respectively. Referring to FIG. 57, all mice were injected subcutaneously with DEGRADABALL having TAMRA at doses of 2.5, 10, and 50 mg/kg, respectively, and skin tissues were extracted at 1, 3, 5, and 7 days later to provide fluorescent images. From the fluorescent images, it can be seen that the fluorescence remains even on the 7th day after the injection, and this implies that the porous silica particles of the present invention may have high in vivo stability and carry the sustained release of the immunoreactive substance stably for a long time.

Figure 58:
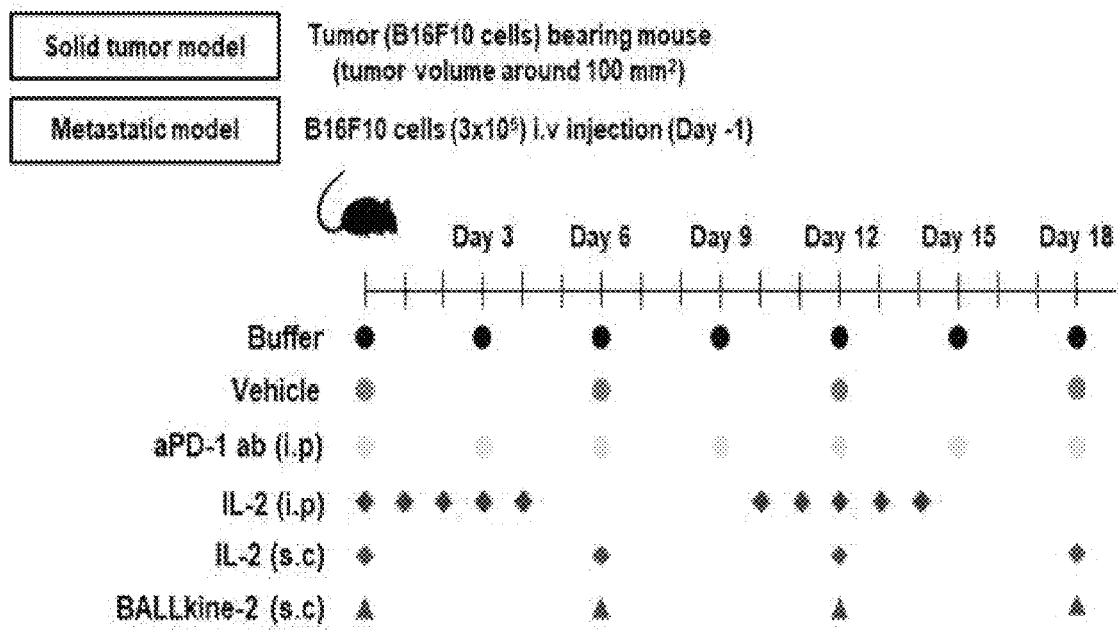
Figure 59:
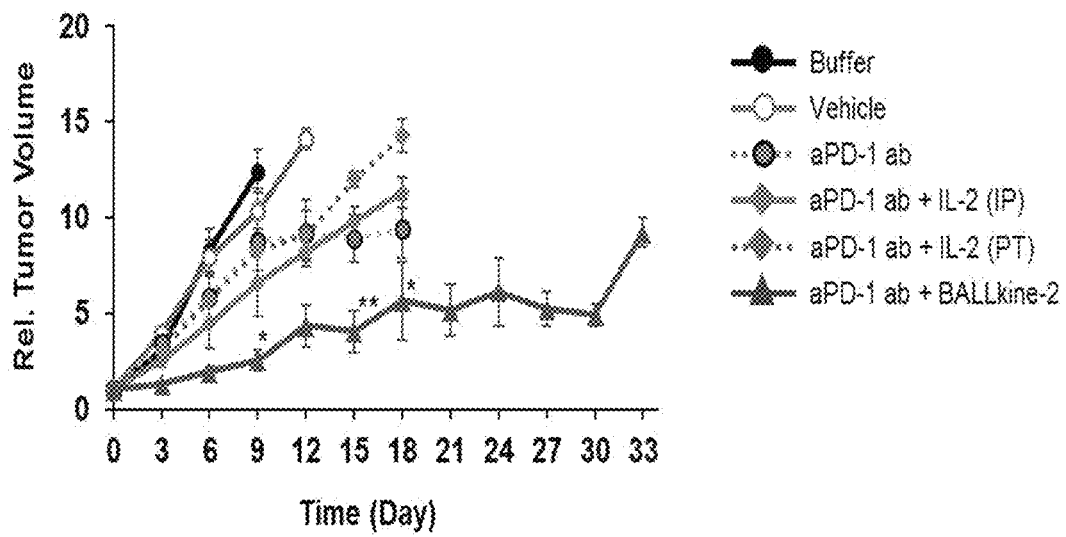
Figure 60:
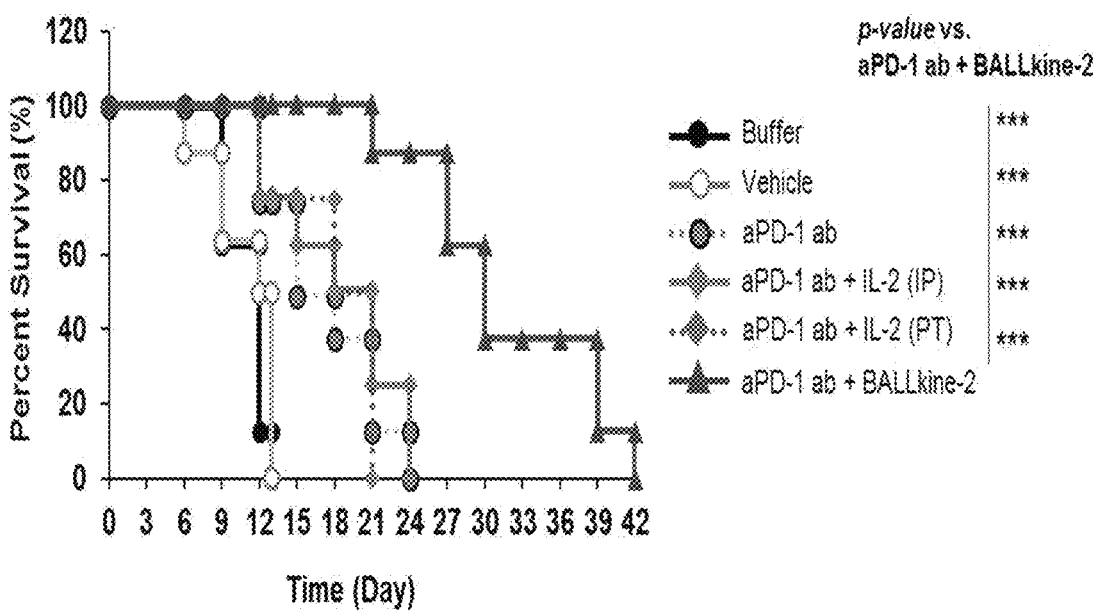

In order to demonstrate superior melanoma treatment effects of the carrier according to the present invention, an experiment was performed in a melanoma mouse model according to the protocol of FIG. 58 and Table 2 below. A growth rate of tumor was measured for each group, and results of measuring the growth rate of tumor for each mouse individual are shown in FIG. 59. Co-administration of aPD-1 antibody and IL-2 had a lower growth rate than the aPD-1 antibody exclusive administration group. From this drawing, it can be seen that the growth rate is remarkably reduced when IL-2 was supported on the porous silica particles and co-administered (BALLkine-2). Further, it can be seen in FIG. 60 that a survival rate (i.e., viability) of each group in the co-administration of IL-2 supported on the porous silica particles (BALLkine-2) is significantly higher than that in the other groups.

co-administered with the aPD-1 antibody (BALLkine-2), the viability was remarkably higher than the other cases (10 mice per group). Further, in order to investigate an immune reaction mechanism in treatment of melanoma using the carrier of the present invention, tumor infiltrating lymphocytes (TILs) assay was performed according to the protocol of FIG. 64. Specifically, TIL assay was performed by: separating immune cell populations ((b) $CD8^+$ T cells, (c) $CD4^+$ T cells, (d) active NK cells, (e) Treg cells, (f) $CD8^+$/Treg cells) from the mice on target days (1, 3, 5 and 7 days after the administration of BALLkine-2); analyzing the cells through flow cytometry (dots represent individual tumor tissues, lines represent an average of tumor tissues of 8 mice); and staining and analyzing immune tissues of $CD8^+$ T cells on 3 and 5 days. Referring to a representative image of the BALLkine-2 administration group (FIG. 70), it can be seen that the number of $CD8^+$ T cells is dramatically increased and the cells are dispersed or distributed between a wide range of tumor cells. Further, BALLkine-2 was injected into the right flank of a mouse having B16F10 melanoma tumors (peritumoral injection), and then, the spleen and drainage lymph nodes (iliac and inguinal lymph nodes) were separated on 1, 3 and 5 days. Then, lymphocytes ($CD8^+$ T cells and NK cells) were isolated to evaluate

TABLE 2

| Dose group | Dosing protocol | Total dose |
|---|---|---|
| Buffer (i.p) | 7 intraperitoneal (ip) injections every 3 days (0, 3, 6, 9, 12, 15, 18 day) | |
| DEGRADABALL (s.c) | 4 peritumoral injections every 6 days (0, 6, 1 2, 18 day) | |
| aPD-1 antibody (i.p) | 7 ip injections every 3 days (0, 3, 6, 9, 12, 15, 18 day) | 70 mg/kg |
| aPD-1 antibody (i.p) + IL-2(i.p) | aPD-1 antibody: 7 ip injections every 3 days (0, 3, 6, 9, 12, 15, 18 day) IL-2: 2 cycles ip injections every 5 days (0, 1, 2, 3, 4, 10, 11, 12, 13, 14 day) | aPD-1 antibody: 70 mg/kg IL-2: 10 mg/kg |
| aPD-1 antibody (i.p) + IL-2(s.c) | aPD-1 antibody: 7 ip injections every 3 days (0, 3, 6, 9, 12, 15, 18 day) IL-2: 4 peritumoral injections every 6 days (0, 6, 12, 18 day) | aPD-1 antibody: 70 mg/kg IL-2: 4 mg/kg |
| aPD-1 antibody (i.p) + BALLkine-2(s.c)(1 or 0.25 mg/kg) | aPD-1 antibody: 7 ip injection every 3 days (0, 3, 6, 9, 12, 15, 18 day) BALLkine-2: 4 peritumoral injections every 6 days (0, 6, 12, 18 day) | aPD-1 antibody: 70 mg/kg BALLkine-2: 4 mg/kg or 1 mg/kg |

Figure 61:
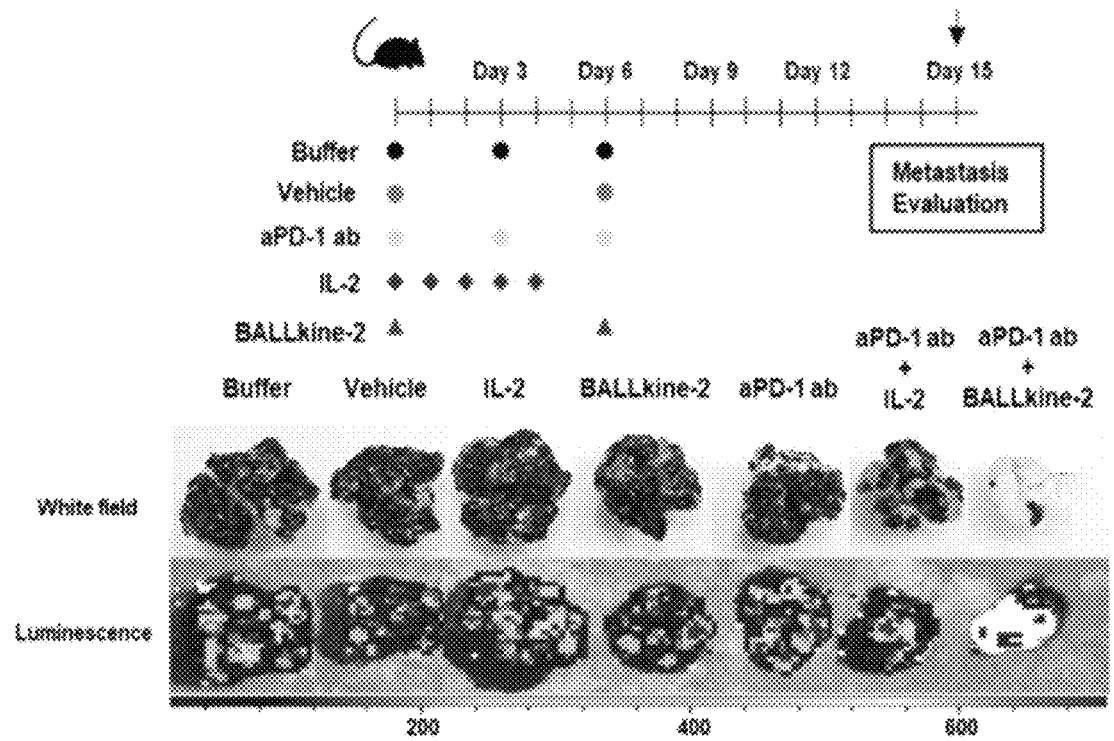
Figure 62:
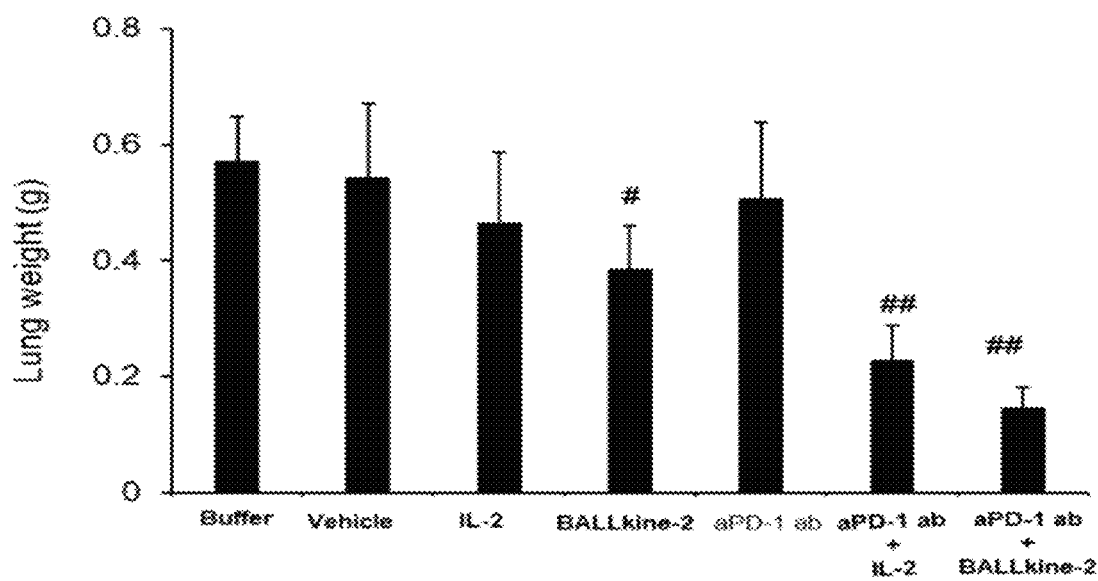
Figure 63:
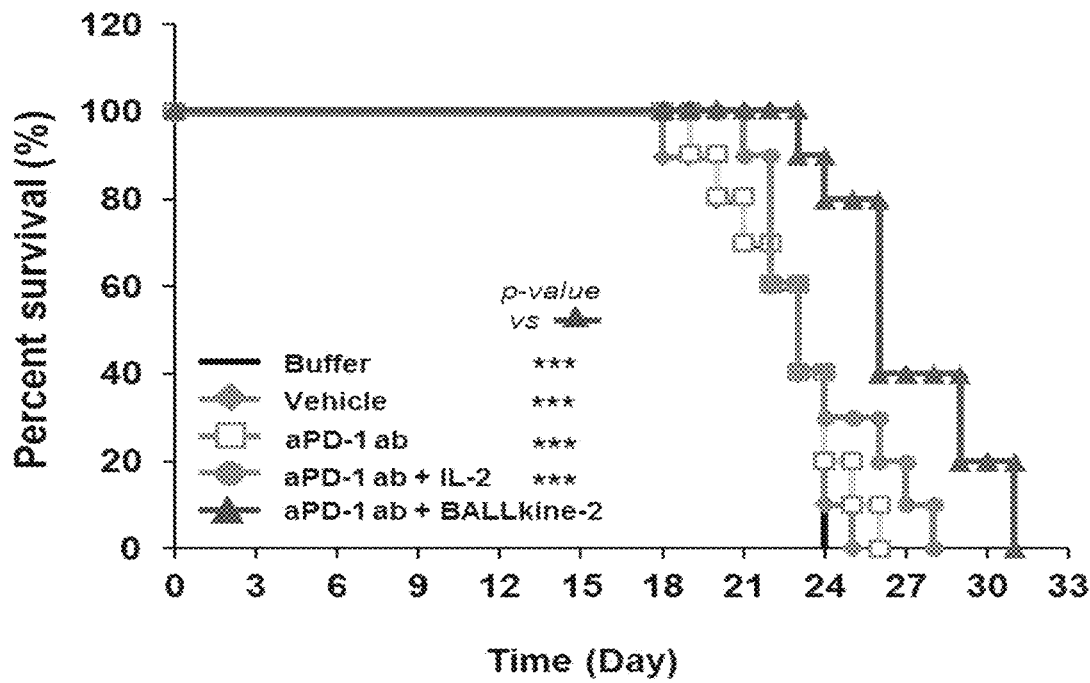
Figure 64:
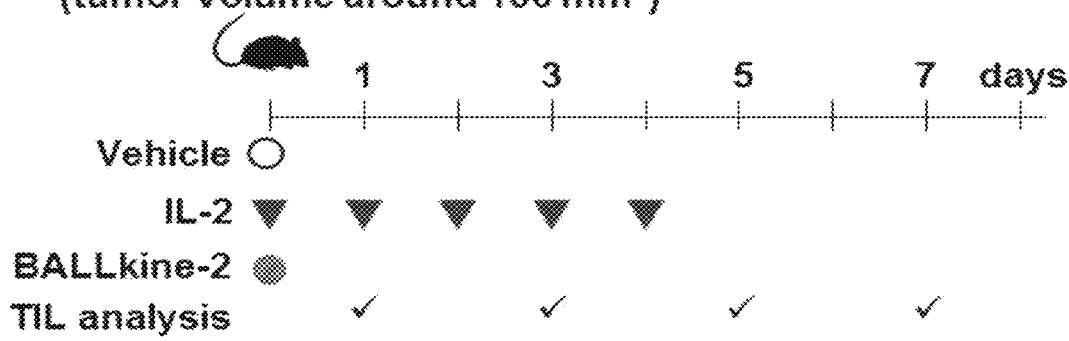
Figure 65:
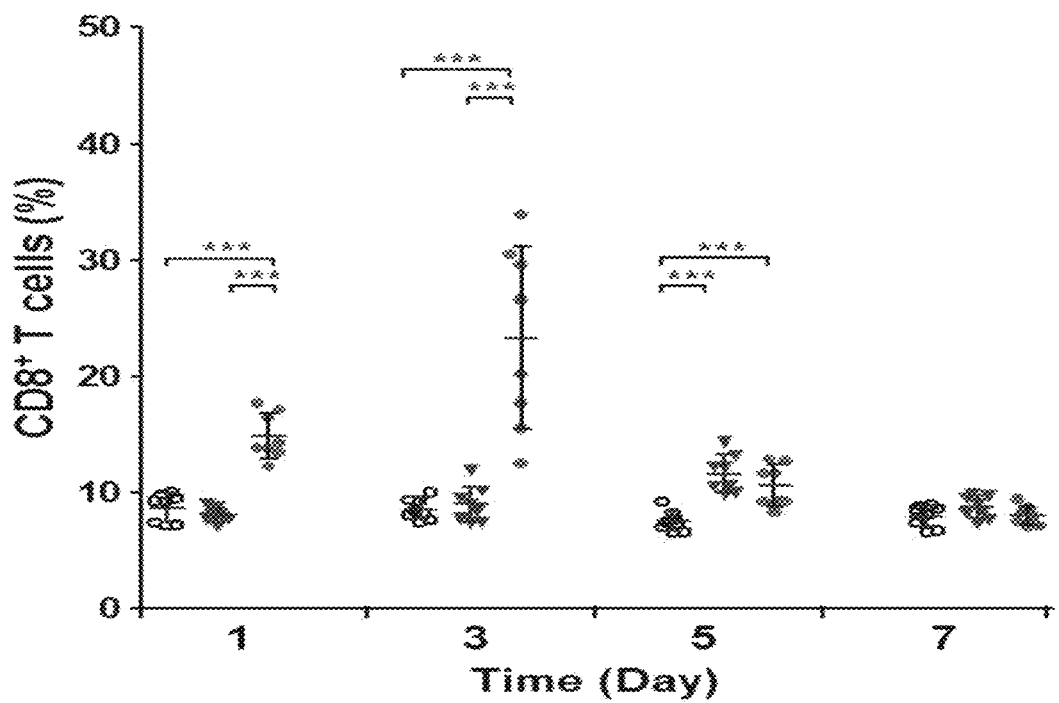
Figure 66:
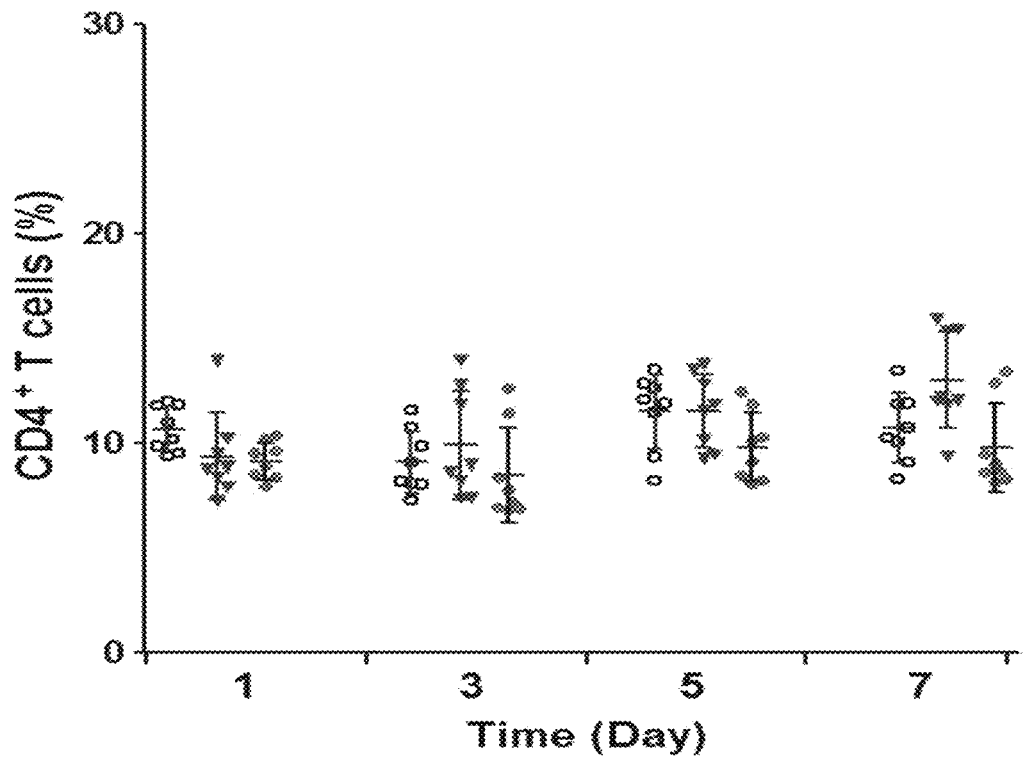
Figure 67:
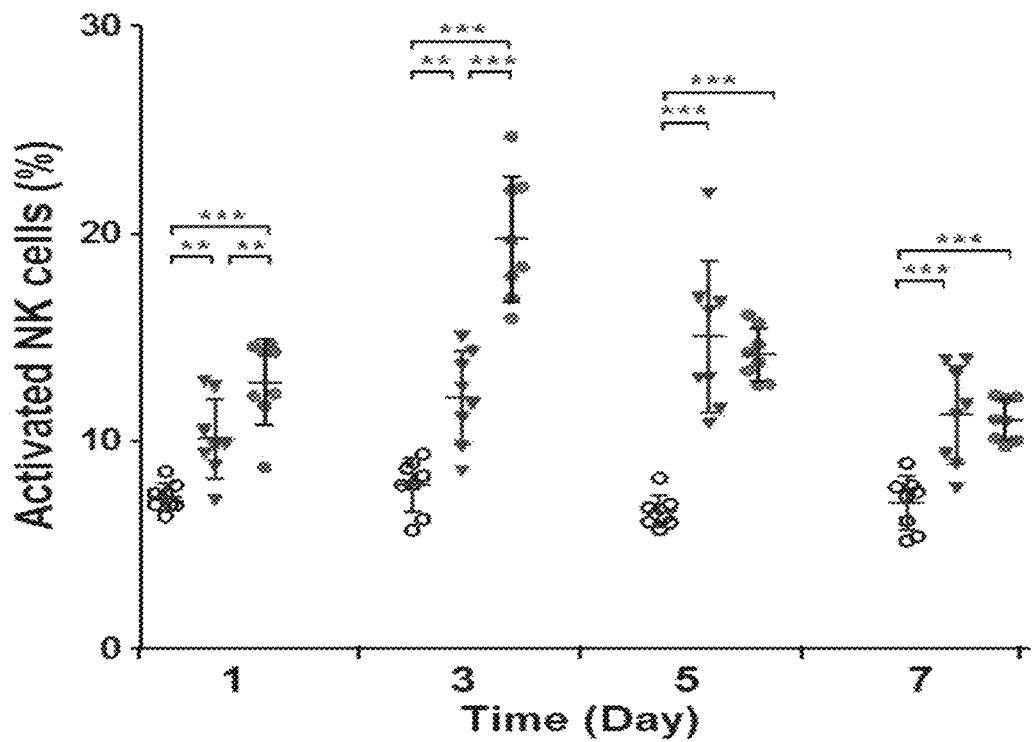
Figure 68:
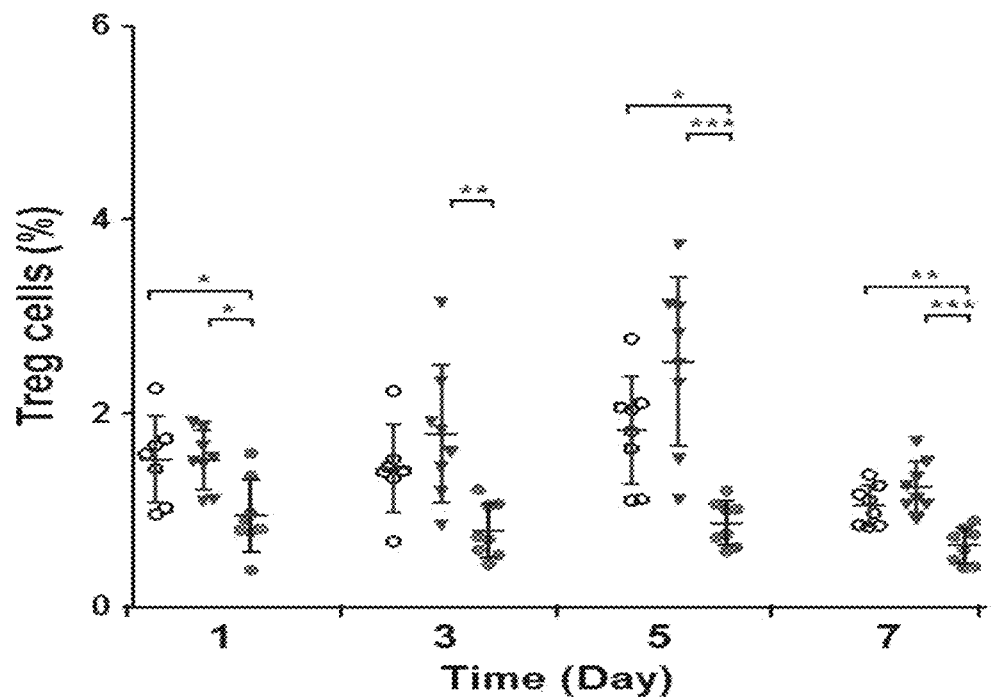
Figure 69:
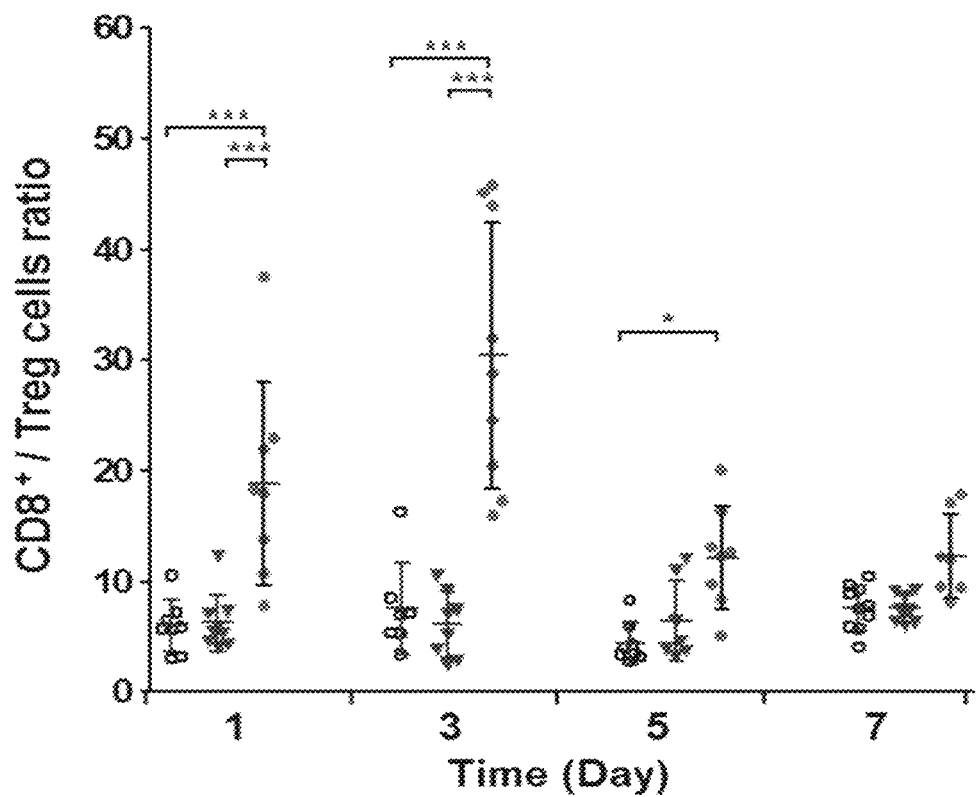
Figure 70:
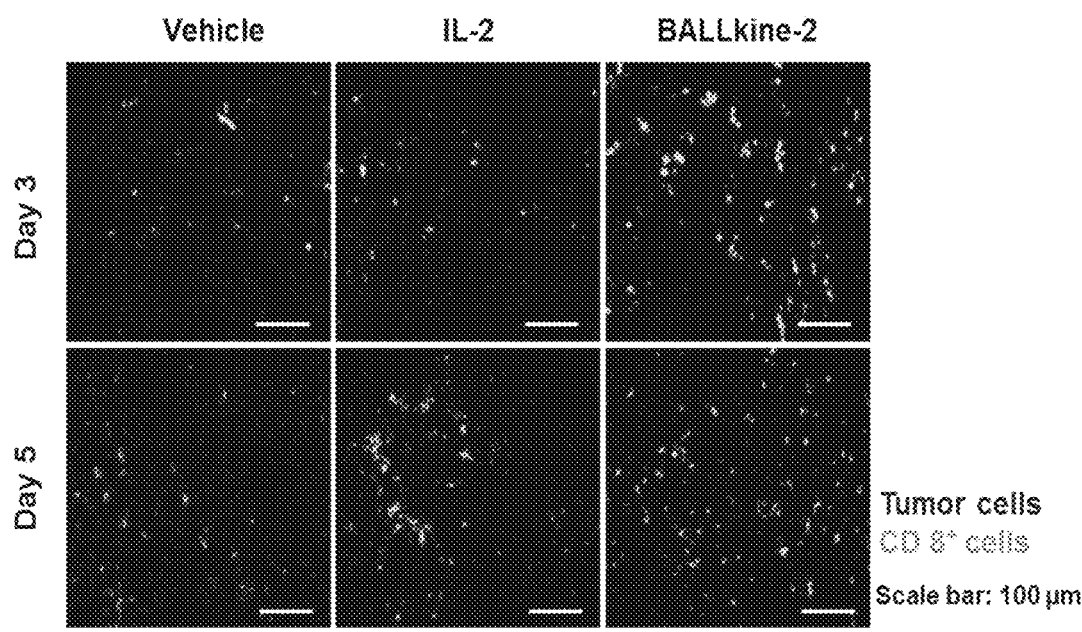
Figure 71:
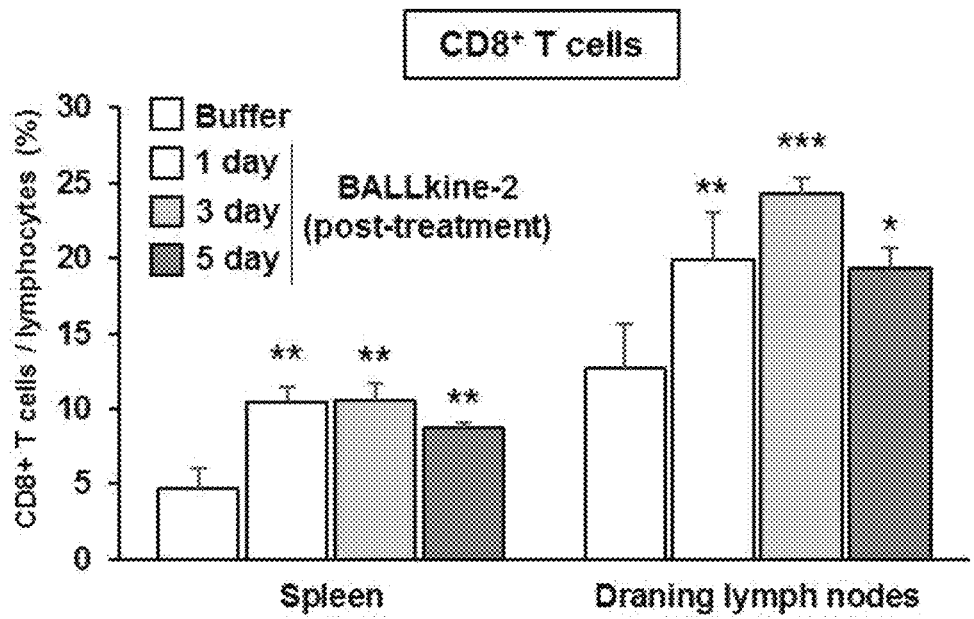
Figure 72:
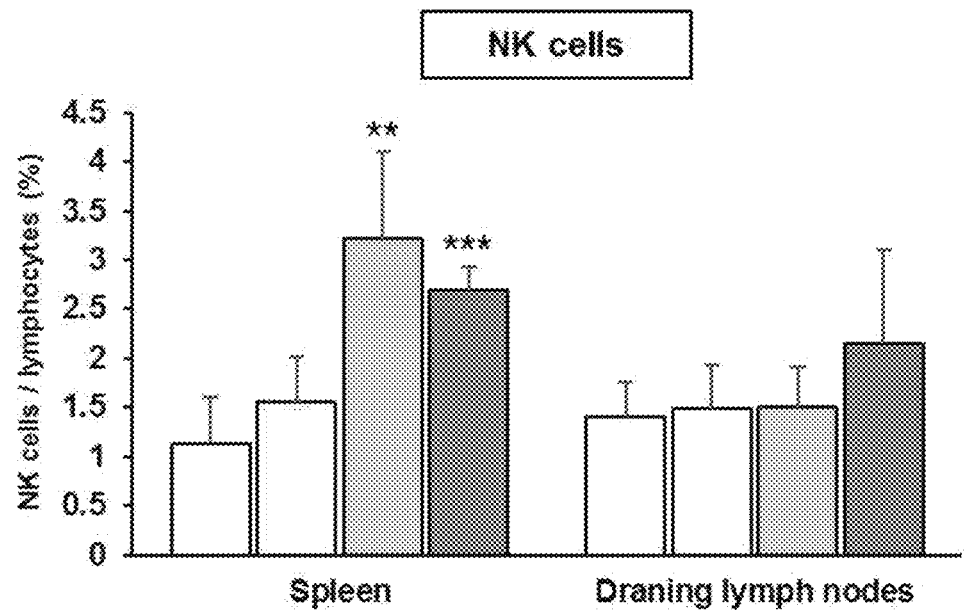
Figure 73:
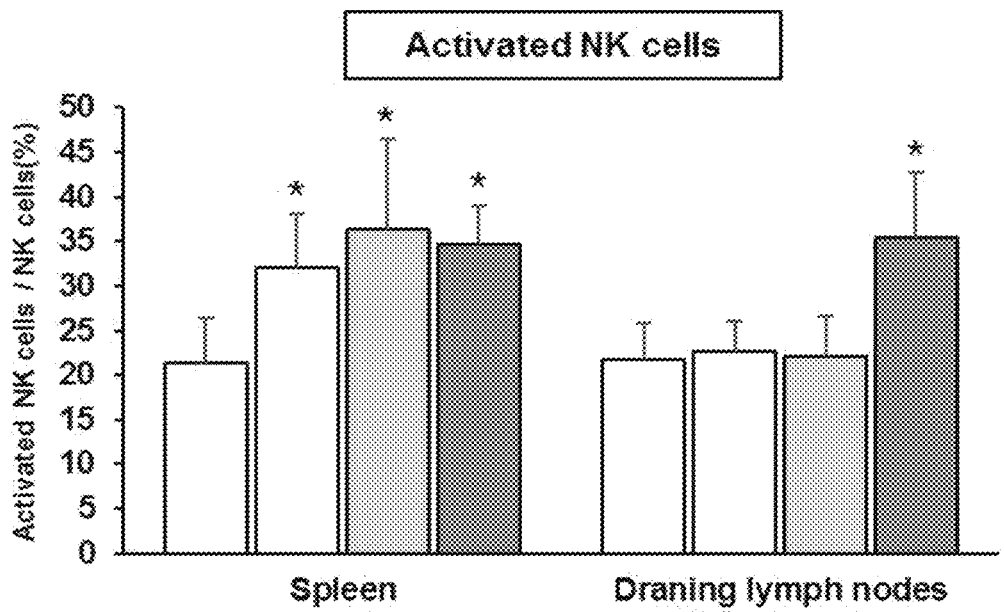
Figure 74:
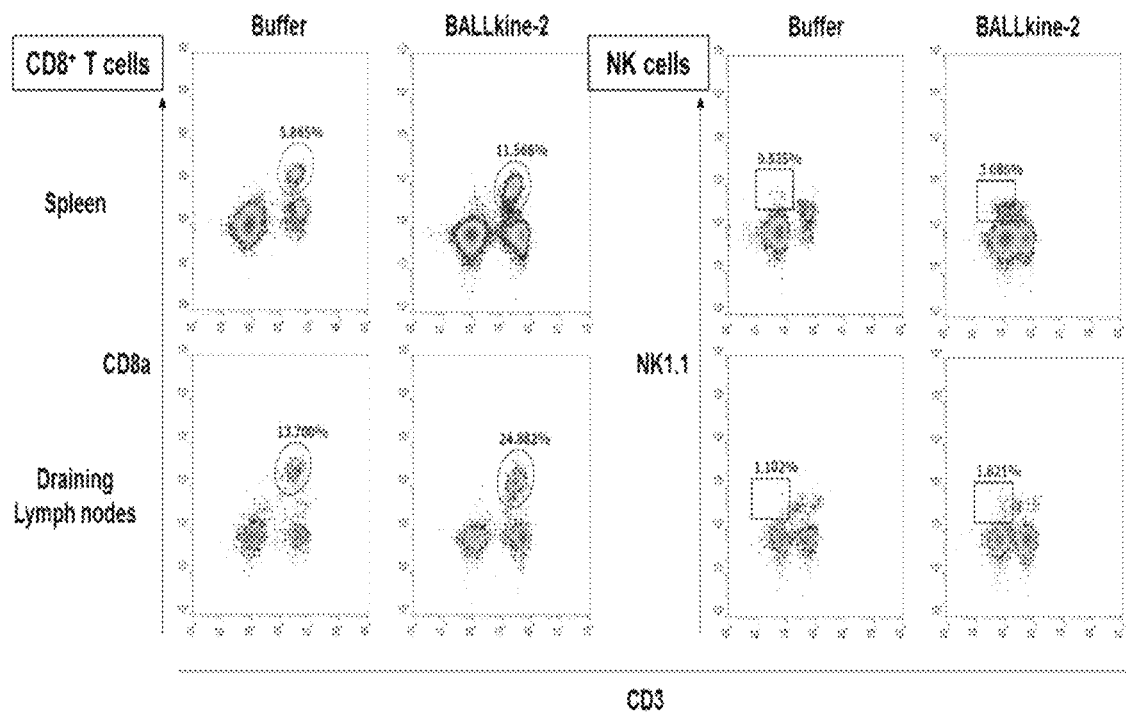

Further, in order to demonstrate superior therapeutic effects of metastatic melanoma by the carrier of the present invention, an experiment was performed in a lung metastasis mouse model of metastatic melanoma according to the protocol of FIG. 61. Similar to the results shown in FIGS. 58 to 60, co-administration of aPD-1 antibody and IL-2 had a lower growth rate than the aPD-1 antibody exclusive administration group. That is, when IL-2 was supported on the porous silica particles (BALLkine-2) and then co-administered, it could be confirmed that the growth rate was remarkably low. Specifically, as shown in FIG. 61, when IL-2 was supported on the porous silica particles and co-administered with aPD-1 antibody (BALLkine-2), it could be seen that a black cancer tissue portion was dispersed around a considerably small area thus to reduce lung metastasis while remarkably suppressing an increase in lung volume and formation of lung tumor nodules. Further, FIG. 62 demonstrates that, when IL-2 supported on the porous silica particles was co-administered with the aPD-1 antibody (BALLkine-2), the weight of each lung with progressed lung metastasis was also significantly lower than the other cases (data are expressed as mean standard deviation of 3 mice). Further, in a case of viability, FIG. 63 demonstrates that, when IL-2 supported on the porous silica particles was immune cell populations (data are expressed as mean±standard deviation of 3 mice). As a result, it can be seen that the number of immune cells in the BALLkine-2 administration group is remarkably increased as compared to the control.

2. Renal Cell Carcinoma Model

Figure 75:
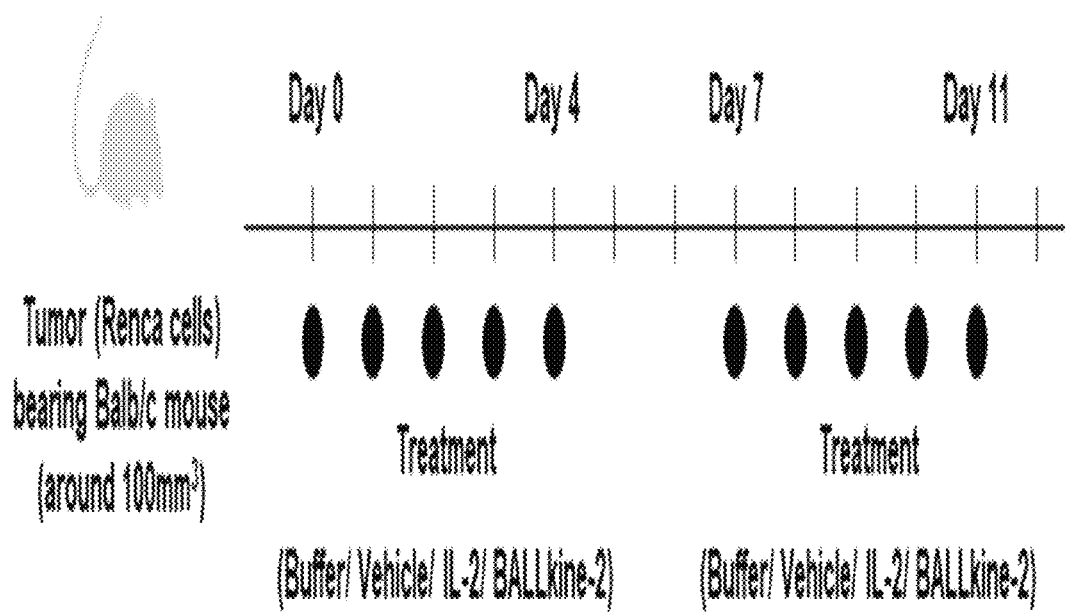
Figure 76:
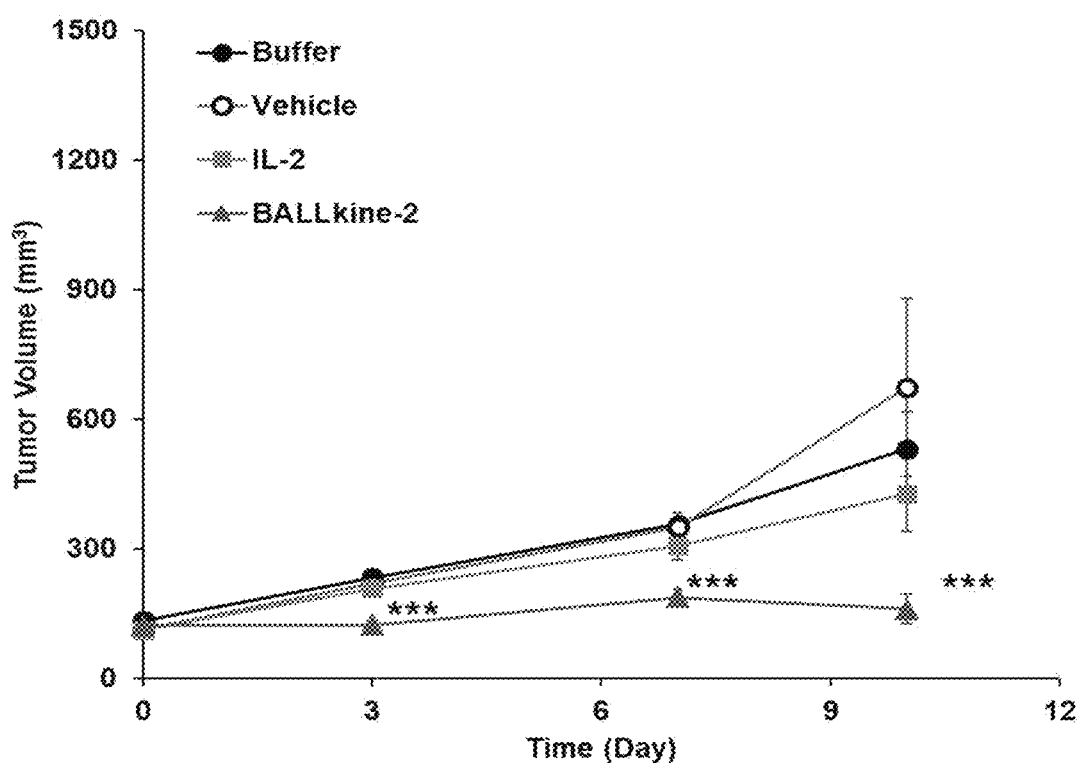

In order to identify excellence of renal cancer treatment using the carrier of the present invention, the extent of tumor growth inhibition by IL-2 supported on the porous silica particles (BALLkine-2) in the renal cell carcinoma (RCC) xenograft mouse model was determined according to the protocol of FIG. 75, as compared to the case in which IL-2 is not supported on the porous silica particles. As can be seen in FIG. 76, BALLkine-2 showed significant tumor growth inhibition superiority over IL-2, thereby proving the excellence in renal cancer treatment (data are mean±SEM, 7 mice per group, ***$p<0.001$: significantly different from other groups).

Figure 77:
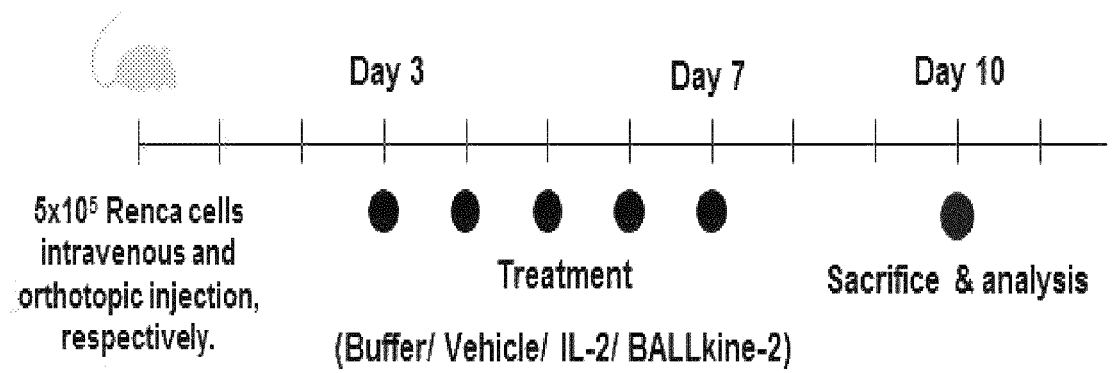
Figure 78:
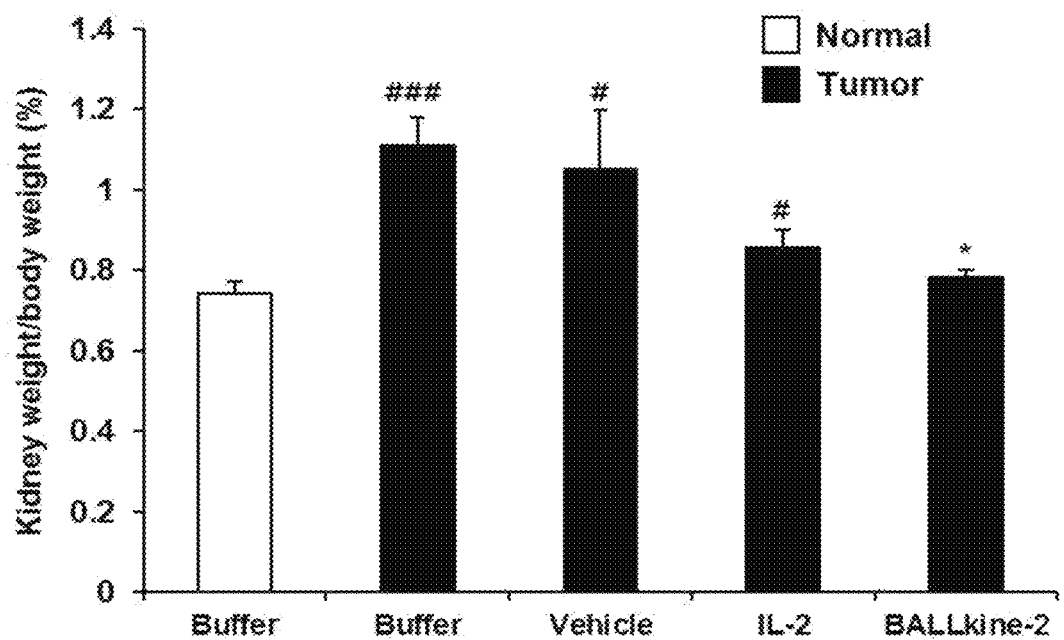
Figure 79:
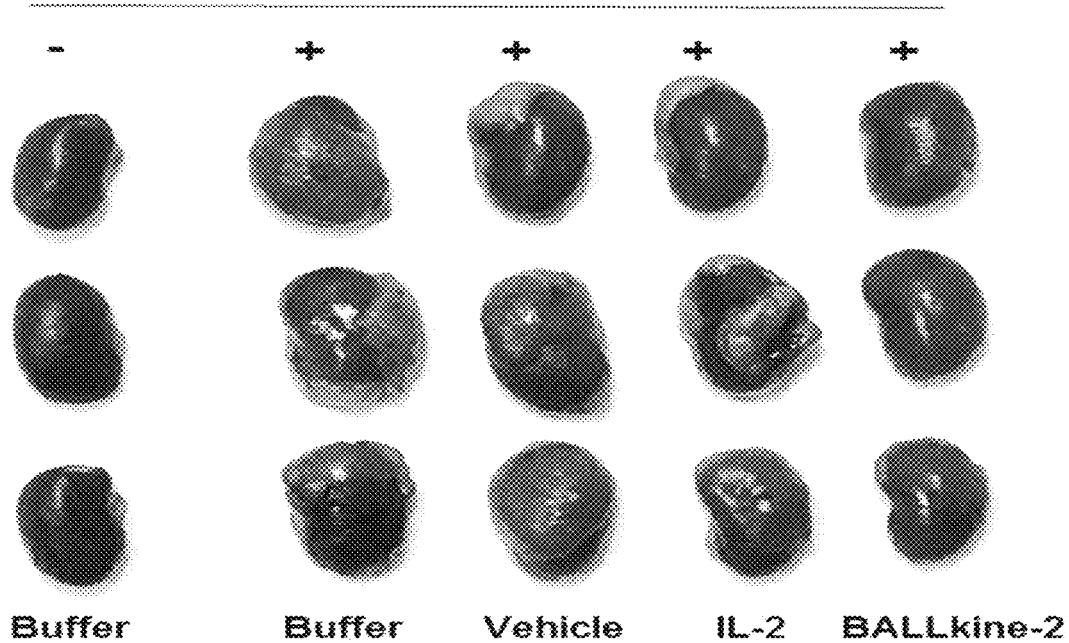
Figure 80:
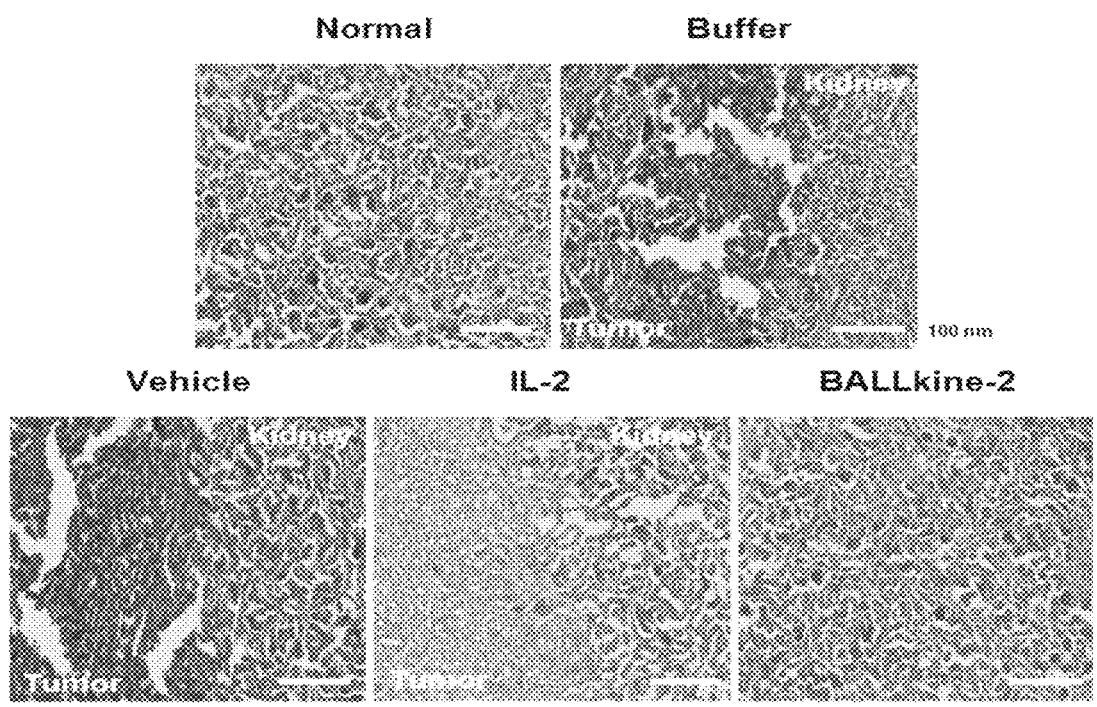
Figure 81:
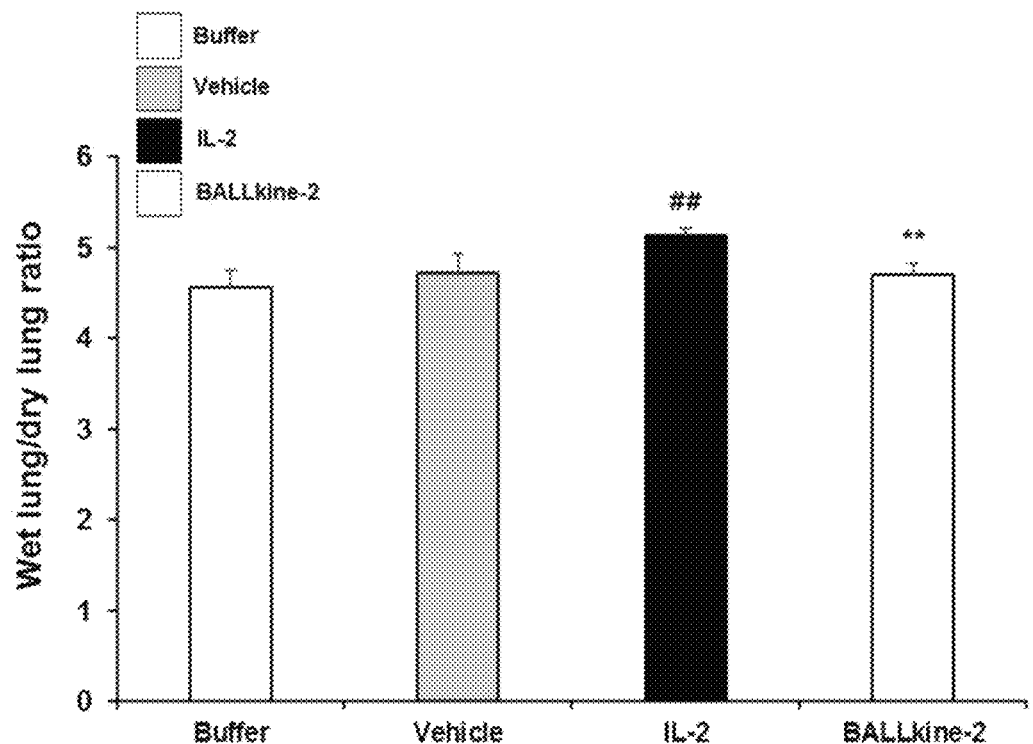

Further, in order to identify the extent of tumor growth inhibition of IL-2 supported on the porous silica particles (BALLkine-2) in the metastatic and orthotopic mouse models of RCC, as compared to the case in which IL-2 is not supported on the porous silica particles, an experiment was performed according to the protocol of FIG. 77. Mice were sacrificed on 10 days after the administration, kidneys were removed and weighed (calculated weight/body weight in %; data are mean±SD, 3 mice per group, #p<0.05, ###p<0.001: significantly different from the control (buffer administration group), *p<0.05: significantly different from the IL-2 administration group). From FIG. 78, it can be seen that the kidney weight of the BALLkine-2 administration group is significantly lower than the IL-2 administration group. Further, from the measured image of the extracted kidney of FIG. 79, it can be seen that the kidney size of BALLkine-2 is significantly smaller than that of other groups. Further, from H & E staining photographs of the kidney tissue in FIG. 80, it can be seen that the tissue staining extent is significantly higher in the BALLkine-treatment group than the other groups. In addition, in order to assess pulmonary edema, wet lungs were harvested and weighed, and then dried in an oven at 60° C. for 3 days and weighed again (FIG. 81, data are mean±SD, 3 mice per group, ##p<0.01: significantly different from the control (buffer administration group), **p<0.01: significantly different from the IL-2 administration group). From the measured results, it could be seen that the weight ratio of wet and dry lungs in the BLLkine-2 treatment group was significantly lower than the IL-2 administration group.

Figure 82:
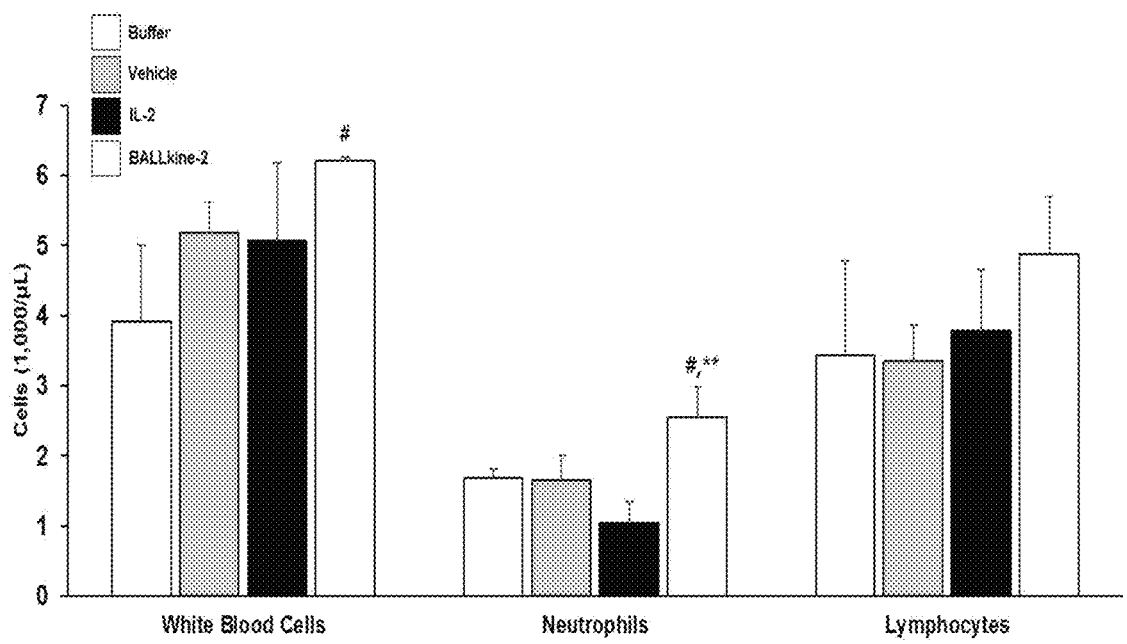

In addition, from the analyzed results of leukocytes, neutrophils and lymphocytes in the blood of mice (FIG. 82, data are mean±SD, 3 mice per group, #p<0.05: significantly different from the control (buffer administration group), *p<0.05: significantly different from the IL-2 administration group), it could be seen that the number of the above cells was significantly higher in the BALLkine-2 treatment group than the other groups, thereby achieving remarkable excellence in immune response promoting effects.

3. Other Cancer Models

Effects of the composition according to the present invention on other carcinomas, including melanoma and kidney cancer, are shown in Table 3 below.

TABLE 3

| Cancer type | Cell line | Measurement variables | Control (vehicle) | Test group 1 | Test group 2 | Test group 3 |
|---|---|---|---|---|---|---|
| Melanoma | B16F10 | Relative tumor size (12 day) | 14.1 | IL-2/aPD-1 antibody<br>9.1 | IL-2 + DEGRADABALL/ aPD-1 antibody<br>4.3 | |
| | | Relative tumor size (10 day) | 12.5 | IL-15<br>8.2 | IL-15 + DEGRADABALL<br>3.9 | |
| Kidney cancer | Renca | Kidney weight to body weight (w/w %; 10 day) | 1.05 | IL-2<br>0.86 | IL-2 + DEGRADABALL<br>0.78 | |
| Liver cancer | BNL-h1 | Number of liver metastases | 85 | IL-12<br>9 | IL-12 + DEGRADA BALL<br>2 | |
| Colorectal cancer | CT26(s.c) | Tumor size (mm³; 19 day) | 452 | aPD-L1 antibody<br>220 | aPD-L1 antibody + DEGRADABALL<br>187 | |
| | CT26(i.v) | bioluminescence, photon/s | 38 | IL-2<br>11 | IL-2 + DEGRADABALL<br>1.4 | |
| Lung cancer | LLC | Bioluminescence, photon/s | 3.9 | IL-12<br>1.1<br>PTX/CDDP<br>3.8 | IL-12 + DEGRADA BALL<br>0.4<br>IL-2/ PTX/CDDP<br>0.2 | IL-12 + DEGRADABALL/ PTX/CDDP<br>0.01 |
| Breast cancer | 4T1 | Tumor size (mm³; 20 day) | 411 | IL-12<br>32.4 | IL-12 + DEGRADA BALL<br>8.3 | |
| | EMT-6 | Tumor size (mm³; 28 day) | 953 | IL-21<br>521<br>aCTLA-4 antibody<br>320 | IL-21 + DEGRADA BALL<br>120<br>aCTLA-4 antibody + DEGRADABALL<br>89 | IL-21/aCTLA-4 antibody + DEGRADABALL<br>21 |
| Stomach cancer | SGC-7901 | Tumor size (mm³; 28 day) | 1285 | IL-24<br>423 | IL-24 + DEGRADA BALL<br>121 | |

TABLE 3-continued

| Cancer type | Cell line | Measurement variables | Control (vehicle) | Test group 1 | Test group 2 | Test group 3 |
|---|---|---|---|---|---|---|
| Pancreatic cancer | HS766T | Tumor size (mm²; 28 day) | 81 | IL-13<br><br>14 | IL-13 + DEGRADA BALL<br>3.2 | |
| Head and neck cancer | KCCT873 | Tumor size (mm²; 30 day) | 138 | IL-13<br><br>29<br>IL-13/CpG<br><br>19 | IL-13 + DEGRADA BALL<br>11<br>IL-13 + DEGRADA BALL/CpG<br>4.2 | IL-13 + DEGRADABALL/CpG + DEGRADABALL<br>1.7 |

Example 7. Identification of Side Effect Reduction by the Carrier According to the Present Invention Diverse side effects are involved due to the administration of cytokines. Among those, the side effects due to the administration of IL-2 well known in the art include capillary leak syndrome (CLS) or vascular leak syndrome (VLS). Thus, in order to determine whether the carrier of the present invention has effects of reducing the side effects of a substance supported thereon, an experiment was performed using BALLkine-2, that is, the porous silica particles loaded with IL-2 cytokine.

Figure 83:
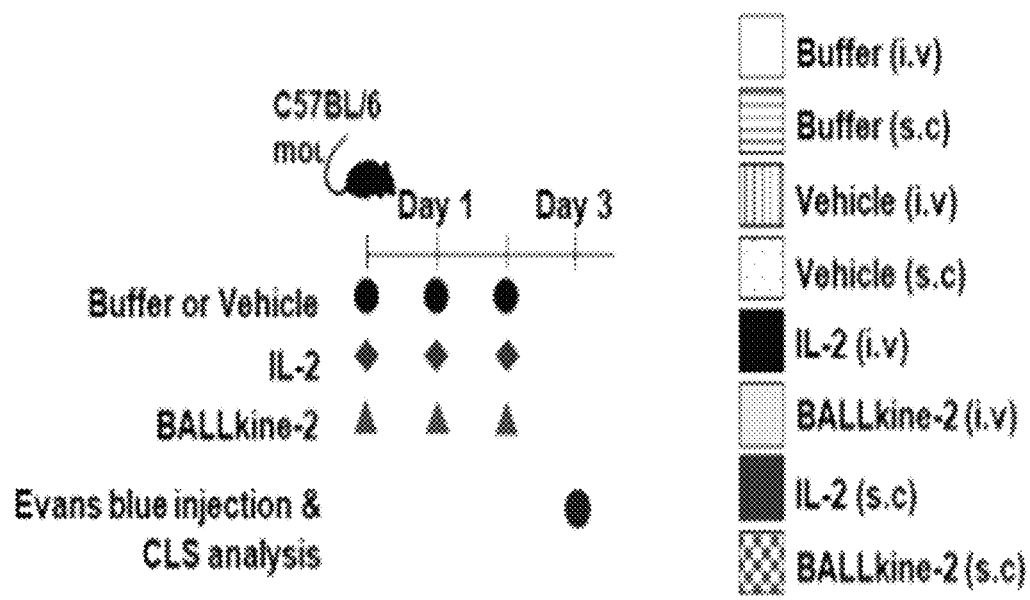
Figure 84:
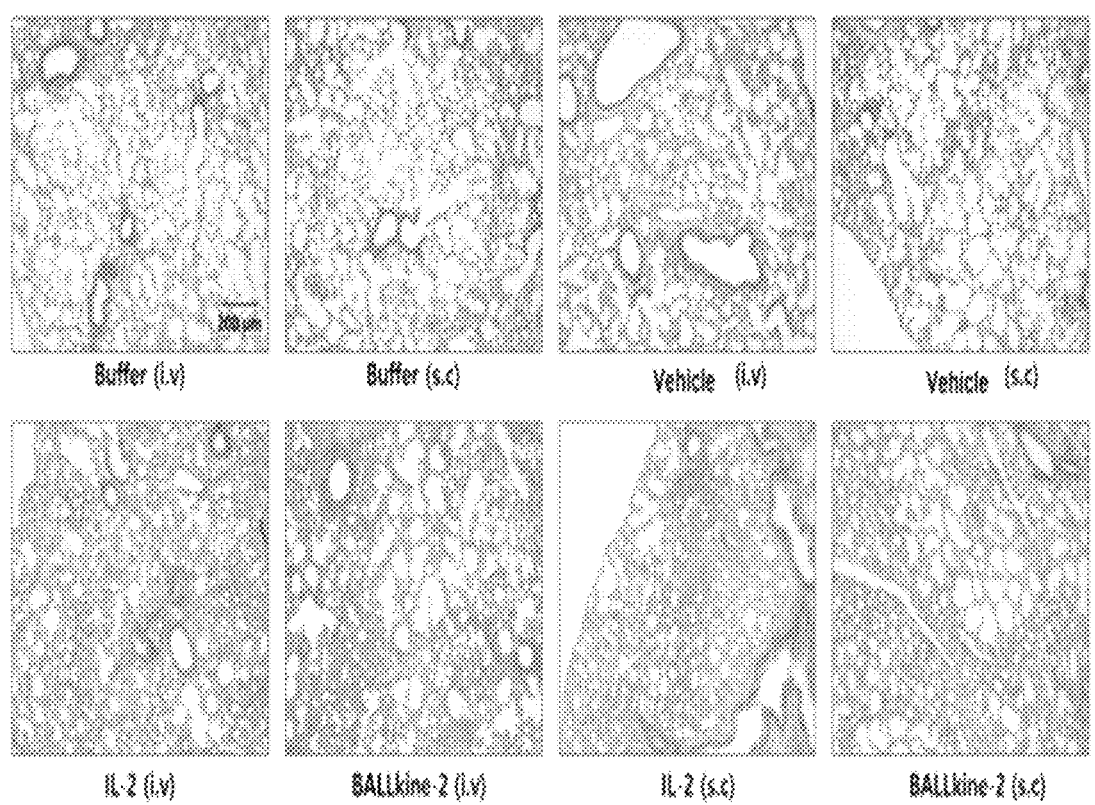
Figure 85:
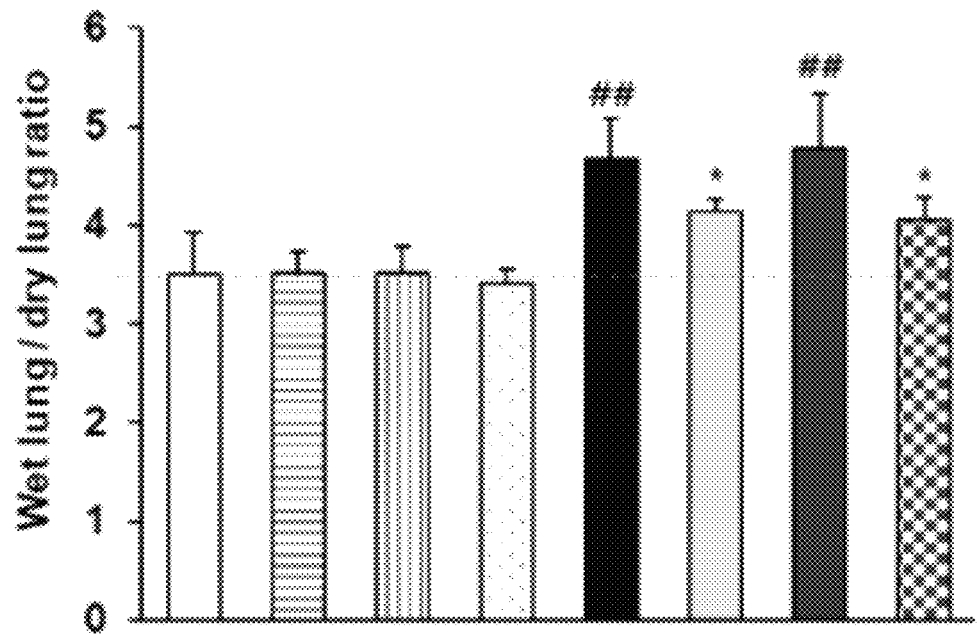
Figure 86:
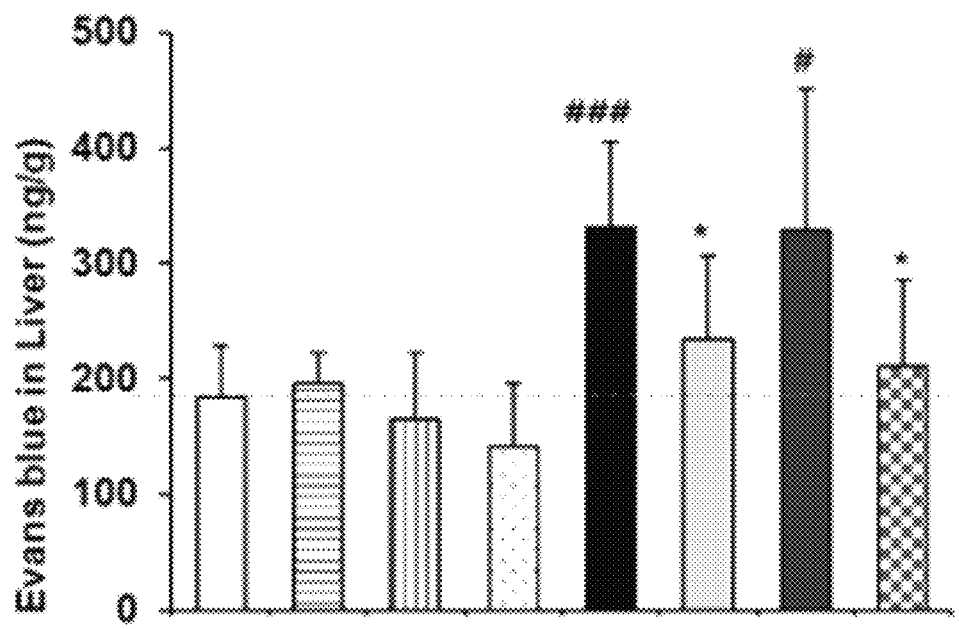
Figure 87:
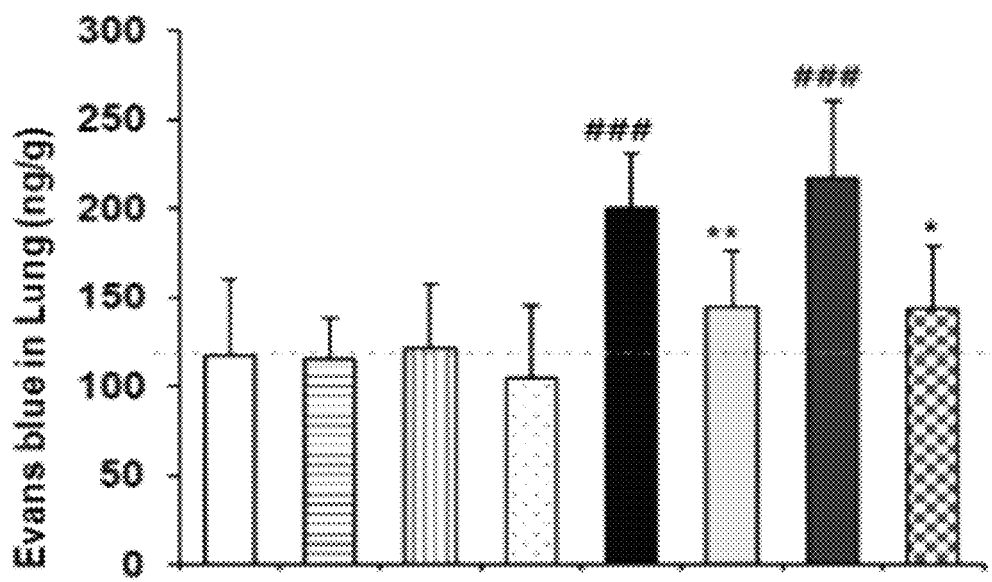
Figure 88:
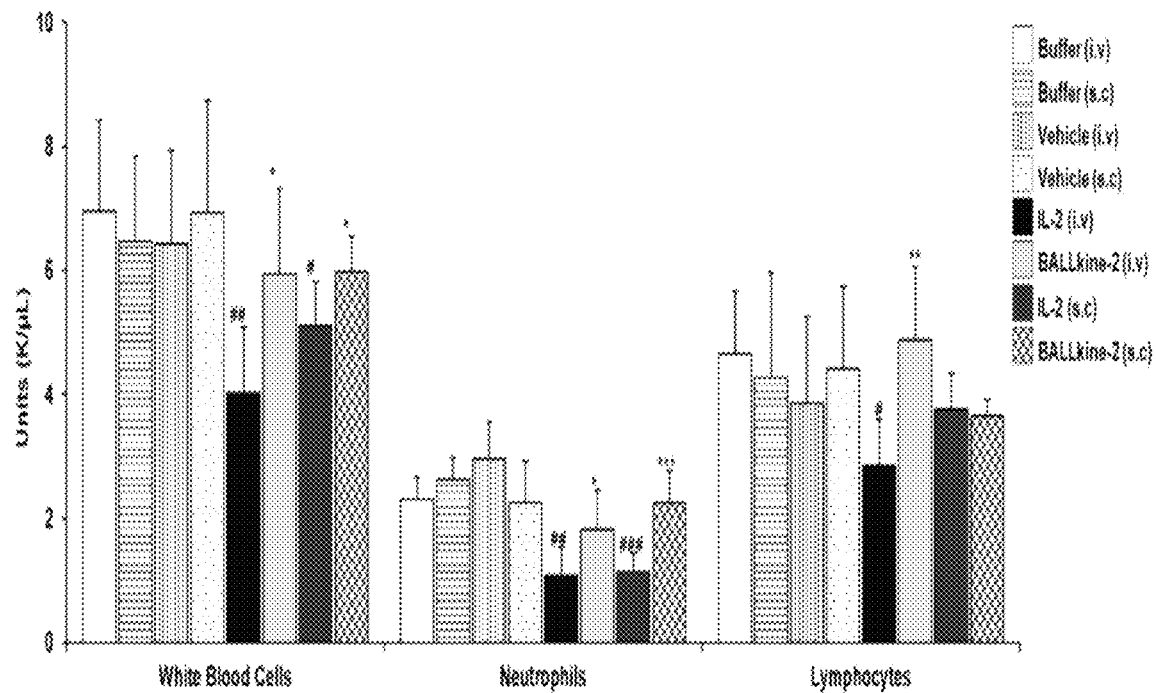

The experiment was performed according to the administration schedule and the CLS analysis protocol shown in FIG. 83. Specifically, 3 days after the administration of IL-2 (15 g) and BALLkine-2 (15 g) to C57BL/6 mice, respectively, the analysis was performed on day 4. Referring to a representative H & E staining image (FIG. 84) of mouse lung tissues to which the buffer (i.v. or s.c.), DEGRADA-BALL (i.v. or s.c.), IL-2 (i.v. or s.c.) or BALLkine-2 (i.v. or s.c.) were administered, it can be seen that the number of inflammatory cells inside or around the blood vessels in the BALLkine-2 administration group is reduced as compared to the IL-2 (i.v. or s.c.) administration group (the rod indicates 200 μm). Further, in order to assess pulmonary edema, wet lungs were separated and weighed, and lungs were dried in an oven at 60° C. for 3 days and then weighted (FIG. 85). As a result, it could be seen that the BALLkine-2 administration group had a weight ratio between wet lung weight and dry lung weight (wet lung weight/dry lung weight) significantly lower than that of the IL-2 (i.v. or s.c.)-administration group, and had similar values to the normal group. Further, mice in the VLS model were injected with Evans blue dye through the tail vein 2 hours before sacrifice, followed by isolating the liver (FIG. 86) and the lung (FIG. 87) after the sacrifice. Then, VLS intensification extent measured through extravasation of Evans blue was analyzed. As a result, it could be seen that the BALLkine-2 administration group showed VLS extravasation significantly lower than the IL-2 (i.v. or s.c.) administration group. Meanwhile, blood was collected for hematological assay of mice on day 3, followed by analysis of leukocytes, neutrophils and lymphocytes. As a result, it could be seen that the number of all these cells was significantly higher in the BALLkine-2 administration group than in the IL-2 (i.v. or s.c.) administration group (FIG. 88, data indicate the mean±SD for: 3 to 4 mice per each of the buffer administration group and the DEGRADABALL treatment group; and 4 to 7 mice per the BALLkine-2 group, significant difference from the buffer administration group (i.v. or s.c.) ($^\#p<0.05$; $^{\#\#}p<0.01$; $^{\#\#\#\#}p<0.001$), significant difference from IL-2 group (i.v. or s.c.) ($*p<0.05$; $p<0.01$; $*p<0.001$)).

Figure 89:
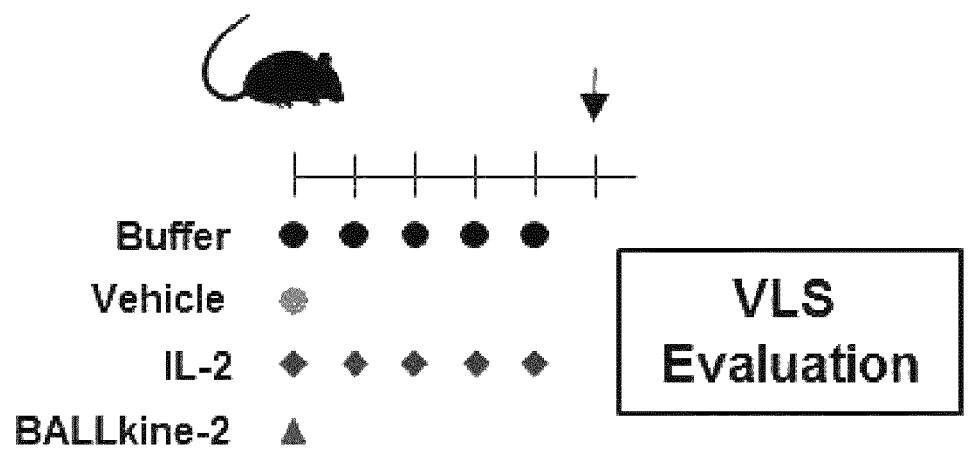
Figure 90:
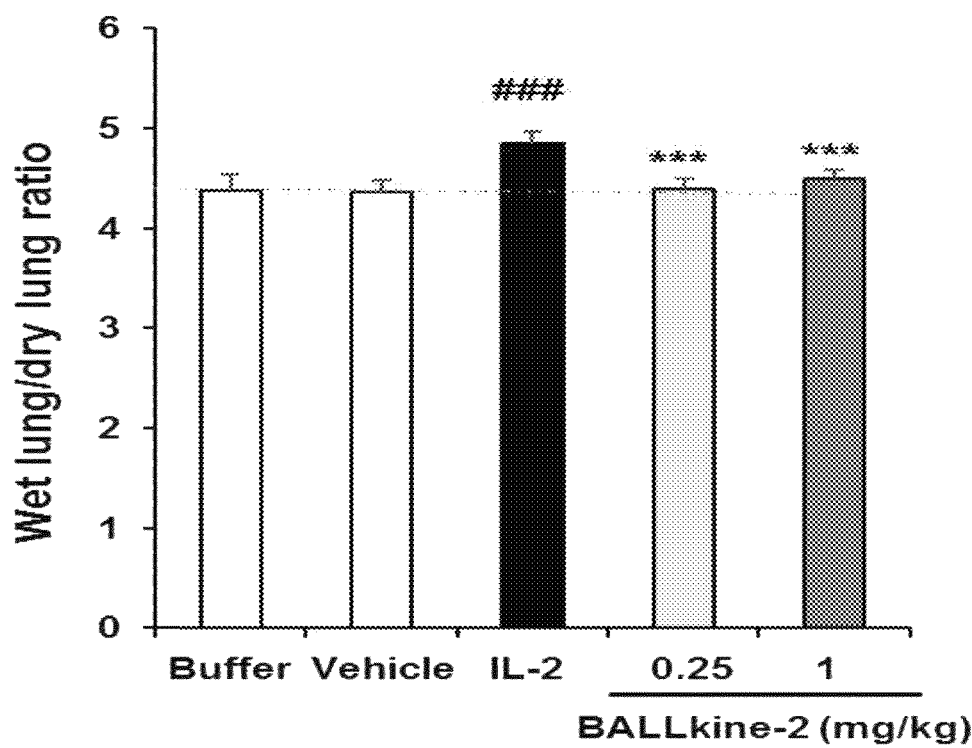
Figure 91:
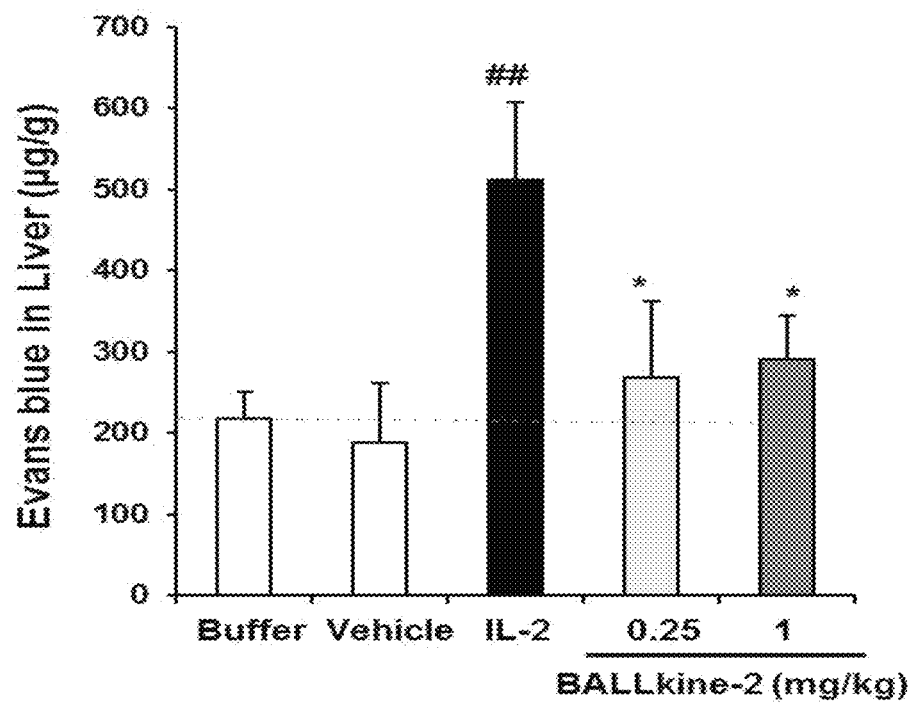
Figure 92:
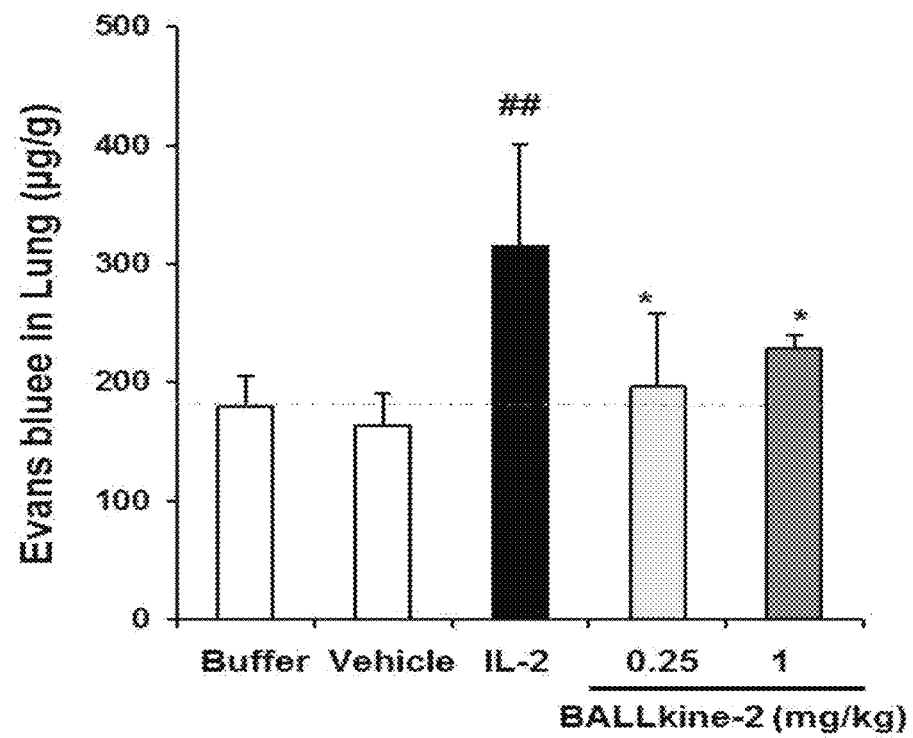

In order to identify whether to reduce vascular leakage syndrome (VLS) even in actual cancer immunotherapy, VLS analysis was performed in a tumor bearing mouse model according to the protocol shown in FIG. 89. In order to assess pulmonary edema, the wet lung was separated and weighed, and the lung was dried in an oven at 60° C. for 3 days and then weighed (FIG. 90). The BALLkine-2 administration group showed a weight ratio significantly lower than the IL-2 (i.v. or s.c.)-administration group, and had similar values to the normal group. In addition, mice in the VLS model were injected with Evans blue dye through the tail vein 2 hours before sacrifice, followed by isolating the liver (FIG. 91) and lung (FIG. 92). Then, VLS measured through extravasation of Evans blue was analyzed. As a result, it could be seen that the BALLkine-2 administration group showed significantly lower VLS extravasation than the IL-2 (i.v. or s.c.) administration group.

The above results are determined to be significant since inherent side effects of an immunoreactive substance such as an antibody or cytokine are remarkably reduced when the porous silica particles of the present invention carry the antibody or cytokine and deliver the same in vivo, thereby demonstrating that original and pharmacological treatment effects may be enhanced.

What is claimed is:

1. A method for treating at least one of a cancer and an immune disease, the method comprising:
administering to a subject in need thereof an immunotherapeutic composition comprising an immunoreactive substance carrier loaded with an immunoreactive substance comprised of at least one of an antibody or cytokine, the immunoreactive substance carrier comprising:
expanded porous silica particles which carry the at least one of an antibody and cytokine,
wherein an average diameter of the expanded porous silica particles ranges from 150 to 1,000 nm, a Brunauer-Emmett-Teller (BET) surface area ranges from 200 to 700 m²/g, and a volume per g ranges from 0.7 to 2.2 ml; and
the expanded porous silica particles are characterized in that t, at which an absorbance ratio in the following Equation 1 becomes ½, is 24 hours or more:

$$A_t/A_0 \quad \text{[Equation 1]}$$

wherein $A_0$ is absorbance of the expanded porous silica particles measured by placing 5 ml of suspension containing 1 mg/ml of the expanded porous silica particles in a cylindrical permeable membrane having pores with a pore diameter of 50 kDa;

15 ml of the same solvent as the suspension comes into contact with outside of the permeable membrane, and the inside/outside of the permeable membrane is horizontally stirred at 60 rpm and 37° C.;

pH of the suspension is 7.4; and $A_t$ indicates absorbance of the expanded porous silica particle measured after lapse of "t" hours since $A_0$ was measured, wherein an outer surface of the immunoreactive substance carrier is an outer surface of the expanded porous silica particle, and the at least one of an antibody or cytokine is supported on the outer surface of the immunoreactive substance carrier and/or an inside of the pores.

2. The method of claim 1, wherein the at least one of the antibody and cytokine comprises the antibody, and the antibody is an antibody specifically bound to interleukins or interferon protein.

3. The method of claim 1, wherein the at least one of the antibody and cytokine comprises the antibody, and the antibody is IgG or an antibody capable of binding to at least one protein selected from the group consisting of PD-1, CTLA-4, TIM-3, BTLA, VISTA, LAG-3, PD-L1, PD-L2, B7-H3, B7-H4, CD28, CD27, CD137, HVEM, GITR, VEGFR, VEGF, EGFR, EGF, IL-1, IL-6, IL-23, TGF-beta, CTGF, TSLP, TNF-alpha, Notch and OX40.

4. The method of claim 1, wherein the at least one of the antibody and cytokine comprises the antibody, and the antibody is an antibody capable of binding to at least one selected from the group consisting of PD-1, PD-L1 and CTLA-4.

5. The method of claim 1, wherein the at least one of the antibody and cytokine comprises the cytokine, and the cytokine is at least one of interleukins and interferons.

6. The method of claim 1, wherein the at least one of the antibody and cytokine comprises the cytokine, and the cytokine is at least one selected from the group consisting of IL-7, IL-10, IL-12, IL-13, IL-15, IL-21, IL-23, IL-24, IL-27, G-CSF, GM-CSF, HGF, EGF, VEGF, LTF, TGF-β and IL-2.

7. The method of claim 1, wherein the at least one of the antibody and cytokine comprises the cytokine, and the cytokine is at least one selected from the group consisting of IL-2, IL-12, IL-15, IL-21, IL-24 and IL-13.

8. The method of claim 1, wherein the expanded porous silica particles have hydrophilic or hydrophobic functional groups on the outer surface thereof or the inside of the pores.

9. The method of claim 8, wherein the expanded porous silica particles have the hydrophilic functional groups on the outer surface.

10. The method of claim 8, wherein the expanded porous silica particles have the hydrophobic functional groups on the outer surface.

11. The method of claim 8, wherein the expanded porous silica particles have the hydrophilic functional groups on the outer surface and the hydrophobic functional groups on the inside of the pores.

12. The method of claim 1, wherein the expanded porous silica particles have hydrophilic or hydrophobic functional groups only on the outer surface thereof.

13. The method of claim 1, wherein the immunoreactive substance is supported on at least one of the outer surface of the expanded porous silica particles and the inside of the pores.

14. The method of claim 1, wherein the immunoreactive substance is supported on both the outer surface of the expanded porous silica particles and the inside of the pores.

* * * * *